United States Patent
Qiao et al.

(10) Patent No.: US 9,873,837 B2
(45) Date of Patent: *Jan. 23, 2018

(54) PRODUCTION OF CHEMICALS AND FUELS FROM BIOMASS

(71) Applicant: Virent, Inc., Madison, WI (US)

(72) Inventors: Ming Qiao, Pewaukee, WI (US); Elizabeth Woods, Middleton, WI (US); Paul Myren, Madison, WI (US); Randy Cortright, Madison, WI (US); John Kania, Madison, WI (US)

(73) Assignee: Virent, Inc., Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/968,344

(22) Filed: Dec. 14, 2015

(65) Prior Publication Data
US 2016/0096996 A1    Apr. 7, 2016

Related U.S. Application Data

(63) Continuation of application No. 13/479,004, filed on May 23, 2012, now Pat. No. 9,212,320.
(Continued)

(51) Int. Cl.
*C07C 1/00* (2006.01)
*C10G 1/06* (2006.01)
(Continued)

(52) U.S. Cl.
CPC ............... *C10G 1/065* (2013.01); *C07C 1/24* (2013.01); *C10G 3/42* (2013.01); *C10G 3/44* (2013.01); *C10G 3/48* (2013.01); *C10G 3/49* (2013.01); *C10G 3/52* (2013.01); *C10G 3/62* (2013.01); *C10L 1/04* (2013.01); *C10L 1/06* (2013.01); *C10L 1/08* (2013.01); *C10G 2300/1014* (2013.01); *C10G 2300/301* (2013.01); *C10G 2300/302* (2013.01); *C10G 2300/305* (2013.01); *C10G 2300/308* (2013.01); *C10G 2300/44* (2013.01); *C10G 2400/02* (2013.01); *C10G 2400/04* (2013.01); *C10G 2400/08* (2013.01); *C10G 2400/30* (2013.01); *Y02E 50/13* (2013.01); *Y02P 30/20* (2015.11)

(58) Field of Classification Search
USPC .................... 585/240; 44/576, 589, 307, 308
See application file for complete search history.

(56) References Cited

U.S. PATENT DOCUMENTS 5,886,266 A * 3/1999 Stiller .............. B60K 15/03504
                                                    73/715
6,699,457 B2 * 3/2004 Cortright .................. C01B 3/22
                                                   423/648.1
(Continued)

*Primary Examiner* — Nina Bhat
(74) *Attorney, Agent, or Firm* — Quarles & Brady LLP

(57) ABSTRACT

Methods, reactor systems, and catalysts are provided for converting in a continuous process biomass to fuels and chemicals, including methods of converting the water insoluble components of biomass, such as hemicellulose, cellulose and lignin, to volatile $C_{2+}O_{1-2}$ oxygenates, such as alcohols, ketones, cyclic ethers, esters, carboxylic acids, aldehydes, and mixtures thereof. In certain applications, the volatile $C_{2+}O_{1-2}$ oxygenates can be collected and used as a final chemical product, or used in downstream processes to produce liquid fuels, chemicals and other products.

24 Claims, 34 Drawing Sheets

Related U.S. Application Data

(60) Provisional application No. 61/489,135, filed on May 23, 2011.

(51) Int. Cl.
*C10G 3/00* (2006.01)
*C10L 1/04* (2006.01)
*C10L 1/06* (2006.01)
*C10L 1/08* (2006.01)
*C07C 1/24* (2006.01)

(56) References Cited

U.S. PATENT DOCUMENTS

| | | | |
|---|---|---|---|
| 6,953,873 B2* | 10/2005 | Cortright | C07C 1/20 585/357 |
| 8,148,553 B2* | 4/2012 | Dumesic | B01J 23/6484 549/326 |
| 2008/0216391 A1* | 9/2008 | Cortright | C10G 3/45 44/307 |
| 2009/0211942 A1* | 8/2009 | Cortright | B01J 23/6567 208/15 |
| 2010/0076233 A1* | 3/2010 | Cortright | B01J 23/6567 585/251 |
| 2010/0256428 A1* | 10/2010 | Marker | C01B 3/16 585/240 |

* cited by examiner

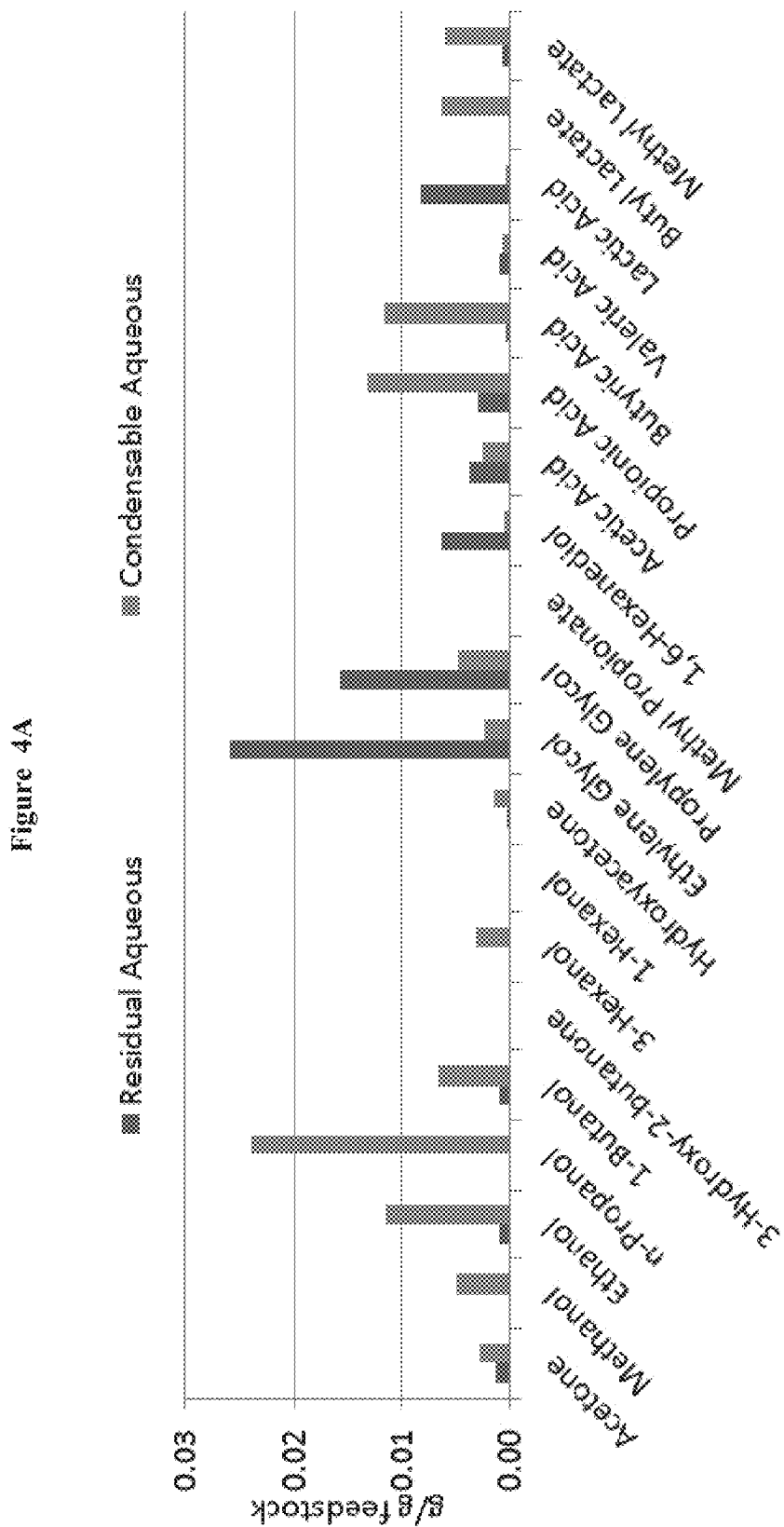

PRODUCTION OF CHEMICALS AND FUELS FROM BIOMASS

CROSS-REFERENCE TO RELATED APPLICATION

This application is a continuation of U.S. application Ser. No. 13/479,004, filed May 23, 2012, now U.S. Pat. No. 9,212,320, which claims the benefit of U.S. Provisional Application No. 61/489,135 filed on May 23, 2011.

FEDERALLY SPONSORED RESEARCH OR DEVELOPMENT

This invention was made with government support under an award provided by the U.S. Department of Energy, Award No. DE-EE0003044. The government has certain rights in the invention.

TECHNICAL FIELD

The present invention is directed to catalysts and methods for converting biomass into liquid fuels and chemicals.

BACKGROUND OF THE INVENTION

Increasing cost of fossil fuel and environmental concerns have stimulated worldwide interest in developing alternatives to petroleum-based fuels, chemicals, and other products. Biomass materials are a possible renewable alternative to petroleum-based fuels and chemicals.

Lignocellulosic biomass includes three major components. Cellulose, a primary sugar source for bioconversion processes, includes high molecular weight polymers formed of tightly linked glucose monomers. Hemicellulose, a secondary sugar source, includes shorter polymers formed of various sugars. Lignin includes phenylpropanoic acid moieties polymerized in a complex three dimensional structure. The resulting composition of lignocellulosic biomass is roughly 40-50% cellulose, 20-25% hemicellulose, and 25-35% lignin, by weight percent.

Very few cost-effective processes exist for efficiently converting cellulose, hemicellulose and lignin to components better suited for producing fuels, chemicals, and other products. This is generally because each of lignin, cellulose and hemicellulose demands distinct processing conditions, such as temperature, pressure, catalysts, reaction time, etc., in order to effectively break apart their polymer structure. Because of this distinctness, most processes are only able to convert specific fractions of the biomass, such as cellulose and hemicellulose, leaving the remaining fractions behind for additional processing or alternative uses.

Hot water extraction of hemicellulose from biomass, for example, has been well documented. The sugars produced by hot water extraction are however unstable at high temperatures leading to undesirable decomposition products. Therefore, the temperature of the water used for hot water extraction is limited, which can reduce the effectiveness of the hot water extraction.

Studies have also shown that it is possible to convert microcrystalline cellulose (MCC) to polyols using hot, compressed water and a hydrogenation catalyst (Fukuoka & Dhepe, 2006; Luo et al., 2007; and Yan et al., 2006). Typical hydrogenation catalysts include ruthenium or platinum supported on carbon or aluminum oxide. However, these studies also show that only low levels of MCC are converted with these catalysts, and selectivity toward desired sugar alcohols is low.

APR and HDO are catalytic reforming processes that have recently shown to be promising technologies for generating hydrogen, oxygenates, hydrocarbons, fuels, and chemicals from oxygenated compounds derived from a wide array of biomass. The oxygenated hydrocarbons include starches, mono- and poly-saccharides, sugars, sugar alcohols, etc. Various APR methods and techniques are described in U.S. Pat. Nos. 6,699,457; 6,964,757; 6,964,758; and 7,618,612 (all to Cortright et al., and entitled "Low-Temperature Hydrogen Production from Oxygenated Hydrocarbons"); U.S. Pat. No. 6,953,873 (to Cortright et al., and entitled "Low-Temperature Hydrocarbon Production from Oxygenated Hydrocarbons"); and U.S. Pat. Nos. 7,767,867; 7,989,664; and U.S. Patent Publication No. 2011/0306804 (to Cortright, and entitled "Methods and Systems for Generating Polyols"). Various APR and HDO methods and techniques are described in U.S. Pat. Nos. 8,053,615; 8,017,818; 7,977,517; and U.S. Patent Publication Nos. 2011/0257448; 2011/0245543; 2011/0257416; and 2011/0245542 (all to Cortright and Blommel, and entitled "Synthesis of Liquid Fuels and Chemicals from Oxygenated Hydrocarbons"); U.S. Patent Publication No. 2009/0211942 (to Cortright, and entitled "Catalysts and Methods for Reforming Oxygenated Compounds"); U.S. Patent Publication No. 2010/0076233 (to Cortright et al., and entitled "Synthesis of Liquid Fuels from Biomass"); International Patent Application No. PCT/US2008/056330 (to Cortright and Blommel, and entitled "Synthesis of Liquid Fuels and Chemicals from Oxygenated Hydrocarbons"); and commonly owned co-pending International Patent Application No. PCT/US2006/048030 (to Cortright et al., and entitled "Catalyst and Methods for Reforming Oxygenated Compounds"), all of which are incorporated herein by reference.

One drawback of catalytic technologies is the possible negative effects of water, contaminants, and other residual products on the performance of the catalyst. For instance, ash components (e.g., calcium, aluminum, potassium, sodium, magnesium, ammonium, chloride, sulfate, sulfite, thiol, silica, copper, iron, phosphate, carbonate, and phosphorous), color bodies (e.g., terpenoids, stilbenes, and flavonoids), proteinaceous materials, and other inorganic or organic products from biomass conversion can interact with the catalyst to severely limit its activity. More complex polysaccharides, such as raw cellulose and hemicellulose, as well as lignin, and their complex degradation products, have also proven to be difficult to convert due to their size and inability to interact with the catalyst. Therefore, a process for generating fuels and chemicals and other hydrocarbons and oxygenated hydrocarbons from more complex biomass components would be beneficial. It would also be beneficial to improve the efficiency of such processes by minimizing the number of reaction steps, and thus reactors, necessary to perform the conversion process.

SUMMARY

The invention provides methods for making biomass-derived fuels and chemicals. The method generally involves: (1) providing a biomass feed stream comprising a solvent and a biomass component comprising cellulose, hemicellulose or lignin; (2) catalytically reacting the biomass feed stream with hydrogen and a deconstruction catalyst at a deconstruction temperature and a deconstruction pressure to produce a product stream comprising a vapor phase, a liquid phase and a solid phase, the vapor phase comprising one or more volatile $C_{2+}O_{1-2}$ oxygenates, the liquid phase comprising water and one or more $C_{2+}O_{2+}$ oxygenated hydrocarbons, and the solid phase comprising extractives; (3) separating the volatile $C_{2+}O_{1-2}$ oxygenates from the liquid phase and solid phase; and (4) catalytically reacting the volatile $C_{2+}O_{1-2}$ oxygenates in the presence of a condensation catalyst at a condensation temperature and condensation pressure to produce a $C_{4+}$ compound comprising a member selected from the group consisting of $C_{4+}$ alcohol, $C_{4+}$ ketone, $C_{4+}$ alkane, $C_{4+}$ alkene, $C_{5+}$ cycloalkane, $C_{5+}$ cycloalkene, aryl, fused aryl, and a mixture thereof. In one embodiment, the deconstruction temperature is between about 120° C. to 350° C. In another embodiment, the deconstruction pressure is between about 300 psi to 2500 psi.

One aspect of the invention is the composition of the solvent. In one embodiment, the solvent includes one or more members selected from the group consisting of water, in situ generated $C_{2+}O_{2+}$ oxygenated hydrocarbons, recycled $C_{2+}O_{2+}$ oxygenated hydrocarbons, bioreforming solvents, organic solvents, organic acids, and a mixture thereof.

In another embodiment, the biomass component comprises at least one member selected from the group including recycled fibers, corn stover, bagasse, switch grass, miscanthus, sorghum, wood, wood waste, agricultural waste, algae, and municipal waste.

The deconstruction catalyst may comprise an acidic or basic support, or a support and a member selected from the group consisting of Ru, Co, Rh, Pd, Ni, Mo, and alloys thereof. In another embodiment, the deconstruction catalyst may further comprise a member selected from the group consisting of Pt, Re, Fe, Ir, Cu, Mn, Cr, Mo, B, W, V, Nb, Ta, Ti, Zr, Y, La, Sc, Zn, Cd, Ag, Au, Sn, Ge, P, Al, Ga, In, Tl, and alloys thereof. In yet another embodiment, the support comprises a member selected from the group consisting of a nitride, carbon, silica, alumina, zirconia, titania, vanadia, ceria, boron nitride, heteropolyacid, kieselguhr, hydroxyapatite, zinc oxide, chromia, zeolites, tungstated zirconia, titania zirconia, sulfated zirconia, phosphated zirconia, acidic alumina, silica-alumina, sulfated alumina, phosphated alumina, and mixtures thereof. In a further embodiment, the support is modified by treating the support with a modifier selected from the group consisting of tungsten, titania, sulfate, phosphate, or silica.

Another aspect of the invention is a solid phase. In one embodiment, the solid phase further comprises the deconstruction catalyst. In yet another embodiment, the deconstruction catalyst is separated from the liquid phase; washed in one or more washing medium; regenerated in the presence of oxygen or hydrogen, at a regenerating pressure and a regenerating temperature wherein carbonaceous deposits are removed from the deconstruction catalyst; and then reintroduced to react with the biomass feed stream.

In one embodiment the washing medium comprises a liquid selected from the group consisting of water, an acid, a base, a chelating agent, alcohols, ketones, cyclic ethers, hydroxyketones, aromatics, alkanes, and combinations thereof. In another embodiment, the washing of the deconstruction catalyst comprises a first step of washing the deconstruction catalysts with a first washing solvent and a second step of washing the deconstruction catalyst with a second washing solvent. In yet another embodiment, the first washing solvent comprises a liquid selected from the group consisting of water, an acid, a base, a chelating agent, and combinations thereof, and the second washing solvent comprises a liquid selected from the group consisting of alcohols, ketones, cyclic ethers, hydroxyketones, aromatics, alkanes, and combinations thereof. In yet another embodiment, the first washing solvent comprises a liquid selected from the group consisting of alcohols, ketones, cyclic ethers, hydroxyketones, aromatics, alkanes, and combinations thereof, and the second washing solvent comprises a liquid selected from the group consisting of water, an acid, a base, a chelating agent, and combinations thereof.

In one embodiment, the deconstruction catalyst is regenerated at a temperature of in the range of about 120° C. to about 450° C., and is adjusted at a rate of about 20° C. per hour to about 60° C. per hour. In another embodiment, regeneration of the deconstruction catalyst further comprises providing a gas stream comprising an inert gas and oxygen, the inert gas provided at a gas flow of between 600-1200 ml gas/ml catalyst per hour and the oxygen provided at a concentration of 0.5-10% of the gas stream. In yet another embodiment, regeneration results in removal of more than 90% of the carbonaceous deposits from the deconstruction catalyst.

The catalytic reaction of the volatile $C_{2+}O_{1-2}$ oxygenates takes place in the presence of a condensation catalyst. In one embodiment the condensation catalyst comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy thereof, and a combination thereof. In another embodiment, the condensation catalyst further comprises a modifier selected from the group consisting of Ce, La, Y, Li, Na, K, Rb, Cs, Mg, Ca, Sr, Ba, P, B, Bi, and a combination thereof. In yet another embodiment, the condensation catalyst comprises a member selected from the group consisting of an acidic alumina, aluminum phosphate, silica-alumina phosphate, amorphous silica-alumina, sulfated alumina, theta alumina, aluminosilicate, zeolites, zirconia, sulfated zirconia, tungstated zirconia, titania zirconia, phosphated zirconia, tungsten carbide, molybdenum carbide, titania, sulfated carbon, phosphated carbon, phosphated silica, phosphated alumina, acidic resin, heteropolyacid, inorganic acid, and a combination thereof.

The catalytic reaction of the volatile $C_{2+}O_{1-2}$ oxygenates in the presence of a condensation catalyst produces a $C_{4+}$ compound. In one embodiment, the $C_{4+}$ compound is benzene, toluene or xylene.

The biomass feed stream is catalytically reacted with the deconstruction catalyst in the presence of hydrogen. In one embodiment, the hydrogen is selected from the group consisting of external hydrogen, recycled hydrogen or in situ generated hydrogen. In another embodiment, the in situ generated hydrogen is derived from the $C_{2+}O_{2+}$ oxygenated hydrocarbons.

The invention also provides a method of generating a product mixture comprising two or more $C_{4+}$ compounds. The method generally involves: (1) providing a biomass feed stream comprising a solvent and a biomass component comprising cellulose, hemicellulose or lignin; (2) catalytically reacting the biomass feed stream with hydrogen and a deconstruction catalyst at a deconstruction temperature and a deconstruction pressure to produce a product stream comprising a vapor phase, a liquid phase and a solid phase, the vapor phase comprising one or more volatile $C_{2+}O_{1-2}$ oxygenates, the liquid phase comprising water and one or more $C_{2+}O_{2+}$ oxygenated hydrocarbons, and the solid phase comprising extractives; (3) separating the volatile $C_{2+}O_{1-2}$ oxygenates from the liquid phase and solid phase; (4) catalytically reacting the volatile $C_{2+}O_{1-2}$ oxygenates in the presence of a condensation catalyst at a condensation temperature and condensation pressure to produce a product mixture comprising two or more $C_{4+}$ compounds selected from the group consisting of a $C_{4+}$ alcohol, a $C_{4+}$ ketone, a $C_{4+}$ alkane, a $C_{4+}$ alkene, a $C_{5+}$ cycloalkane, a $C_{5+}$ cycloalkene, a aryl, and a fused aryl; and (5) distilling the product mixture to provide a composition selected from the group consisting of an aromatic fraction, a gasoline fraction, a kerosene fraction and a diesel fraction.

In one embodiment, the aromatic fraction comprises benzene, toluene or xylene. In another embodiment, the gasoline fraction has a final boiling point in the range of from 150° C. to 220° C., a density at 15° C. in the range of from 700 to 890 kg/m³, a RON in the range of from 80 to 110, and a MON in the range of from 70 to 100. In yet another embodiment, the kerosene fraction has an initial boiling point in the range of from 120° C. to 215° C., a final boiling point in the range of from 220° C. to 320° C., a density at 15° C. in the range of from 700 to 890 kg/m³, a freeze point of −40° C. or lower, a smoke point of at least 18 mm, and a viscosity at −20° C. in the range of from 1 to 10 cSt. And in yet another embodiment, the diesel fraction has a T95 in the range of from 220° C. to 380° C., a flash point in the range of from 30° C. to 70° C., a density at 15° C. in the range of from 700 to 900 kg/m³, and a viscosity at 40° C. in the range of from 0.5 to 6 cSt.

The invention also provides a method for generating $C_{4+}$ compounds from a biomass feed stream comprising cellulose, hemicellulose, and lignin. The method generally involves: (1) providing a biomass feed stream comprising a solvent and a biomass component, the solvent comprising one or more members selected from the group consisting of water, in situ generated $C_{2+}O_{2+}$ oxygenated hydrocarbons, recycled $C_{2+}O_{2+}$ oxygenated hydrocarbons, bioreforming solvents, organic solvents, organic acids, and a mixture thereof, and the biomass component comprising cellulose, hemicellulose and lignin; (2) catalytically reacting the biomass feed stream with hydrogen and a deconstruction catalyst at a deconstruction temperature and a deconstruction pressure to produce a product stream comprising a vapor phase, a liquid phase and a solid phase, the vapor phase comprising one or more volatile $C_{2+}O_{1-2}$ oxygenates, the liquid phase comprising water and one or more $C_{2+}O_{2+}$ oxygenated hydrocarbons, the solid phase comprising extractives, and the deconstruction catalyst comprising a support and a first member selected from the group consisting of Ru, Co, Rh, Pd, Ni, Mo, and alloys thereof, and at least one additional member selected from the group consisting of Pt, Re, Fe, Ir, Cu, Mn, Cr, Mo, B, W, V, Nb, Ta, Ti, Zr, Y, La, Sc, Zn, Cd, Ag, Au, Sn, Ge, P, Al, Ga, In, Tl, and alloys thereof; (3) separating the volatile $C_{2+}O_{1-2}$ oxygenates from the liquid phase and solid phase; and (4) catalytically reacting the volatile $C_{2+}O_{1-2}$ oxygenates in the presence of a condensation catalyst at a condensation temperature and condensation pressure to produce a $C_{4+}$ compound comprising a member selected from the group consisting of $C_{4+}$ alcohol, $C_{4+}$ ketone, $C_{4+}$ alkane, $C_{4+}$ alkene, $C_{5+}$ cycloalkane, $C_{5+}$ cycloalkene, aryl, fused aryl, and a mixture thereof.

Other aspects of the invention include: (1) a chemical composition comprising a $C_{4+}$ compound derived from any of the foregoing methods; (2) a chemical composition comprising a $C_{4+}$ compound derived from any of the foregoing methods, wherein the $C_{4+}$ compound is benzene, toluene or xylene; (3) a chemical composition comprising a gasoline fraction derived from any of the foregoing methods; (4) a chemical composition comprising a kerosene fraction derived from any of the foregoing methods; and (5) a chemical composition comprising a diesel fraction derived from any of the foregoing methods.

DESCRIPTION OF THE DRAWINGS

FIGS. 4a and 4b are graphs providing the most abundant aqueous product speciation and identified aqueous product distribution, respectively, from the conversion of a biomass feed stream containing MCC according to the present invention.

DETAILED DESCRIPTION OF THE INVENTION

Figure 1:
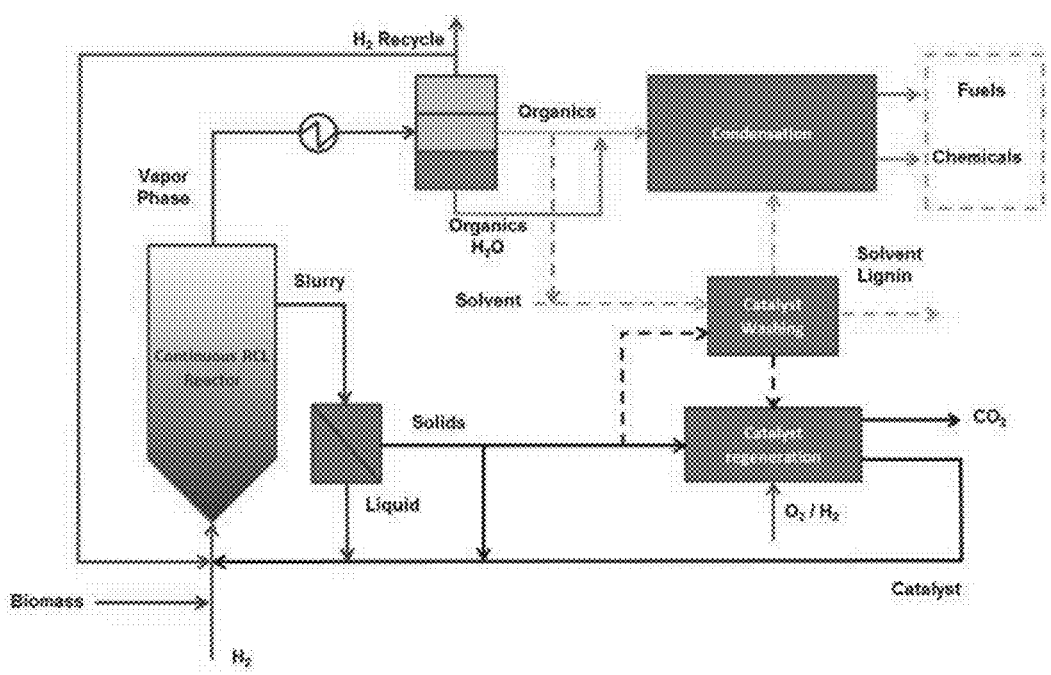
FIG. 1 is a flow diagram illustrating one embodiment of the present invention.

The present invention relates to methods, reactor systems, and catalysts for converting biomass to liquid fuels and chemicals in a batch and/or continuous process. The invention includes methods of converting both water-insoluble and water-soluble components of biomass to volatile oxygenated hydrocarbons, such as $C_{2+}O_{1-2}$ alcohols, ketones, cyclic ethers, esters, carboxylic acids, aldehydes, and mixtures thereof. In certain applications, the volatile oxygenated hydrocarbons can be collected and used as a final chemical product, or used in downstream processes to produce liquid fuels, chemicals and other products.

As used herein, the term "biomass" refers to, without limitation, organic materials produced by plants (e.g., wood, leaves, roots, seeds, stalks, etc.), and microbial and animal metabolic wastes. Common biomass sources include: (1) agricultural residues, such as corn stalks, straw, seed hulls, sugarcane leavings, bagasse, nutshells, and manure from cattle, poultry, and hogs; (2) wood materials, such as wood or bark, sawdust, timber slash, and mill scrap; (3) municipal waste, such as waste paper and yard clippings; (4) energy crops, such as poplars, willows, switch grass, miscanthus, sorghum, alfalfa, prairie bluestream, corn, soybean, and the like; (5) residual solids from industrial processes, such as lignin from pulping processes, acid hydrolysis or enzymatic hydrolysis; and (6) algae-derived biomass, including carbohydrates and lipids from microalgae (e.g., *Botryococcus braunii, Chlorella, Dunaliella tertiolecta, Gracilaria, Pleurochyrsis carterae*, and *Sargassum*) and macroalgae (e.g., seaweed). The term also refers to the primary building blocks of the above, namely, lignin, cellulose, hemicellulose and carbohydrates, such as saccharides, sugars and starches, among others.

As used herein, the term "bioreforming" refers to, without limitation, processes for catalytically converting biomass to lower molecular weight hydrocarbons and oxygenated compounds, such as alcohols, ketones, cyclic ethers, esters, carboxylic acids, aldehydes, diols and other polyols, using heterogeneous catalysts. Bioreforming also includes the further catalytic conversion of such lower molecular weight oxygenated compounds to $C_{4+}$ compounds.

The deconstruction catalysts used herein demonstrate increased tolerance to conditions and species that are typically deleterious to catalyst activity. These species may include ash components (e.g., calcium, aluminum, potassium, sodium, magnesium, ammonium, chloride, sulfate, sulfite, thiol, silica, copper, iron, phosphate, carbonate, and phosphorous), color bodies (e.g., terpenoids, stilbenes, and flavonoids), proteinaceous materials, and other inorganic or organic products. In combination with the solvents and reactor conditions described herein, the deconstruction catalysts also demonstrate increased activity for the conversion of more complex polysaccharides, such as raw cellulose and hemicellulose, as well as lignin, and their complex degradation products.

In the present invention, the principal components of biomass (lignin, cellulose and hemicellulose) are converted to volatile oxygenated hydrocarbons (referred to herein as volatile oxygenates and/or $C_{2+}O_{1-2}$ oxygenates) using hydrogen, a solvent, and a heterogeneous deconstruction catalyst in a continuous process. An exemplary embodiment of the present invention is illustrated in FIG. 1. A biomass feed stream is created by combining solid biomass that has been chopped, shredded, pressed, ground or processed to a size amenable for conversion, with a solvent (e.g., water, in situ generated $C_{2+}O_{2+}$ oxygenated hydrocarbons, recycled $C_{2+}O_{2+}$ oxygenated hydrocarbons, bioreforming solvents, organic solvents, organic acids, and a mixtures thereof). The feed stream is then passed into a reactor where it reacts with hydrogen and the deconstruction catalyst at a deconstruction temperature and a deconstruction pressure to cause a reaction that converts all or at least a portion of the lignin, cellulose, and hemicellulose in the biomass to a product stream that includes a vapor phase containing one or more volatile oxygenates, a liquid phase containing a solution or mixture of oxygenated hydrocarbons, and a solid phase containing extractives and, in certain applications, unreacted or under-reacted biomass and/or the deconstruction catalyst.

Alternatively, a biomass feed stream is created by adding solid biomass that has been chopped, shredded, pressed, ground or processed to a size amenable for conversion, to a reactor containing a solvent, i.e. in a non-slurry form. The solvent (e.g., water, in situ generated $C_{2+}O_{2+}$ oxygenated hydrocarbons, recycled $C_{2+}O_{2+}$ oxygenated hydrocarbons, bioreforming solvents, organic solvents, organic acids, or mixtures thereof) interacts with the solid biomass, thereby making it accessible for reaction with hydrogen and the deconstruction catalyst at a deconstruction temperature and a deconstruction pressure. The reaction converts all or at least a portion of the lignin, cellulose, and hemicellulose in the biomass to a product stream that includes a vapor phase containing one or more volatile oxygenates, a liquid phase containing a solution or mixture of $C_{2+}O_{2+}$ oxygenated hydrocarbons (a portion of which serves as the solvent), and a solid phase containing extractives and, in certain applications, unreacted or under-reacted biomass and/or the deconstruction catalyst.

Figure 2:
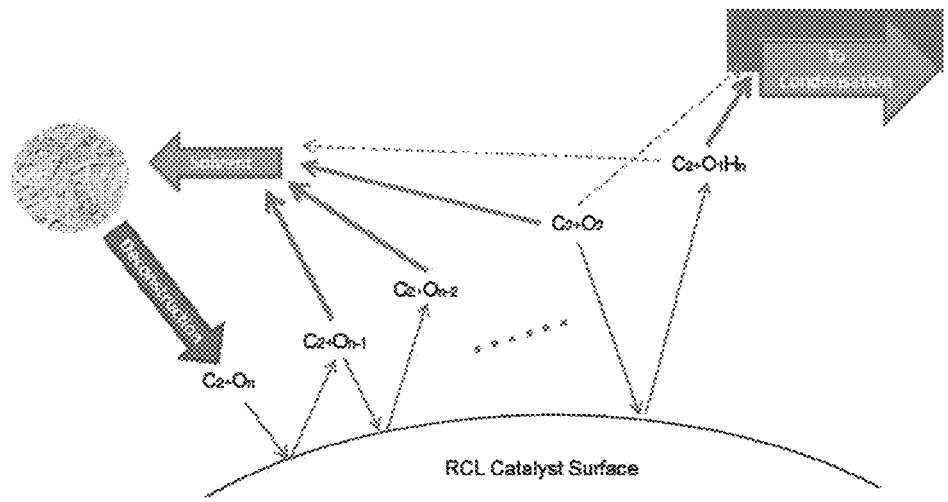
FIG. 2 is an illustration of one exemplary reaction pathway for the conversion of biomass according to the present invention.

In a liquefaction reactor, as illustrated in FIG. 1, biomass (e.g., solid biomass or biomass slurry) is initially deconstructed to produce a solution and/or mixture of oxygenated hydrocarbons, such as hemicellulose, cellulose, polysaccharides, oligosaccharides, sugars, sugar alcohols, sugar degradation products, depolymerized lignin compounds, and the like. As these components are exposed to the deconstruction catalyst and hydrogen, the oxygen content of the compounds is reduced (see FIG. 2) to provide both volatile oxygenates and $C_{2+}O_{2+}$ oxygenated hydrocarbons. The $C_{2+}O_{2+}$ oxygenated hydrocarbons form an in situ generated solvent within the reactor that, in turn: 1) enhances biomass deconstruction, 2) improves the solubility of the deconstructed biomass components—particularly the lignin derived components—to facilitate reaction with the catalyst, and 3) is further deoxygenated to produce the desired volatile oxygenates. The volatile oxygenates then exit the deconstruction reactor as a condensable vapor product for further processing or use in industrial chemicals. Residual oxygenated hydrocarbons can also exit the deconstruction reactor as a liquid phase and be recycled back to the reactor for further conversion and/or use as a solvent or separated for further processing or use as industrial chemicals.

The composition of the phases of the product stream will vary depending on the process conditions and the particular type of biomass feedstock employed. The vapor phase will generally contain volatile oxygenates, hydrogen, carbon monoxide, carbon dioxide, and light alkanes. As used herein, volatile oxygenates refers to oxygenated hydrocarbons having a relative volatility ($\alpha$) with respect to 1-hexanol of greater than 0.03 based on pure components at 250° C. The volatile oxygenates will generally include mono-oxygenated hydrocarbons and di-oxygenated hydrocarbons (collectively referred to herein as $C_{2+}O_{1-2}$ oxygenates), as well as residual oxygenated compounds capable of being volatilized based on the temperature, total pressure, and concentration of the compounds. Mono-oxygenated hydrocarbons generically refers to hydrocarbon compounds having 2 or more carbon atoms and 1 oxygen atom (referred to herein as $C_{2+}O_1$ hydrocarbons), such as alcohols, ketones, aldehydes, ethers, cyclic ethers, and furans. Di-oxygenated hydrocarbons generically refers to hydrocarbon compounds having 2 or more carbon atoms and 2 oxygen atoms (referred to herein as $C_{2+}O_2$ hydrocarbons), and may include, without limitations, diols, di-oxygenated ketones, and organic acids. Residual oxygenated compounds may include components containing three or more oxygen atoms, such as glycerol, which are volatilized due to the processing conditions and their concentration in the reaction stream.

The volatile oxygenates will generally have greater than 2 or greater than 3 carbon atoms, and less than 10 or less than 6 carbon atoms. Preferably, the volatile oxygenates have from 2 to 10 carbon atoms, or 2 to 6 carbon atoms, or 3 to 6 carbon atoms. Volatile oxygenates that are alcohols may include, without limitation, primary, secondary, linear, branched or cyclic $C_{2+}$ alcohols, such as ethanol, n-propyl alcohol, isopropyl alcohol, butyl alcohol, isobutyl alcohol, butanol, pentanol, cyclopentanol, hexanol, cyclohexanol, methyl-cyclohexanol, ethyl-cyclohexanol, propyl-cyclohexanol, 2-methyl-cyclopentanonol, heptanol, octanol, nonanol, decanol, undecanol, dodecanol, and isomers thereof. The alcohols may also include phenols and alkyl substituted phenols, such as methyl, ethyl and propyl phenols, and ortho-, meta-, para-cresols. Volatile ketone oxygenates may include, without limitation, cyclic ketones, aromatic ketones, acetone, propanone, butanone, pentanone, cyclopentanone, hexanone, cyclohexanone, acetophenone, 2-methyl-cyclopentanone, heptanone, octanone, nonanone, decanone, undecanone, dodecanone, and isomers thereof, as well as di-oxygenated ketones, such as hydroxyketones, diketones, butane-2,3-dione, 3-hydroxybutan-2-one, pentane-2,3-dione, pentane-2,4-dione, 2-oxopropanal, methylglyoxal, butanedione, pentanedione, diketohexane, and isomers thereof. The aldehydes may include, without limitation, pentanal, acetaldehyde, hydroxyaldehydes, propionaldehyde, butyraldehyde, hexanal, heptanal, octanal, nonal, decanal, undecanal, dodecanal, and isomers thereof. The ethers may include, without limitation, ethers, such as diethyl ether, diisopropyl ether, 2-ethylhexyl ether, methylethyl ether, ethylpropyl ether, and methylpropyl ether. The cyclic ethers may include, without limitation, tetrahydrofuran, 2-methyl-tetrahydrofuran, 2,5-dimethyl-tetrahydrofuran, 2-ethyl-tetrahydrofuran, and isomers thereof, as well as di-oxygenated cyclic ethers, such as 3-hydroxytetrahydrofuran, tetrahydro-3-furanol, tetrahydrofurfuryl alcohol, 1-(2-furyl)ethanol, furan, dihydrofuran, 2-furan methanol, 2-methyl furan, 2-ethyl furan, 2,5-dimethyl furan, and isomers thereof. The light carboxylic acids may include, without limitation, formic acid, acetic acid, and propionic acid. The volatile oxygenates may also include small amounts of the heavy organic acids, diols, triols, phenols, cresols and other polyols referenced in the following paragraph, to the extent they are volatilized to the vapor phase due to the particular processing conditions, their concentrations within the reaction stream, and azeotropic behavior.

The liquid phase will generally include water and $C_{2+}O_{2+}$ oxygenated hydrocarbons not volatilized to the vapor phase, such as lignin derivatives, disaccharides, monosaccharides, sugars, sugar alcohols, alditols, heavy organic acids, phenols, cresols, and heavy diols, triols and other polyols. As used herein, $C_{2+}O_{2+}$ oxygenated hydrocarbons generally refers to oxygenated hydrocarbons having 2 or more carbon atoms and 2 or more oxygen atoms, and having a relative volatility ($\alpha$) with respect to 1-hexanol of less than 0.03 based on pure components at 250° C. The $C_{2+}O_{2+}$ oxygenated hydrocarbons may also include small amounts of the $C_{2+}O_2$ hydrocarbons, to the extent the $C_{2+}O_2$ hydrocarbons are not volatilized to the vapor phase due to the particular processing conditions, their concentrations within the reaction stream, and azeotropic behavior. Preferably, the $C_{2+}O_{2+}$ oxygenated hydrocarbons have 2 to 6 carbon atoms or 2 to 12 carbon atoms. The $C_{2+}O_{2+}$ oxygenated hydrocarbons may also have 2 or more carbon atoms, 6 or more carbon atoms, 18 or more carbon atoms, or 24 or more carbon atoms, depending on the processing conditions and their concentration in the reaction stream. Exemplary $C_{2+}O_2$ hydrocarbon species that may be present in both the liquid and vapor phases include hydroxyacetone, ethylene glycol, propylene glycol, and organic acids (e.g., acetic acid, propionic acid, lactic acid, etc.).

The $C_{2+}O_{2+}$ oxygenated hydrocarbons will generally be soluble in water and/or a solvent, but may also include compounds that are insoluble in water. In one embodiment, the $C_{2+}O_{2+}$ oxygenated hydrocarbons include sugars, sugar alcohols, sugar degradation products, starch, saccharides and other polyhydric alcohols. Preferably, the $C_{2+}O_{2+}$ oxygenated hydrocarbons include a sugar, such as glucose, fructose, sucrose, maltose, lactose, mannose or xylose, or a sugar alcohol, such as arabitol, erythritol, glycerol, isomalt, lactitol, maltitol, mannitol, sorbitol, xylitol, arabitol, or glycol. In other embodiments, the $C_{2+}O_{2+}$ oxygenated hydrocarbons may also include esters, heavy carboxylic acids, diols and other polyols. The organic acids may include, without limitation, butanoic acid, pentanoic acid, hexanoic acid, heptanoic acid, isomers and derivatives thereof, including hydroxylated derivatives, such as 2-hydroxybutanoic acid and lactic acid. The diols may include, without limitation, ethylene glycol, propylene glycol, 1,3-propanediol, butanediol, pentanediol, hexanediol, heptanediol, octanediol, nonanediol, decanediol, undecanediol, dodecanediol, dihydroxy benzene, catechol, resorcinol, cyclic diols, substitutes thereof, and isomers thereof. The triols may include, without limitation, glycerol, 1,1,1 tris (hydroxymethyl)-ethane (trimethylolethane), trimethylolpropane, hexanetriol, and isomers thereof. Other tri-oxygenates may include, without limitation, tetrahydro-2-furoic acid, hydroxymethyltetrahydrofurfural, hydroxylmethylfurfural, dihydro-5-(hydroxymethyl)-2(3H)-furanone, 5-hydroxymethyl-2(5H)-furanone, dihydro-5-(hydroxymethyl)-2(3H)-furanone, and isomers thereof. The liquid phase may also include volatile oxygenates, including any of the alcohols, ketones, aldehydes, carboxylic acids, ethers and cyclic ethers referenced above, to the extent they are present in the liquid phase.

The solid phase will generally include extractives and unreacted or under-reacted biomass and, in certain applications, the deconstruction catalyst. Extractives will typically include ash components, such as calcium, aluminum, potassium, sodium, magnesium, chloride, sulfates, sulfites, thiols, silica, copper, iron, phosphates, and phosphorous, as well as color bodies (e.g., terpenoids, stilbenes, flavonoids), proteinaceous materials and other inorganic products. The under-reacted biomass will typically include partially reacted biomass, and other heavy lignin, cellulose and hemicellulose derivatives not readily solubilized or maintained in a liquid phase, such as heavy polysaccharides, starches, and other longer chain oxygenated hydrocarbons.

The volatile oxygenates can undergo condensation reactions to form either larger carbon number straight chain compounds, branched chain compounds, or cyclic compounds. The resulting compounds may be hydrocarbons or hydrocarbons containing oxygen, the oxygen of which can be removed through the reaction with hydrogen over a catalyst. The resulting condensed products include $C_{4+}$ alcohols, $C_{4+}$ ketones, $C_{4+}$ alkanes, $C_{4+}$ alkenes, $C_{5+}$ cycloalkanes, $C_{5+}$ cycloalkenes, aryls, fused aryls, and mixtures thereof. The mixtures can be fractionated and/or blended to produce the appropriate mixtures of molecules typically used in gasoline, jet fuel, diesel fuel, or in industrial chemical processes.

Following conversion over the deconstruction catalyst, the product stream undergoes one or more separation steps to separate the vapor, liquid and solid phase components. Various separation techniques are known in the art and may be used. Such techniques may include, without limitation, gravitational settling techniques, cyclone separation techniques, simulated moving bed technology, distillation, filtration, etc. In one embodiment, the reactor system may include an outlet for the capture and removal of the vapor phase, and a second outlet for the collection and removal of the liquid phase and solid phase components. In another embodiment, the product stream can be directed into a phase separator to allow for the simultaneous separation of each phase of the product stream. In either application, the liquid and solid phase can be directed into a settling tank configured to allow a bottom portion containing solid materials (e.g., catalyst, extractives and unreacted or under-reacted materials) to separate from a top liquid phase portion containing a significant fraction of the $C_{2+}O_{2+}$ oxygenated hydrocarbons. In certain embodiments, a portion of the liquid phase may also be maintained in the bottom portion to assist with the movement of the solid materials through additional processing steps or recycled to the biomass feed stream for use as a solvent to aid in biomass deconstruction.

In certain embodiments, the liquid phase may also require further processing to separate aqueous phase products from organic phase products, such as lignin-based hydrocarbons that are not suitable for further conversion. The liquid phase may also be dewatered or further purified prior to being introduced into further processing steps. Such dewatering and purification processes are known in the art and may include techniques such as distillation, filtration, etc.

In one embodiment, the resulting solution of $C_{2+}O_{2+}$ oxygenated hydrocarbons is collected for further processing in a bioreforming process or, alternatively, used as a feedstock for other conversion processes, including the production of fuels and chemicals using fermentation or enzymatic technologies. For example, water-soluble carbohydrates, such as starch, monosaccharides, disaccharides, polysaccharides, sugars, and sugar alcohols, and water-soluble derivatives from the lignin, hemicellulose and cellulose are suitable for use in bioreforming processes, such as those described in U.S. Pat. Nos. 6,699,457; 6,964,757; 6,964,758; and 7,618,612 (all to Cortright et al., and entitled "Low-Temperature Hydrogen Production from Oxygenated Hydrocarbons"); U.S. Pat. No. 6,953,873 (to Cortright et al., and entitled "Low-Temperature Hydrocarbon Production from Oxygenated Hydrocarbons"); U.S. Pat. Nos. 7,767,867; 7,989,664; and U.S. Patent Publication No. 2011/0306804 (to Cortright, and entitled "Methods and Systems for Generating Polyols"); U.S. Pat. Nos. 8,053,615; 8,017,818; 7,977,517; and U.S. Patent Publication Nos. 2011/

0257448; 2011/0245543; 2011/0257416; and 2011/0245542 (all to Cortright and Blommel, and entitled "Synthesis of Liquid Fuels and Chemicals from Oxygenated Hydrocarbons"); U.S. Patent Publication No. 2009/0211942 (to Cortright, and entitled "Catalysts and Methods for Reforming Oxygenated Compounds"); U.S. Patent Publication No. 2010/0076233 (to Cortright et al., and entitled "Synthesis of Liquid Fuels from Biomass"); International Patent Application No. PCT/US2008/056330 (to Cortright and Blommel, and entitled "Synthesis of Liquid Fuels and Chemicals from Oxygenated Hydrocarbons"); and commonly owned co-pending International Patent Application No. PCT/US2006/048030 (to Cortright et al., and entitled "Catalyst and Methods for Reforming Oxygenated Compounds"), all of which are incorporated herein by reference. Alternatively, the liquid phase may be recycled and combined in the biomass feed stream for further conversion.

Biomass Deconstruction

To produce the desired products, the biomass feed stream is reacted with hydrogen over a heterogeneous deconstruction catalyst under conditions of temperature and pressure effective to convert the lignin, cellulose, hemicellulose and their derivatives, whether recycled or reactively generated in the feed stream, to a product stream containing volatile $C_{2+}O_{1-2}$ oxygenates in a gas phase, and a solution of $C_{2+}O_{2+}$ oxygenated hydrocarbons. The specific products produced will depend on various factors including the composition of the feed stream, reaction temperature, reaction pressure, water and/or solvent concentration, hydrogen concentration, the reactivity of the catalyst, and the flow rate of the feed stream as it affects the space velocity (the mass/volume of reactant per unit of catalyst per unit of time), gas hourly space velocity (GHSV), liquid hour space velocity (LHSV), and weight hourly space velocity (WHSV). For example, the vapor phase may also include small amounts of other compounds (e.g., glycerol, heavy organic acids, butane diols, butane triols, etc.) due to the processing conditions and their concentration.

The biomass may be originally provided in its native form, pelletized or reduced to a size appropriate for processing, such as by chopping, shredding, or grinding to a size that allows maximum contact with the deconstruction catalyst or movement through the reactor system. The biomass may also be pretreated or washed in water or a solvent to remove all or a portion of the ash, lignin or any undesired components contained in the biomass or in the biomass stream. The washing may include hot water extraction or any one or more biological, enzymatic or thermochemical processes, such as enzymatic hydrolysis, acid hydrolysis or organosolv type applications.

The deconstruction catalyst is a heterogeneous catalyst having one or more materials capable of catalyzing a reaction between hydrogen and lignin, cellulose, hemicellulose and their derivatives to produce the desired water-soluble oxygenated compounds. The heterogeneous catalyst may include, without limitation, acid modified resins, acid modified supports, base modified resins, base modified supports, tungsten carbides, and/or one or more of Ru, Co, Rh, Pd, Ni, Mo. The catalyst may also include these elements alone or combined with one or more Fe, Ir, Pt, Re, Cu, Mn, Cr, Mo, B, W, V, Nb, Ta, Ti, Zr, Y, La, Sc, Zn, Cd, Ag, Au, Sn, Ge, P, Al, Ga, In, Tl, alloys thereof, and combinations thereof. In one embodiment, the catalyst includes Ru, Co, Rh, Pd, Ni, or Mo and at least one member selected from W, B, Pt, Pd, Sn, Ag, Au, Rh, Co, Re, and Mo.

Resins will generally include basic or acidic supports (e.g., supports having low isoelectric points) that are able to catalyze liquefaction reactions of biomass, followed by hydrogenation reactions in the presence of $H_2$, leading to carbon atoms that are not bonded to oxygen atoms. One class of acidic supports includes heteropolyacids, solid-phase acids exemplified by such species as $H_{3+x}PMo_{12-x}V_xO_{40}$, $H_4SiW_{12}O_{40}$, $H_3PW_{12}O_{40}$, and $H_6P_2W_{18}O_{62}$. Heteropolyacids also have a well-defined local structure, the most common of which is the tungsten-based Keggin structure. Basic resins may include supports that exhibit basic functionality. Examples of acidic and basic resins include the Amberlyst 15Wet, 15Dry, 16Wet, 31Wet, 33, 35Wet, 35Dry, 39Wet, 70, CH10, CH28 resins, Amberlyst A21, A23, A24 and A26 OH resins, and the Amberjet 4200 Cl, Amberlite IRA 400 Cl, Amberlite IRA 410 Cl, Amberlite IRC76, Amberlite IRC747, Amberlite IRC748, Ambersep GT74, Ambersep 820U Cl, resins produced by Rohm Haas.

The catalyst is either self-supporting or includes a supporting material. The support may contain any one or more of nitride, carbon, silica, alumina, acidic alumina, silica-alumina, theta-alumina, sulfated alumina, phosphated alumina, zirconia, sulfated zirconia, phosphate zirconia, titania zirconia, tungstated zirconia, titania, tungsten, vanadia, ceria, zinc oxide, chromia, boron nitride, heteropolyacids, kieselguhr, hydroxyapatite, and mixtures thereof. Nanoporous supports such as zeolites, carbon nanotubes, or carbon fullerene may also be used. Preferable supports are carbon, alumina, phosphate zirconia, m-$ZrO_2$, and W—$ZrO_2$. In one embodiment, the deconstruction catalyst includes Ni:Mo, Pd:Mo, Rh:Mo, Pd:Ag or Co:Mo on a m-$ZrO_2$ support. In another embodiment, the catalyst includes Ru, Ru:Pt, Ru:Pd, Pd:Ag, or Ru:Pt:Sn on a carbon or W—$ZrO_2$ support. The support may also serve as a functional catalyst, such as in the case of acidic or basic resins or supports having acidic or basic functionality.

The deconstruction catalyst may be designed and configured to function as a fixed bed within a reactor or mixed with the feed stream as in a slurry reactor. In one embodiment, the catalyst is formed in a honeycombed monolith design such that the biomass feed stream, whether as a biomass slurry, solid phase slurry, or a solid/liquid phase slurry, can flow through the catalyst. In another embodiment, the catalyst includes a magnetic element, such as Fe or Co, so that the catalyst can be easily separated from the resulting biomass product stream. In yet another embodiment, the deconstruction catalyst is a metal sponge material, such as a sponge nickel catalyst.

Activated sponge nickel catalysts (e.g., Raney nickel) are a well-known class of materials effective for various reactions. The Raney nickel catalyst is typically prepared by treating an alloy of approximately equal amounts by weight of nickel and aluminum with an aqueous alkali solution, e.g., containing about 25 wt. % of sodium hydroxide. The aluminum is selectively dissolved by the aqueous alkali solution leaving particles having a sponge construction and composed predominantly of nickel with a minor amount of aluminum. Promoter metals, such as those described above, may be included in the initial alloy in an amount such that about 1-5 wt. % remains in the sponge nickel catalyst.

The deconstruction process can be either batch or continuous. In one embodiment, the deconstruction process is a continuous process using one or more continuous stirred-tank reactors in parallel or in series. The deconstruction temperature will generally be greater than 120° C., or 150° C., or 185° C., or 200° C., or 250° C., or 270° C., and less than 350° C., or 325° C., or 310° C., or 300° C. In one embodiment, the deconstruction temperature is between about 120° C. and 350° C., or between about 150° C. and 325° C., or between about 200° C. and 310° C., or between about 250° C. and 300° C., or between about 270° C. and 300° C. The deconstruction pressure will generally be greater than 300 psi, or 375 psi, or 475 psi, or 600 psi, or 750 psi, or 1000 psi, and less than 2500 psi, or 2400 psi, or 2150 psi, or 1900 psi, or 1750 psi, or 1500 psi. In one embodiment the deconstruction pressure is between about 300 psi and 2500 psi, or between about 300 psi and 1500 psi, or between about 1000 psi and 1500 psi. In one embodiment, the deconstruction occurs stage-wise such that the deconstruction temperature and deconstruction pressure can be varied in each stage (e.g., a first stage deconstruction temperature and pressure between about 150° C. and 325° C. and between about 300 psi and 1800 psi, respectively, and a second stage deconstruction temperature and pressure between about 200° C. and 300° C. and about 800 psi and 1500 psi, respectively). Collectively, the temperature and pressure conditions should be such that a significant portion of the volatile $C_{2+}O_{1-2}$ oxygenates are in the vapor phase, while a significant portion of the water and less-volatile $C_{2+}O_{2+}$ oxygenates (e.g., heavier di-oxygenates, tri-oxygenates and other polyoxygenates, etc.) and other lignin, hemi-cellulose and cellulose derivatives (e.g., sugars, sugar alcohols, saccharides, starches, etc.) are maintained in the liquid phase and/or solid phase.

In general, the reaction should be conducted under conditions where the residence time of the feed stream over the catalyst is appropriate to generate the volatile $C_{2+}O_{1-2}$ oxygenates in a gas phase. For example, the WHSV for the reaction may be at least about 0.1 gram of biomass per gram of catalyst per hour, and more preferably about 0.1 to 40.0 g/g hr, including a WHSV of about 0.25, 0.5, 0.75, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 11, 12, 13, 14, 15, 20, 25, 30, 35, 40 g/g hr, and ratios between (including 0.83, 0.84, 0.85, 1.71, 1.72, 1.73, etc.). Preferably, the biomass feed stream contacts the catalyst for between approximately 5 minutes and 6 hours.

The present invention is able to effectively convert the biomass components to lower molecular weight oxygenated hydrocarbons due to the presence of hydrogen in the system. The hydrogen facilitates the reaction and conversion process by immediately reacting with the various reaction intermediates and the catalyst to produce products that are more stable and less subject to degradation. The hydrogen may be generated in situ using aqueous phase reforming (in situ generated $H_2$ or APR $H_2$), whether in the biomass deconstruction reactor or in downstream processes using the water-soluble $C_{2+}O_{2+}$ oxygenated hydrocarbons from the liquid phase as a feedstock, or a combination of APR $H_2$, external $H_2$ or recycled $H_2$, or just simply external $H_2$ or recycled $H_2$. The term "external $H_2$" refers to hydrogen that does not originate from the biomass solution, but is added to the reactor system from an external source. The term "recycled $H_2$" refers to unconsumed hydrogen which is collected and then recycled back into the reactor system for further use. External $H_2$ and recycled $H_2$ may also be referred to collectively or individually as "supplemental $H_2$." In general, the amount of $H_2$ added should maintain the reaction pressure within the system at the desired levels, or to increase the molar ratio of hydrogen to carbon and/or oxygen in order to enhance the production yield of certain reaction product types.

The deconstruction process may also include the introduction of supplemental materials to the feed stream to assist with the biomass deconstruction or to increase the yields of the conversion process. Yield increasing supplemental materials may include: unreacted or under-reacted materials recycled from the solid phase of the product stream; $C_{2+}O_{2+}$ oxygenated hydrocarbons from the liquid phase; and/or solvents from downstream or other processes. Supplemental materials may also include conventional feedstock streams (e.g., starches, syrups, carbohydrates, and sugars), which may also be readily converted to the desired volatile $C_{2+}O_{1-2}$ oxygenates or liquid phase products.

Another supplemental material may include a pressurized gas stream (e.g., hydrogen, inert gas, or product gas) that is sparged through the biomass and catalyst during the deconstruction process. Sparging is used to remove desired products from the reactor to prevent unwanted side reactions (e.g., degradation reactions).

Supplemental materials may also include solvents that aid in the deconstruction process. Solvent-based applications are well known in the art. Organosolv processes use organic solvents such as ionic liquids, acetone, ethanol, 4-methyl-2-pentanone, and solvent mixtures, to fractionate lignocellulosic biomass into cellulose, hemicellulose, and lignin streams (Paszner 1984; Muurinen 2000; and Bozell 1998). Strong-acid processes use concentrated hydrochloric acid, phosphoric acid, sulfuric acid or other strong organic acids as the depolymerization agent, while weak acid processes involve the use of dilute strong acids, acetic acid, oxalic acid, hydrofluoric acid, or other weak acids as the solvent. Enzymatic processes have also recently gained prominence and include the use of enzymes as a biocatalyst to decrystalize the structure of the biomass and allow further hydrolysis to useable feedstocks. In one example, the supplemental materials include acetone, gluconic acid, acetic acid, $H_2SO_4$ or $H_3PO_4$. In another example, the supplemental materials include an aqueous solution of water-soluble oxygenated hydrocarbons, and solvents derived from a bioreforming process, such as those described in U.S. Pat. Nos. 7,767,867; 7,989,664; and U.S. Patent Publication No. 2011/0306804 all to Cortright, and entitled "Methods and Systems for Generating Polyols".

Condensation

The volatile $C_{2+}O_{1-2}$ oxygenates produced can be collected and used in industrial applications, or converted into $C_{4+}$ compounds by condensation reactions catalyzed by a condensation catalyst. Without being limited to any specific theories, it is believed that the condensation reactions generally consist of a series of steps involving: (a) the dehydration of oxygenates to alkenes; (b) oligomerization of the alkenes; (c) cracking reactions; (d) cyclization of larger alkenes to form aromatics; (e) alkane isomerization; (f) hydrogen-transfer reactions to form alkanes. The reactions may also consist of a series of steps involving: (1) aldol condensation to form a β-hydroxyketone or β-hydroxyaldehyde; (2) dehydration of the β-hydroxyketone or β-hydroxyaldehyde to form a conjugated enone; (3) hydrogenation of the conjugated enone to form a ketone or aldehyde, which may participate in further condensation reactions or conversion to an alcohol or hydrocarbon; and (4) hydrogenation of carbonyls to alcohols, or vice-versa. Other condensation reactions may occur in parallel, including aldol condensation, prins reactions, ketonization of acids, and Diels-Alder condensation.

The condensation catalyst will generally be a catalyst capable of forming longer chain compounds by linking two oxygen containing species through a new carbon-carbon bond, and converting the resulting compound to a hydrocarbon, alcohol or ketone. The condensation catalyst may include, without limitation, carbides, nitrides, zirconia, alumina, silica, aluminosilicates, phosphates, zeolites, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and combinations thereof. The condensation catalyst may include the above alone or in combination with a modifier, such as Ce, La, Y, Sc, P, B, Bi, Li, Na, K, Rb, Cs, Mg, Ca, Sr, Ba, and combinations thereof. The condensation catalyst may also include a metal, such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, to provide a metal functionality.

The condensation catalyst may be self-supporting (i.e., the catalyst does not need another material to serve as a support), or may require a separate support suitable for suspending the catalyst in the reactant stream. Particularly beneficial supports include alumina, silica, and zirconia. In other embodiments, particularly when the condensation catalyst is a powder, the catalyst system may include a binder to assist in forming the catalyst into a desirable catalyst shape. Applicable forming processes include extrusion, pelletization, oil dropping, or other known processes. Zinc oxide, alumina, and a peptizing agent may also be mixed together and extruded to produce a formed material. After drying, this material is calcined at a temperature appropriate for formation of the catalytically active phase, which usually requires temperatures in excess of 350° C. Other catalyst supports may include those described in further detail below.

In one embodiment, the condensation reaction is performed using a catalyst having acidic functionality. The acid catalysts may include, without limitation, aluminosilicates (zeolites), silica-alumina phosphates (SAPO), aluminum phosphates (ALPO), amorphous silica alumina, zirconia, sulfated zirconia, tungstated zirconia, tungsten carbide, molybdenum carbide, titania, acidic alumina, phosphated alumina, phosphated silica, sulfated carbons, phosphated carbons, acidic resins, heteropolyacids, inorganic acids, and combinations thereof. In one embodiment, the catalyst may also include a modifier, such as Ce, La, Y, Li, Na, K, Rb, Cs, Mg, Ca, Sr, Ba, P, B, Bi, and combinations thereof. The catalyst may also be modified by the addition of a metal, such as Cu, Ag, Au, Pt, Ni, Fe, Co, Ru, Rh, Zn, Ga, In, Pd, Ir, Re, Mn, Cr, Mo, W, Sn, Os, alloys and combinations thereof, to provide metal functionality, and/or sulfides and oxides of Ti, Zr, V, Nb, Ta, Mo, Cr, W, Mn, Re, Al, Ga, In, Fe, Co, Ir, Ni, Si, Cu, Zn, Sn, P, and combinations thereof. Tungstated zirconia has been found to be a particularly useful catalyst for the present process, especially when modified with Cu, Pd, Ag, Pt, Ru, Ni, Sn and combinations thereof. The acid catalyst may be homogenous, self-supporting or adhered to any one of the supports further described below, including supports containing carbon, silica, alumina, zirconia, titania, vanadia, ceria, heteropolyacids, alloys and mixtures thereof.

For example, the condensation catalyst may be a zeolite catalyst. The term "zeolite" as used herein refers not only to microporous crystalline aluminosilicate, but also microporous crystalline metal-containing aluminosilicate structures, such as galloaluminosilicates and gallosilicates. In such instances, In, Zn, Fe, Mo, Ag, Au, Ni, P, Y, Ta, and lanthanides may be exchanged onto zeolites to provide the desired activity. Metal functionality may be provided by metals such as Cu, Ag, Au, Pt, Ni, Fe, Co, Ru, Zn, In, Rh, Pd, Ir, Re, Mn, Cr, Mo, W, Sn, Os, alloys and combinations thereof.

Examples of suitable zeolite catalysts include ZSM-5, ZSM-11, ZSM-12, ZSM-22, ZSM-23, ZSM-35 and ZSM-48. Zeolite ZSM-5, and the conventional preparation thereof, is described in U.S. Pat. No. 3,702,886; Re. 29,948 (highly siliceous ZSM-5); U.S. Pat. Nos. 4,100,262 and 4,139,600, all incorporated herein by reference. Zeolite ZSM-11, and the conventional preparation thereof, is described in U.S. Pat. No. 3,709,979, which is also incorporated herein by reference. Zeolite ZSM-12, and the conventional preparation thereof, is described in U.S. Pat. No. 3,832,449, incorporated herein by reference. Zeolite ZSM-23, and the conventional preparation thereof, is described in U.S. Pat. No. 4,076,842, incorporated herein by reference. Zeolite ZSM-35, and the conventional preparation thereof, is described in U.S. Pat. No. 4,016,245, incorporated herein by reference. Another preparation of ZSM-35 is described in U.S. Pat. No. 4,107,195, the disclosure of which is incorporated herein by reference. ZSM-48, and the conventional preparation thereof, is taught by U.S. Pat. No. 4,375,573, incorporated herein by reference. Other examples of zeolite catalysts are described in U.S. Pat. No. 5,019,663 and U.S. Pat. No. 7,022,888, also incorporated herein by reference. In one embodiment, the condensation catalyst is a ZSM-5 zeolite modified with Cu, Pd, Ag, Pt, Ru, Ni, Sn, or combinations thereof.

As described in U.S. Pat. No. 7,022,888, the condensation catalyst may be a bifunctional pentasil zeolite catalyst including at least one metallic element from the group of Cu, Ag, Au, Pt, Ni, Fe, Co, Ru, Zn, Cd, In, Rh, Pd, Ir, Re, Mn, Cr, Mo, W, Sn, Os, alloys and combinations thereof, or a modifier from the group of In, Zn, Fe, Mo, Au, Ag, Y, Sc, Ni, P, Ta, lanthanides, and combinations thereof. The zeolite preferably has strong acidic sites, and may be used with reactant streams containing and an oxygenated hydrocarbon at a temperature of below 580° C. The bifunctional pentasil zeolite may have ZSM-5, ZSM-8 or ZSM-11 type crystal structure consisting of a large number of 5-membered oxygen-rings (i.e., pentasil rings). The zeolite with ZSM-5 type structure is a particularly preferred catalyst.

The condensation catalyst may include one or more zeolite structures comprising cage-like structures of silica-alumina. Zeolites are crystalline microporous materials with well-defined pore structures. Zeolites contain active sites, usually acid sites, which can be generated in the zeolite framework. The strength and concentration of the active sites can be tailored for particular applications. Examples of suitable zeolites for condensing secondary alcohols and alkanes may comprise aluminosilicates, optionally modified with cations, such as Ga, In, Zn, Mo, and mixtures of such cations, as described, for example, in U.S. Pat. No. 3,702,886, which is incorporated herein by reference. As recognized in the art, the structure of the particular zeolite or zeolites may be altered to provide different amounts of various hydrocarbon species in the product mixture. Depending on the structure of the zeolite catalyst, the product mixture may contain various amounts of aromatic and cyclic hydrocarbons.

Alternatively, solid acid catalysts such as alumina modified with phosphates, chloride, silica, and other acidic oxides could be used in practicing the present invention. Also, sulfated zirconia, phosphated zirconia, titania zirconia, or tungstated zirconia may provide the necessary acidity. Re and Pt/Re catalysts are also useful for promoting condensation of oxygenates to $C_{5+}$ hydrocarbons and/or $C_{5+}$ mono-oxygenates. The Re is sufficiently acidic to promote acid-catalyzed condensation. Acidity may also be added to activated carbon by the addition of either sulfates or phosphates.

The specific $C_{4+}$ compounds produced will depend on various factors, including, without limitation, the type of volatile $C_{2+}O_{1-2}$ oxygenates in the reactant stream, condensation temperature, condensation pressure, the reactivity of the catalyst, and the flow rate of the reactant stream as it affects the space velocity, GHSV, LHSV, and WHSV. Preferably, the reactant stream is contacted with the condensation catalyst at a WHSV that is appropriate to produce the desired hydrocarbon products. The WHSV is preferably at least about 0.1 grams of volatile $C_{2+}O_{1-2}$ oxygenates in the reactant stream per gram catalyst per hour, more preferably the WHSV is between about 0.1 to 10.0 g/g hr, including a WHSV of about 1, 2, 3, 4, 5, 6, 7, 8, 9, 10 g/g hr, and increments between.

The condensation reaction should be carried out at a temperature and pressure at which the thermodynamics of the proposed reaction are favorable. In general, the reaction should be carried out at a temperature where the vapor pressure of the volatile $C_{2+}O_{1-2}$ oxygenates is at least about 0.1 atm (and preferably a good deal higher). The condensation temperature will vary depending upon the specific composition of the volatile $C_{2+}O_{1-2}$ oxygenates. The condensation temperature will generally be greater than 80° C., or 125° C., or 175° C., or 200° C., or 225° C., or 250° C., and less than 500° C., or 450° C., or 425° C., or 375° C., or 325° C., or 275° C. In one embodiment, the condensation temperature is between about 80° C. to 500° C., or between about 125° C. to 450° C., or between about 250° C. to 425° C. The condensation pressure will generally be greater than 0 psig, or 10 psig, or 100 psig, or 200 psig, and less than 1200 psig, or 1100 psig, or 1000 psig, or 900 psig, or 700 psig. In one embodiment, the condensation pressure is greater than about 0.1 atm, or between about 0 and 1200 psig, or between about 0 and 1000 psig.

Varying the factors above, as well as others, will generally result in a modification to the specific composition and yields of the $C_{4+}$ compounds. For example, varying the temperature and/or pressure of the reactor system, or the particular catalyst formulations, may result in the production of $C_{4+}$ alcohols and/or ketones instead of $C_{4+}$ hydrocarbons. The $C_{4+}$ hydrocarbon product may also contain a variety of alkenes, and alkanes of various sizes (including both normal and branched alkanes). Depending upon the condensation catalyst used, the hydrocarbon product may also include aromatic and cyclic hydrocarbon compounds. The $C_{4+}$ hydrocarbon product may also contain undesirably high levels of alkenes, which may lead to coking or deposits in combustion engines, or other undesirable hydrocarbon products. In such an event, the hydrocarbon molecules produced may be optionally hydrogenated to reduce the ketones to alcohols and hydrocarbons, while the alcohols and unsaturated hydrocarbon may be reduced to alkanes, cyclic alkanes, and aromatics, thereby forming a more desirable hydrocarbon product having low levels of alkenes, aromatics or alcohols.

The finishing step will generally involve a hydrogenation reaction that removes the remaining oxygen from the hydrocarbons, including removing oxygen from carbonyls, hydroxyls, furans, acids, esters, phenols. Various processes and catalysts are known for hydrogenating oxygenated compounds. Typical catalysts include a support with any one or more of the following metals, Cu, Ni, Fe, Co, Ru, Pd, Rh, Pt, Ir, Os, alloys or combinations thereof, alone or with promoters such as Au, Ag, Cr, Zn, Mn, Sn, Cu, Bi, and alloys thereof. The above metals and promoters may be used in various loadings ranging from about 0.01 to about 20 wt % on any one of the supports described below.

In general, the finishing step is carried out at finishing temperatures of between about 200° C. to 450° C., and finishing pressures in the range of about 100 psig to 2000 psig. The finishing step may be conducted in the vapor phase or liquid phase, and may use in situ generated $H_2$, external $H_2$, recycled $H_2$, or combinations thereof, as necessary.

Other factors, such as the presence of water or undesired oxygenates, may also effect the composition and yields of the $C_{4+}$ compounds, as well as the activity and stability of the condensation catalyst. In such event, the process may include a dewatering step that removes a portion of the water prior to condensation, or a separation unit for removal of the undesired oxygenates. For instance, a separator unit, such as a phase separator, flash separator, extractor, purifier or distillation column, may be installed prior to the condensation step so as to remove a portion of the water from the reactant stream containing the volatile $C_{2+}O_{1-2}$ oxygenates. A separation unit may also be installed to remove specific oxygenates to allow for the production of a desired product stream containing hydrocarbons within a particular carbon range, or for use as end products or in other systems or processes.

The effectiveness of the condensation catalyst may also be influenced by the presence of small amounts of heavier di-oxygenates and tri-oxygenates volatilized into the gas phase due to the processing conditions and their concentration in the reaction stream. Such compounds typically have a relative volatility (a) with respect to 1-hexanol of lower than 0.03 based on pure components at 250° C., but may be volatilized at minimal concentrations, lower pressures and higher temperatures during deconstruction reactions. They are also known to lead to coking and rapid deactivation of catalysts in condensation-type reactions. One advantage of the present invention is that such compounds are minimized in the reaction stream and, to the extent present, the process conditions and catalysts employed for the condensation reactions allows for their conversion to useable end products without significant coking and/or deactivation of the condensation catalyst.

$C_{4+}$ Compounds

The practice of the present invention results in the production of $C_{4+}$ alkanes, $C_{4+}$ alkenes, $C_{5+}$ cycloalkanes, $C_{5+}$ cycloalkenes, aryls, fused aryls, $C_{4+}$ alcohols, $C_{4+}$ ketones, $C_{4+}$ furans and mixtures thereof. The $C_{4+}$ alkanes and $C_{4+}$ alkenes have from 4 to 30 carbon atoms ($C_{4-30}$ alkanes and $C_{4-30}$ alkenes) and may be branched or straight chained alkanes or alkenes. The $C_{4+}$ alkanes and $C_{4+}$ alkenes may also include fractions of $C_{4-9}$, $C_{7-14}$, $C_{12-24}$ alkanes and alkenes, respectively, with the $C_{4-9}$ fraction directed to gasoline, the $C_{7-16}$ fraction directed to jet fuels, and the $C_{11-24}$ fraction directed to diesel fuel and other industrial applications. Examples of various $C_{4+}$ alkanes and $C_{4+}$ alkenes include, without limitation, butane, butene, pentane, pentene, 2-methylbutane, hexane, hexene, 2-methylpentane, 3-methylpentane, 2,2-dimethylbutane, 2,3-dimethylbutane, heptane, heptene, octane, octene, 2,2,4,-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, hexadecane, hexadecene, heptyldecane, heptyldecene, octyldecane, octyldecene, nonyldecane, nonyldecene, eicosane, eicosene, uneicosane, uneicosene, doeicosane, doeicosene, trieicosane, trieicosene, tetraeicosane, tetraeicosene, and isomers thereof.

The $C_{5+}$ cycloalkanes and $C_{5+}$ cycloalkenes have from 5 to 30 carbon atoms and may be unsubstituted, mono-substituted or multi-substituted. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. In one embodiment, at least one of the substituted groups include a branched $C_{3-12}$ alkyl, a straight chain $C_{1-12}$ alkyl, a branched $C_{3-12}$ alkylene, a straight chain $C_{1-12}$ alkylene, a straight chain $C_{2-12}$ alkylene, a phenyl or a combination thereof. In yet another embodiment, at least one of the substituted groups include a branched $C_{3-4}$ alkyl, a straight chain $C_{1-4}$ alkyl, a branched $C_{3-4}$ alkylene, straight chain $C_{1-4}$ alkylene, straight chain $C_{2-4}$ alkylene, a phenyl or a combination thereof. Examples of desirable $C_{5+}$ cycloalkanes and $C_{5+}$ cycloalkenes include, without limitation, cyclopentane, cyclopentene, cyclohexane, cyclohexene, methyl-cyclopentane, methyl-cyclopentene, ethyl-cyclopentane, ethyl-cyclopentene, ethyl-cyclohexane, ethyl-cyclohexene, propyl-cyclohexane, butyl-cyclopentane, butyl-cyclohexane, pentyl-cyclopentane, pentyl-cyclohexane, hexyl-cyclopentane, hexyl-cyclohexane, and isomers thereof.

Aryls will generally consist of an aromatic hydrocarbon in either an unsubstituted (phenyl), mono-substituted or multi-substituted form. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. In one embodiment, at least one of the substituted groups include a branched $C_{3-12}$ alkyl, a straight chain $C_{1-12}$ alkyl, a branched $C_{3-12}$ alkylene, a straight chain $C_{2-12}$ alkylene, a phenyl or a combination thereof. In yet another embodiment, at least one of the substituted groups include a branched $C_{3-4}$ alkyl, a straight chain $C_{1-4}$ alkyl, a branched $C_{3-4}$ alkylene, straight chain $C_{2-4}$ alkylene, a phenyl or a combination thereof. Examples of various aryls include, without limitation, benzene, toluene, xylene (dimethylbenzene), ethyl benzene, para xylene, meta xylene, ortho xylene, $C_{9+}$ aromatics, butyl benzene, pentyl benzene, hexyl benzene, heptyl benzene, oxtyl benzene, nonyl benzene, decyl benzene, undecyl benzene, and isomers thereof.

Fused aryls will generally consist of bicyclic and polycyclic aromatic hydrocarbons, in either an unsubstituted, mono-substituted, or multi-substituted form. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. In another embodiment, at least one of the substituted groups include a branched $C_{3-4}$ alkyl, a straight chain $C_{1-4}$ alkyl, a branched $C_{3-4}$ alkylene, straight chain $C_{2-4}$ alkylene, a phenyl or a combination thereof. Examples of various fused aryls include, without limitation, naphthalene, anthracene, tetrahydronaphthalene, and decahydronaphthalene, indane, indene, and isomers thereof.

The $C_{4+}$ alcohols may also be cyclic, branched or straight chained, and have from 4 to 30 carbon atoms. In general, the $C_{4+}$ alcohols may be a compound according to the formula $R^1$—OH, wherein $R^1$ is a member selected from the group consisting of a branched $C_{4+}$ alkyl, straight chain $C_{4+}$ alkyl, a branched $C_{4+}$ alkylene, a straight chain $C_{4+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl and combinations thereof. Examples of desirable $C_{4+}$ alcohols include, without limitation, butanol, pentanol, hexanol, heptanol, octanol, nonanol, decanol, undecanol, dodecanol, tridecanol, tetradecanol, pentadecanol, hexadecanol, heptyldecanol, octyldecanol, nonyldecanol, eicosanol, uneicosanol, doeicosanol, trieicosanol, tetraeicosanol, and isomers thereof.

The $C_{4+}$ ketones may also be cyclic, branched or straight chained, and have from 4 to 30 carbon atoms. In general, the $C_{4+}$ ketone may be a compound according to the formula

wherein $R^3$ and $R^4$ are independently a member selected from the group consisting of a branched $C_{3+}$ alkyl, a straight chain $C_{1+}$ alkyl, a branched $C_{3+}$ alkylene, a straight chain $C_{2+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl and a combination thereof. Examples of desirable $C_{4+}$ ketones include, without limitation, butanone, pentanone, hexanone, heptanone, octanone, nonanone, decanone, undecanone, dodecanone, tridecanone, tetradecanone, pentadecanone, hexadecanone, heptyldecanone, octyldecanone, nonyldecanone, eicosanone, uneicosanone, doeicosanone, trieicosanone, tetraeicosanone, and isomers thereof.

The lighter fractions of the above, primarily $C_4$-$C_{12}$, may be separated for gasoline use. Moderate fractions, such as $C_7$-$C_{16}$, may be separated for jet fuel, while heavier fractions, i.e., $C_{11}$-$C_{24}$, may be separated for diesel use. The heaviest fractions may be used as lubricants or cracked to produce additional gasoline and/or diesel fractions. The $C_{4+}$ compounds may also find use as industrial chemicals, whether as an intermediate or an end product. For example, the aryls toluene, xylene, ethyl benzene, para xylene, meta xylene, ortho xylene may find use a chemical intermediates for the product of plastics and other products. Meanwhile, the $C_{9+}$ aromatics and fused aryls, such as naphthalene, anthracene, tetrahydronaphthalene, and decahydronaphthalene, may find use as solvents in industrial processes.

Catalyst Supports

In various embodiments above, the catalyst systems include a support suitable for suspending the catalyst in the biomass feed stream, biomass slurry, or reactant stream. The support should be one that provides a stable platform for the chosen catalyst and the reaction conditions. The support may take any form which is stable at the chosen reaction conditions to function at the desired levels, and specifically stable in aqueous feedstock solutions. Such supports include, without limitation, carbon, silica, alumina, silica-alumina, acidic alumina, sulfated alumina, phosphated alumina, zirconia, tungstate zirconia, titania zirconia, sulfated zirconia, phosphated zirconia, titania, ceria, vanadia, nitride, boron nitride, heteropolyacids, hydroxyapatite, zinc oxide, chromia, and mixtures thereof. Nanoporous supports such as zeolites, carbon nanotubes, or carbon fullerene may also be used.

One particularly preferred catalyst support is carbon, especially carbon supports having relatively high surface areas (greater than 100 square meters per gram). Such carbons include activated carbon (granulated, powdered, or pelletized), activated carbon cloth, felts, or fibers, carbon nanotubes or nanohorns, carbon fullerene, high surface area carbon honeycombs, carbon foams (reticulated carbon foams), and carbon blocks. The carbon may be produced via either chemical or steam activation of peat, wood, lignite, coal, coconut shells, olive pits, and oil-based carbon. Another preferred support is granulated activated carbon produced from coconuts.

Another preferred catalyst support is zirconia. The zirconia may be produced via precipitation of zirconium hydroxide from zirconium salts, through sol-gel processing, or any other method. The zirconia is preferably present in a crystalline form achieved through calcination of the precursor material at temperatures exceeding 400° C. and may include both tetragonal and monoclinic crystalline phases. A modifying agent may be added to improve the textural or catalytic properties of the zirconia. Such modifying agents include, without limitation, sulfate, tungstenate, phosphate, titania, silica, and oxides of Group IIIB metals, especially Ce, La, or Y. In one embodiment, the deconstruction catalyst consists of Pd:Ag on a tungstated zirconia support.

Another preferred catalyst support is titania. The titania may be produced via precipitation from titanium salts, through sol-gel processing, or any other method. The titania is preferably present in a crystalline form and may include both anatase and rutile crystalline phases. A modifying agent may be added to improve the textural or catalytic properties of the titania. Such modifying agents include, without limitation, sulfate, silica, and oxides of Group IIIB metals, especially Ce, La, or Y.

Yet another preferred catalyst support is a transitional alumina, preferentially theta alumina. The theta alumina may be produced via precipitation from aluminum salts, through sol-gel processing, or any other method. Preferably, the support would be manufactured through peptization of a suitable aluminum hydroxide, preferentially bohemite or pseudo-bohemite, with nitric acid in the presence of an organic binder, preferentially hydroxyethyl cellulose. After forming the support must then be calcined to a final temperature between 900-1200° C., preferentially greater than 1000° C. A modifying agent may be added to improve the textural or catalytic properties of the alumina. Such modifying agents include, without limitation, sulfate, silica, Fe, Ce, La, Cu, Co, Mo, or W.

The support may also be treated or modified to enhance its properties. For example, the support may be treated, as by surface-modification, to modify surface moieties, such as hydrogen and hydroxyl. Surface hydrogen and hydroxyl groups can cause local pH variations that affect catalytic efficiency. The support may also be modified, for example, by treating it with sulfates, phosphates, tungstenates, silanes, lanthanides, alkali compounds or alkali earth compounds. For carbon supports, the carbon may be pretreated with steam, oxygen (from air), inorganic acids or hydrogen peroxide to provide more surface oxygen sites. The preferred pretreatment would be to use either oxygen or hydrogen peroxide. The pretreated carbon may also be modified by the addition of oxides of Group IVB and Group VB. It is preferred to use oxides of W, Ti, V, Zr and mixtures thereof.

The catalyst systems, whether alone or mixed together, may be prepared using conventional methods known to those in the art. Such methods include incipient wetting, evaporative impregnation, chemical vapor deposition, wash-coating, magnetron sputtering techniques, and the like. The method chosen to fabricate the catalyst is not particularly critical to the function of the invention, with the proviso that different catalysts will yield different results, depending upon considerations such as overall surface area, porosity, etc.

Catalyst Regeneration

During deconstruction, carbonaceous deposits build up on the deconstruction catalyst surface through minor side reactions of the biomass and other generated products. As these deposits accumulate, access to the catalytic sites on the surface becomes restricted and the catalyst performance declines, resulting in lower conversion and yields to desired products.

To regenerate the deconstruction catalyst, the solid phase is further apportioned by separating the catalyst from the extractives and unreacted or under-reacted materials using a washing medium. The washing medium can be any medium capable of washing unreacted species from the catalyst and reactor system. Such washing medium may include any one of several liquid media, such as water, alcohols, ketones, chelating agents, acids, or other oxygenated hydrocarbons, whether alone or in combination with any of the foregoing, and which does not include materials known to be poisons for the catalyst in use (e.g., sulfur). The washing step may include either soaking the catalyst for a period of time (e.g., 5 or more minutes), flushing with the washing medium, or a combination of both, and at a temperature that does not cause the liquid washing medium or the unreacted species to change to the gaseous phase. The washing step may also involve multiple flushing activities, including one or more initial washes with an organic solvent, followed by one or more washes with water, or vice-versa, until the deconstruction catalyst is free of extractives and other unwanted materials. In one embodiment, the temperature is maintained below about 100° C. during the washing step.

In certain applications, the deconstruction catalyst may still be in a mixture with unreacted and under-reacted biomass after washing, thereby requiring additional separation. In general, the deconstruction catalyst will tend to be more dense than the biomass and can be readily separated using various techniques, including cyclone separation, centrifugation, and gravitational settling, among others.

The deconstruction catalyst is then dried at a temperature and pressure sufficient to remove any water from the catalyst (e.g., 120° C. and at atmospheric pressure). Once dried, the temperature in the reactor is increased at a rate of about 20° C. per hour to about 60° C. per hour, and is maintained at a temperature between about 300° C. and about 450° C. At temperatures between about 120° C. and about 150° C., C—O and C—C linkages in the carbonaceous deposits are broken and $CO_2$ and CO are released from the catalyst and collected in a downstream phase separator or removed in the gas phase. As temperatures continue to rise toward about 450° C., C—C bond hydrogenolysis predominates. Throughout the regeneration and cooling process, a gas flow of 600-1200 ml gas/ml catalyst per hour (GHSV) of inert gas (e.g., nitrogen) and 0.5-10% oxygen is maintained.

During the deconstruction catalyst regeneration, carbon dioxide and small amounts of carbon monoxide are emitted as a regeneration stream. Ultimately, the level of carbon dioxide in the regeneration stream declines as the regeneration progresses, providing an effective means for monitoring the status of the regeneration. Based on this trend, to obtain a maximum return of performance, the regeneration is continued until the $CO_2$ content of the regeneration stream is below an amount indicative of successful regeneration.

The deconstruction catalyst is considered completely regenerated when sufficient carbonaceous deposits have been removed such that deconstruction can be resumed. This generally occurs when the $CO_2$ given off during the regeneration decreases to an insignificant amount. In a preferred embodiment, the deconstruction catalyst is considered regenerated when the amount of $CO_2$ in the regeneration stream is less than 4,000 ppm, more preferably less than 2,000 ppm, and most preferably less than 1,000 ppm. To ensure that maximum regeneration is achieved, the deconstruction catalyst may need to be regenerated at its highest temperature for a period of up to 16 hours.

The accumulation of $CO_2$ during regeneration can be utilized to calculate the total grams of carbon removed per gram of catalyst. When the regeneration is run to maximize system performance, the amount of carbon per gram of catalyst can be utilized to determine average rate of deposit for carbonaceous species as well as provide some predictive information on the duration between regenerations assuming similar operating conditions are used.

Alternatively, reductive regeneration can be used to remove the carbon-containing species from the catalyst surface. Reductive catalyst regeneration can be accomplished by heating the catalyst in the presence of hydrogen resulting in the production of alkanes (e.g., $CH_4$, $C_2H_6$, $C_3H_8$, $C_4H_{10}$, $C_5H_{12}$, $C_6H_{14}$, etc.). Similar to the oxidative regeneration described above, measuring the amount of alkanes emitted is an effective means for monitoring the regeneration status.

Extractives

In addition to lignin, cellulose and hemicellulose, biomass includes include ash components, such as calcium, aluminum, potassium, sodium, magnesium, chloride, sulfates, sulfites, thiols, silica, copper, iron, phosphates, and phosphorous, as well as color bodies (e.g., terpenoids, stilbenes, flavonoids), proteinaceous materials and other inorganic products not amenable to downstream conversion processes as those contemplated herein. In practicing the present invention, such materials, as well as unreacted or under reacted lignin, cellulose and hemicellulose, will often be present in the product stream as a solid material and removed as part of the catalytic washing process. Ultimately, the lignin, ash and other extractives can be purged from the system and used in other processes. For example, the lignin can be burned to provide process heat, while the proteinaceous material can be used for animal feed or as other products. The unreacted or under-reacted cellulose and hemicellulose can be recycled to the biomass feed stream and processed until fully reacted.

Liquid Fuels and Chemicals

The $C_{4+}$ compounds derived from the practice of the present invention as described above can be fractionated and used in liquid fuels, such as gasoline, jet fuel (kerosene) or diesel fuel. The $C_{4+}$ compounds can also be fractionated and used in chemical processes, such as those common to the petro-chemical industry. For example, the product stream from the present invention can be fractionated to collect xylenes for use in the production of phthalic acid, polyethylene terephthalate (PET), and ultimately renewable plastics or solvents. Benzene can also be collected and processed for the production of renewable polystyrenes, polycarbonates, polyurethane, epoxy resins, phenolic resins, and nylon. Toluene can be collected and processed for the production of toluene diisocyanate, and ultimately renewable solvents, polyurethane foam or TNT, among others.

In one embodiment, the $C_{4+}$ compounds derived from the practice of the present invention are separated into various distillation fractions by any means known for liquid fuel compositions. In such applications, the product stream having at least one $C_{4+}$ compound derived from the process as described above is preferably separated into more than one distillation fraction, wherein at least one of the distillation fractions is a lighter, moderate or heavier fraction. The lighter fractions, primarily $C_4$-$C_9$, i.e., $C_4$, $C_5$, $C_6$, $C_7$, $C_8$, and $C_9$, may be separated for gasoline use. The moderate fractions, primarily $C_7$-$C_{14}$, i.e., $C_7$, $C_8$, $C_9$, $C_{10}$, $C_{11}$, $C_{12}$, $C_{13}$, and $C_{14}$, may be separated for use as kerosene, e.g., for jet fuel use. Heavier fractions, primarily $C_{12}$-$C_{24}$, i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, and $C_{24}$, may be separated for diesel fuel use. The heaviest fractions, $C_{25+}$ and $C_{30+}$, i.e., $C_{25}$, $C_{26}$, $C_{27}$, $C_{28}$, $C_{29}$, $C_{30}$, $C_{31}$, $C_{32}$, $C_{33}$, $C_{34}$, $C_{35}$, etc., may be used as lubricants, fuel oils, or may be cracked to produce additional fractions for use in gasoline, kerosene and/or diesel fractions.

Because the $C_{4+}$ compounds are derived from biomass, the age of the compounds, or fractions containing the compounds, is less than 100 years old, preferably less than 40 years old, more preferably less than 20 years old, as calculated from the carbon 14 concentration of the component.

The lighter fractions having at least one biomass-derived $C_{4+}$ compounds has one or more of the following properties (LF-i to LF-vi):
- (LF-i) a final boiling point in the range of from 150 to 220° C., more preferably in the range of from 160 to 210° C.;
- (LF-ii) a density at 15° C. in the range of from 700 to 890 kg/m$^3$, more preferably in the range of from 720 to 800 kg/m$^3$;
- (LF-iii) a sulfur content of at most 5 mg/kg, more preferably at most 1 mg/kg;
- (LF-iv) an oxygen content of at most 3.5% wt., more preferably at most 3.0% wt., typically at most 2.7% wt., and more typically at most 0.5%;
- (LF-v) a RON in the range of from 80 to 110, more preferably in the range of from 90 to 100;
- (LF-vi) a MON in the range of from 70 to 100, more preferably in the range of from 80 to 90.

In such instance, the lighter fraction has properties which accord each of the properties detailed in LF-i to LF-vi above, more conveniently with each of the preferred values for each of the properties detailed in LF-i to LF-vi above.

The moderate fractions having at least one biomass-derived $C_{4+}$ compound has one or more of the following properties (MF-i to MF-vix):
- (MF-i) an initial boiling point in the range of from 120 to 215° C., more preferably in the range of from 130 to 205° C.;
- (MF-ii) a final boiling point in the range of from 220 to 320° C., more preferably in the range of from 230 to 300° C.;
- (MF-iii) a density at 15° C. in the range of from 700 to 890 kg/m$^3$, more preferably in the range of from 730 to 840 kg/m$^3$;
- (MF-iv) a sulfur content of at most 0.1% wt., more preferably at most 0.01% wt.;

(MF-v) a total aromatics content of at most 30% vol., more preferably at most 25% vol., even more preferably at most 20% vol., most preferably at most 15% vol.;

(MF-vi) a freeze point of −40° C. or lower, more preferably at least −47° C. or lower;

(MF-vii) a smoke point of at least 18 mm, more preferably at least 19 mm, even more preferably at least 25 mm;

(MF-viii) a viscosity at −20° C. in the range of from 1 to 10 cSt, more preferably in the range of from 2 to 8 cSt.;

(MF-vix) a specific energy content in the range of from 40 to 47 MJ/kg, more preferably in the range of from 42 to 46 MJ/kg.

In such instance, the moderate fraction has properties which accord each of the properties detailed in MF-i to MF-vix above, more conveniently with each of the preferred values for each of the properties detailed in MF-i to MF-vix above.

The heavier fraction having at least one biomass-derived $C_{4+}$ compound has one or more of the following properties (HF-i to HF-vi):

(HF-i) a T95 in the range of from 220 to 380° C., more preferably in the range of from 260 to 360° C.;

(HF-ii) a flash point in the range of from 30 to 70° C., more preferably in the range of from 33 to 60° C.;

(HF-iii) a density at 15° C. in the range of from 700 to 900 kg/m$^3$, more preferably in the range of from 750 to 850 kg/m$^3$;

(HF-iv) a sulfur content of at most 5 mg/kg, more preferably at most 1 mg/kg;

(HF-v) an oxygen content of at most 10% wt., more preferably at most 8% wt.;

(HF-vi) a viscosity at 40° C. in the range of from 0.5 to 6 cSt, more preferably in the range of from 1 to 5 cSt.

In this instance, the heavier fraction has properties which accord each of the properties detailed in HF-i to HF-vi above, more conveniently with each of the preferred values for each of the properties detailed in HF-i to HF-vi above.

In liquid fuels applications, the fraction may be used as a neat fuel product or used as a biomass-derived blending component for a final liquid fuel composition. Accordingly, the present invention includes a liquid fuel composition containing one or more of the lighter fractions, moderate fractions or heavy fractions described above, as a biomass-derived blending component.

The volume of the biomass-derived blending component in the liquid fuel composition should be at least 0.1% vol., based on the overall volume of the liquid fuel composition. For example, the amount of the biomass-derived blending component present in the liquid fuel composition should accord with one or more of the parameters (i) to (xx) listed below:

(i) at least 0.5% vol.
(ii) at least 1% vol
(iii) at least 1.5% vol
(iv) at least 2% vol
(v) at least 2.5% vol
(vi) at least 3% vol
(vii) at least 3.5% vol
(viii) at least 4% vol
(ix) at least 4.5% vol
(x) at least 5% vol
(xi) at most 99.5% vol.
(xii) at most 99% vol.
(xiii) at most 98% vol.
(xiv) at most 97% vol.
(xv) at most 96% vol.
(xvi) at most 95% vol.
(xvii) at most 90% vol.
(xviii) at most 85% vol.
(xix) at most 80% vol.
(xx) at most 75% vol.

The amount of the biomass-derived blending component present in the liquid fuel composition of the present invention accords with one parameter selected from (i) to (x) above, and one parameter selected from (xi) to (xx) above.

For gasoline compositions according to the present invention, the amount of the biomass-derived blending component present in the gasoline composition will be in the range of from 0.1 to 60% vol, 0.5 to 55% vol or 1 to 50% vol.

For diesel fuel compositions according to the present invention, the amount of the biomass-derived blending component present in the diesel fuel composition will be in the range of from 0.1 to 60% vol, 0.5 to 55% vol or 1 to 50% vol.

For kerosene compositions according to the present invention, the amount of the biomass-derived blending component present in the kerosene composition will be in the range of from 0.1 to 90% vol, 0.5 to 85% vol or 1 to 80% vol, such as in the range of from 0.1 to 60% vol, 0.5 to 55% vol or 1 to 50% vol.

The liquid fuel composition of the present invention is typically selected from a gasoline, kerosene or diesel fuel composition. If the liquid fuel composition is a gasoline composition, then the gasoline composition has an initial boiling point in the range of from 15° C. to 70° C. (IP123), a final boiling point of at most 230° C. (IP123), a RON in the range of from 85 to 110 (ASTM D2699) and a MON in the range of from 75 to 100 (ASTM D2700).

If the liquid fuel composition is a kerosene composition, then the kerosene composition has an initial boiling point in the range of from 110 to 180° C., a final boiling point in the range of from 200 to 320° C. and a viscosity at −20° C. in the range of from 0.8 to 10 mm$^2$/s (ASTM D445).

If the liquid fuel composition is a diesel fuel composition, then the diesel fuel composition has an initial boiling point in the range of from 130° C. to 230° C. (IP123), a final boiling point of at most 410° C. (IP123) and a cetane number in the range of from 35 to 120 (ASTM D613).

Preferably, the liquid fuel composition of the present invention additionally comprises one or more fuel additive.

Gasoline Compositions

The gasoline composition according to the present invention typically comprises mixtures of hydrocarbons boiling in the range from 15 to 230° C., more typically in the range of from 25 to 230° C. (EN-ISO 3405). The initial boiling point of the gasoline compositions according to the present invention are in the range of from 15 to 70° C. (IP123), preferably in the range of from 20 to 60° C., more preferably in the range of from 25 to 50° C. The final boiling point of the gasoline compositions according to the present invention is at most 230° C., preferably at most 220° C., more preferably at most 210° C. The optimal ranges and distillation curves typically varying according to climate and season of the year.

In addition to the biomass-derived blending component, the hydrocarbons in the gasoline composition may be derived by any means known in the art, conveniently the hydrocarbons may be derived in any known manner from straight-run gasoline, synthetically-produced aromatic hydrocarbon mixtures, thermally or catalytically cracked hydrocarbons, hydro-cracked petroleum fractions, catalytically reformed hydrocarbons or mixtures of these.

The research octane number (RON) of the gasoline compositions according to the present invention is in the range of from 85 to 110 (ASTM D2699). Preferably, the RON of the gasoline composition will be at least 90, for instance in the range of from 90 to 110, more preferably at least 91, for instance in the range of from 91 to 105, even more preferably at least 92, for instance in the range of from 92 to 103, even more preferably at least 93, for instance in the range of from 93 to 102, and most preferably at least 94, for instance in the range of from 94 to 100.

The motor octane number (MON) of the gasoline compositions according to the present invention is in the range of from 75 to 100 (ASTM D2699). Preferably, the MON of the gasoline composition will be at least 80, for instance in the range of from 80 to 100, more preferably at least 81, for instance in the range of from 81 to 95, even more preferably at least 82, for instance in the range of from 82 to 93, even more preferably at least 83, for instance in the range of from 83 to 92, and most preferably at least 84, for instance in the range of from 84 to 90.

Typically, gasoline compositions comprise a mixture of components selected from one or more of the following groups: saturated hydrocarbons, olefinic hydrocarbons, aromatic hydrocarbons, and oxygenated hydrocarbons. Conveniently, the gasoline composition may comprise a mixture of saturated hydrocarbons, olefinic hydrocarbons, aromatic hydrocarbons, and, optionally, oxygenated hydrocarbons.

Typically, the olefinic hydrocarbon content of the gasoline composition is in the range of from 0 to 40% by volume based on the gasoline (ASTM D1319); preferably, the olefinic hydrocarbon content of the gasoline composition is in the range of from 0 to 30% by volume based on the gasoline composition, more preferably, the olefinic hydrocarbon content of the gasoline composition is in the range of from 0 to 20% by volume based on the gasoline composition.

Typically, the aromatic hydrocarbon content of the gasoline composition is in the range of from 0 to 70% by volume based on the gasoline (ASTM D1319), for instance the aromatic hydrocarbon content of the gasoline composition is in the range of from 10 to 60% by volume based on the gasoline composition; preferably, the aromatic hydrocarbon content of the gasoline composition is in the range of from 0 to 50% by volume based on the gasoline composition, for instance the aromatic hydrocarbon content of the gasoline composition is in the range of from 10 to 50% by volume based on the gasoline composition.

The benzene content of the gasoline composition is at most 10% by volume, more preferably at most 5% by volume, especially at most 1% by volume based on the gasoline composition.

The gasoline composition preferably has a low or ultra-low sulfur content, for instance at most 1000 ppmw (parts per million by weight), preferably no more than 500 ppmw, more preferably no more than 100, even more preferably no more than 50 and most preferably no more than even 10 ppmw.

The gasoline composition also preferably has a low total lead content, such as at most 0.005 g/l, most preferably being lead free-having no lead compounds added thereto (i.e. unleaded).

When the gasoline composition comprises oxygenated hydrocarbons, at least a portion of non-oxygenated hydrocarbons will be substituted for oxygenated hydrocarbons. The oxygen content of the gasoline may be up to 30% by weight (EN 1601) based on the gasoline composition. For example, the oxygen content of the gasoline may be up to 25% by weight, preferably up to 10% by weight. Conveniently, the oxygenate concentration will have a minimum concentration selected from any one of 0, 0.2, 0.4, 0.6, 0.8, 1.0, and 1.2% by weight, and a maximum concentration selected from any one of 5, 4.5, 4.0, 3.5, 3.0, and 2.7% by weight.

Examples of oxygenated hydrocarbons that may be incorporated into the gasoline, other than the oxygenated hydrocarbons that may be present in the biomass-derived blending component, include alcohols, ethers, esters, ketones, aldehydes, carboxylic acids and their derivatives, and oxygen containing heterocyclic compounds. Preferably, the oxygenated hydrocarbons incorporated are selected from alcohols (such as methanol, ethanol, propanol, iso-propanol, butanol, tert-butanol and iso-butanol), ethers (preferably ethers containing 5 or more carbon atoms per molecule, e.g., methyl tert-butyl ether) and esters (preferably esters containing 5 or more carbon atoms per molecule); a particularly preferred oxygenated hydrocarbon is ethanol derived from biomass.

When oxygenated hydrocarbons are present in the gasoline composition, the amount of oxygenated hydrocarbons in the gasoline composition may vary over a wide range. For example, gasolines comprising a major proportion of oxygenated hydrocarbons are currently commercially available in countries such as Brazil and U.S.A, e.g., E85, as well as gasoline comprising a minor proportion of oxygenated hydrocarbons, e.g., E10 and E5. Therefore, the amount of oxygenated hydrocarbons present in the gasoline composition is preferably selected from one of the following amounts: up to 85% by volume; up to 65% by volume; up to 30% by volume; up to 20% by volume; up to 15% by volume; and up to 10% by volume, depending upon the desired final formulation of the gasoline. Conveniently, the gasoline composition may contain at least 0.5, 1.0 or 2.0% by volume oxygenated hydrocarbons.

Examples of suitable gasoline compositions include gasolines having an olefinic hydrocarbon content of from 0 to 20% by volume (ASTM D1319), an oxygen content of from 0 to 5% by weight (EN 1601), an aromatic hydrocarbon content of from 0 to 50% by volume (ASTM D1319) and a benzene content of at most 1% by volume.

While not critical to the present invention, the gasoline compositions of the present invention may conveniently additionally include one or more fuel additive. The concentration and nature of the fuel additive(s) that may be included in the gasoline composition of the present invention is not critical. Non-limiting examples of suitable types of fuel additives that can be included in the gasoline composition of the present invention include anti-oxidants, corrosion inhibitors, detergents, dehazers, antiknock additives, metal deactivators, valve-seat recession protectant compounds, dyes, friction modifiers, carrier fluids, diluents and markers. Examples of suitable such additives are described generally in U.S. Pat. No. 5,855,629.

The fuel additives can also be blended with one or more diluents or carrier fluids, to form an additive concentrate, the additive concentrate can then be admixed with the gasoline composition of the present invention. The (active matter) concentration of any additives present in the gasoline composition of the present invention is preferably up to 1 percent by weight, more preferably in the range from 5 to 1000 ppmw, advantageously in the range of from 75 to 300 ppmw, such as from 95 to 150 ppmw.

Alternatively, the gasoline composition of the present invention may be an aviation gasoline. If the gasoline composition is an aviation gasoline then, depending upon the grade of the aviation gasoline, the Lean Mixture Motor Octane Number will be at least 80 (ASTM D2700) and the Rich Mixture Octane Number will be at least 87 (ASTM D 909), or the Lean Mixture Motor Octane Number will be at least 99.5 (ASTM D2700) and the Performance Number will be at least 130 (ASTM D 909). Furthermore, if the gasoline composition is an aviation gasoline then the Reid Vapour Pressure at 37.8° C. will be in the range of from 38.0 to 49.0 kPa (ASTM D323), the final boiling point will be at most 170° C. (ASTM D 86), and the tetraethyl lead content will be at most 0.85 gPb/l.

Kerosene Fuel Compositions

The kerosene fuel compositions of the present invention have use in aviation engines, such as jet engines or aero diesel engines, but also in any other suitable power or lighting source. In addition to the biomass-derived blending component, the kerosene fuel composition may comprise a mixture of two or more different fuel components, and/or be additivated as described below.

The kerosene fuel compositions will typically have boiling points within the range of 80 to 320° C., preferably in the range of 110 to 320° C., more preferably in the range of from 130 to 300° C., depending on grade and use. They will typically have a density from 775 to 845 kg/m$^3$, preferably from 780 to 830 kg/m$^3$, at 15° C. (e.g., ASTM D4502 or IP 365). They will typically have an initial boiling point in the range 80 to 150° C., preferably in the range 110 to 150° C., and a final boiling point in the range 200 to 320° C. Their kinematic viscosity at −20° C. (ASTM D445) is typically in the range of from 0.8 to 10 mm$^2$/s, preferably from 1.2 to 8.0 mm$^2$/s.

The kerosene fuel composition of the present invention preferably contains no more than 3000 ppmw sulfur, more preferably no more than 2000 ppmw, or no more than 1000 ppmw, or no more than 500 ppmw sulfur.

The kerosene fuel composition or the components thereof may be additivated (additive-containing) or unadditivated (additive-free). If additivated, e.g., at the refinery or in later stages of fuel distribution, it will contain minor amounts of one or more additives selected for example from anti-static agents (e.g., STADIS™ 450 (ex. Octel)), antioxidants (e.g., substituted tertiary butyl phenols), metal deactivator additives (e.g., N,N'-disalicylidene 1,2-propanediamine), fuel system icing inhibitor additives (e.g., diethylene glycol monomethyl ether), corrosion inhibitor/lubricity improver additives (e.g., APOLLO™ PRI 19 (ex. Apollo), DCI 4A (ex. Octel), NALCO™ 5403 (ex. Nalco)), or thermal stability improving additives (e.g., APA 101™, (ex. Shell)) that are approved in international civil and/or military jet fuel specifications.

The kerosene fuel composition of the present invention is particularly applicable where the kerosene fuel composition is used or intended to be used in a jet engine. Unless otherwise stated, the (active matter) concentration of each such additional component in the additivated kerosene fuel composition is at levels required or allowed in international jet fuel specifications. In the above, amounts (concentrations, % v, ppmw, wt %) of components are of active matter, i.e. exclusive of volatile solvents/diluent materials, unless otherwise stipulated in the relevant specification.

Diesel Fuel Compositions

The diesel fuel composition according to the present invention typically includes mixtures of hydrocarbons boiling in the range from 130 to 410° C., more typically in the range of from 150 to 400° C. The initial boiling point of the diesel fuel compositions according to the present invention are in the range of from 130 to 230° C. (IP123), preferably in the range of from 140 to 220° C., more preferably in the range of from 150 to 210° C. The final boiling point of the diesel fuel compositions according to the present invention is at most 410° C., preferably at most 405° C., more preferably at most 400° C.

In addition to the biomass-derived blending component, the diesel fuel composition may comprise a mixture of two or more different diesel fuel components, and/or be additivated as described below.

Such diesel fuel compositions will contain one or more base fuels which may typically comprise liquid hydrocarbon middle distillate gas oil(s), for instance petroleum derived gas oils. Such fuels will typically have boiling points within the range described above, depending on grade and use. They will typically have a density from 750 to 1000 kg/m$^3$, preferably from 780 to 860 kg/m$^3$, at 15° C. (e.g., ASTM D4502 or IP 365) and a cetane number (ASTM D613) of from 35 to 120, more preferably from 40 to 85. They will typically have an initial boiling point in the range described above and a final boiling point of at most 410° C., preferably at most 405° C., more preferably at most 400° C., most preferably in the range 290 to 400° C. Their kinematic viscosity at 40° C. (ASTM D445) might suitably be from 1.2 to 4.5 mm$^2$/s.

An example of a petroleum derived gas oil is a Swedish Class 1 base fuel, which will have a density from 800 to 820 kg/m$^3$ at 15° C. (SS-EN ISO 3675, SS-EN ISO 12185), a T95 of 320° C. or less (SS-EN ISO 3405) and a kinematic viscosity at 40° C. (SS-EN ISO 3104) from 1.4 to 4.0 mm$^2$/s, as defined by the Swedish national specification EC1.

Optionally, non-mineral oil based fuels, such as biofuels (other than the component having at least one $C_{4+}$ compound derivable from a water-soluble oxygenated hydrocarbon) or Fischer-Tropsch derived fuels, may also form or be present in the diesel fuel. Such Fischer-Tropsch fuels may for example be derived from natural gas, natural gas liquids, petroleum or shale oil, petroleum or shale oil processing residues, coal or biomass.

The diesel fuel composition preferably contains no more than 5000 ppmw sulfur, more preferably no more than 500 ppmw, or no more than 350 ppmw, or no more than 150 ppmw, or no more than 100 ppmw, or no more than 70 ppmw, or no more than 50 ppmw, or no more than 30 ppmw, or no more than 20 ppmw, or most preferably no more than 15 ppmw sulfur.

The diesel base fuel may itself be additivated (additive-containing) or unadditivated (additive-free). If additivated, e.g., at the refinery, it will contain minor amounts of one or more additives selected for example from anti-static agents, pipeline drag reducers, flow improvers (e.g., ethylene/vinyl acetate copolymers or acrylate/maleic anhydride copolymers), lubricity additives, antioxidants and wax anti-settling agents.

The diesel fuel typically also includes one or more fuel additive. Detergent-containing diesel fuel additives are known and commercially available. Such additives may be added to diesel fuels at levels intended to reduce, remove, or slow the build-up of engine deposits. Examples of detergents suitable for use in diesel fuel additives for the present purpose include polyolefin substituted succinimides or succinamides of polyamines, for instance polyisobutylene succinimides or polyisobutylene amine succinamides, aliphatic amines, Mannich bases or amines and polyolefin (e.g., polyisobutylene) maleic anhydrides. Succinimide dispersant additives are described for example in GB-A-960493, EP-A-0147240, EP-A-0482253, EP-A-0613938, EP-A-0557516 and WO-A-98/42808. Particularly preferred are polyolefin substituted succinimides such as polyisobutylene succinimides.

The diesel fuel additive mixture may contain other components in addition to the detergent. Examples are lubricity enhancers; dehazers (e.g., alkoxylated phenol formaldehyde polymers); anti-foaming agents (e.g., polyether-modified polysiloxanes); ignition improvers (cetane improvers) (e.g., 2-ethylhexyl nitrate (EHN), cyclohexyl nitrate, di-tert-butyl peroxide and those disclosed in U.S. Pat. No. 4,208,190 at column 2, line 27 to column 3, line 21); anti-rust agents (e.g., a propane-1,2-diol semi-ester of tetrapropenyl succinic acid, or polyhydric alcohol esters of a succinic acid derivative, the succinic acid derivative having on at least one of its alpha-carbon atoms an unsubstituted or substituted aliphatic hydrocarbon group containing from 20 to 500 carbon atoms (e.g., the pentaerythritol diester of polyisobutylene-substituted succinic acid)); corrosion inhibitors; reodorants; anti-wear additives; anti-oxidants (e.g., phenolics such as 2,6-di-tert-butylphenol, or phenylenediamines such as N,N'-di-sec-butyl-p-phenylenediamine); metal deactivators; combustion improvers; static dissipator additives; cold flow improvers; and wax anti-settling agents.

The diesel fuel additive mixture may contain a lubricity enhancer, especially when the diesel fuel composition has a low sulfur content (e.g., 500 ppmw or less). In the additivated diesel fuel composition, the lubricity enhancer is conveniently present at a concentration of less than 1000 ppmw, preferably between 50 and 1000 ppmw, more preferably between 70 and 1000 ppmw. Suitable commercially available lubricity enhancers include ester- and acid-based additives. Other lubricity enhancers are described in the patent literature, in particular in connection with their use in low sulfur content diesel fuels, for example in: The paper by Danping Wei and H. A. Spikes, "The Lubricity of Diesel Fuels", Wear, III (1986) 217-235; WO-A-95/33805 (describing cold flow improvers to enhance lubricity of low sulfur fuels); WO-A-94/17160 (describing certain esters of a carboxylic acid and an alcohol wherein the acid has from 2 to 50 carbon atoms and the alcohol has 1 or more carbon atoms, particularly glycerol monooleate and di-isodecyl adipate, as fuel additives for wear reduction in a diesel engine injection system); U.S. Pat. No. 5,490,864 (describing certain dithiophosphoric diester-dialcohols as anti-wear lubricity additives for low sulfur diesel fuels); and WO-A-98/01516 (describing certain alkyl aromatic compounds having at least one carboxyl group attached to their aromatic nuclei, to confer anti-wear lubricity effects particularly in low sulfur diesel fuels).

It may also be preferred for the diesel fuel composition to contain an anti-foaming agent, more preferably in combination with an anti-rust agent and/or a corrosion inhibitor and/or a lubricity enhancing additive.

Unless otherwise stated, the (active matter) concentration of each such additive component in the additivated diesel fuel composition is preferably up to 10000 ppmw, more preferably in the range from 0.1 to 1000 ppmw, advantageously from 0.1 to 300 ppmw, such as from 0.1 to 150 ppmw.

The (active matter) concentration of any dehazer in the diesel fuel composition will preferably be in the range from 0.1 to 20 ppmw, more preferably from 1 to 15 ppmw, still more preferably from 1 to 10 ppmw, advantageously from 1 to 5 ppmw. The (active matter) concentration of any ignition improver present will preferably be 2600 ppmw or less, more preferably 2000 ppmw or less, conveniently from 300 to 1500 ppmw. The (active matter) concentration of any detergent in the diesel fuel composition will preferably be in the range from 5 to 1500 ppmw, more preferably from 10 to 750 ppmw, most preferably from 20 to 500 ppmw.

In the case of a diesel fuel composition, for example, the fuel additive mixture will typically contain a detergent, optionally together with other components as described above, and a diesel fuel-compatible diluent, which may be a mineral oil, a solvent such as those sold by Shell companies under the trade mark "SHELLSOL", a polar solvent such as an ester and, in particular, an alcohol, e.g., hexanol, 2-ethylhexanol, decanol, isotridecanol and alcohol mixtures such as those sold by Shell companies under the trade mark "LINEVOL", especially LINEVOL 79 alcohol which is a mixture of $C_{7-9}$ primary alcohols, or a $C_{12-14}$ alcohol mixture which is commercially available.

The total content of the additives in the diesel fuel composition may be suitably between 0 and 10000 ppmw and preferably below 5000 ppmw. In the above, amounts (concentrations, % vol, ppmw, % wt) of components are of active matter, i.e. exclusive of volatile solvents/diluent materials.

The following examples are to be considered illustrative of various aspects of the invention and should not be construed to limit the scope of the invention, which are defined by the appended claims.

EXAMPLES

Example 1

Product streams from the examples described below were analyzed as follows. The organic liquid phase was collected and analyzed using either gas chromatograph with mass spectrometry detection or flame ionization detection. Component separation was achieved using a column with a bonded 100% dimethyl polysiloxane stationary phase. Relative concentrations of individual components were estimated via peak integration and dividing by the sum of the peak areas for an entire chromatogram. Compounds were identified by comparison to standard retention times and/or comparison of mass spectra to a compiled mass spectral database. Vapor phase compositions, for the non-condensable species, were determined by gas chromatography with a thermal conductivity detector and flame ionization or gas chromatography with a flame ionization detector or mass spectrometry detectors for other vapor phase components (e.g., aqueous or organic phase condensable species). The liquid phase fraction was analyzed by gas chromatography with and without a derivatization of the organic components of the fraction using a flame ionization detector. Product yields are represented by the feed carbon present in each product fraction. The weight hourly space velocity (WHSV) was defined as the weight of feed introduced into the system per weight of catalyst per hour, and based on the weight of the oxygenated hydrocarbon feed only, excluding water present in the feed.

Example 2

A biomass feed stream containing 10% (w/v) microcrystalline cellulose (MCC) in water was converted to a gas phase containing volatile $C_{2+}O_{1-2}$ oxygenates and a liquid phase using modified palladium on tungstated-zirconia oxide support. The conversion was carried out in a 300 ml Parr reactor at 260° C. and 1000 psi $H_2$, with a 15 minute reaction time. The reaction included a catalyst:biomass ratio of 1:3.

Figure 3:
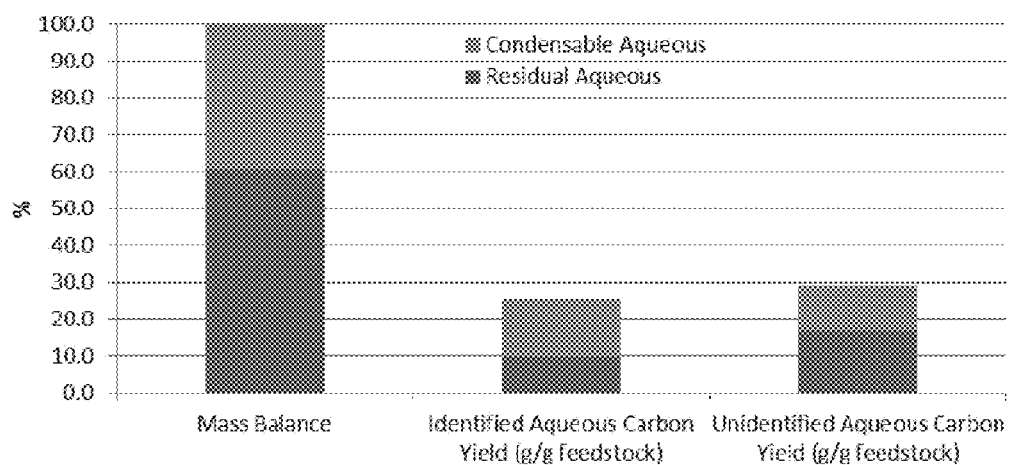
FIG. 3 is a graph providing data for the conversion of a biomass feed stream containing microcrystalline cellulose (MCC) according to the present invention.
Figure 4B:
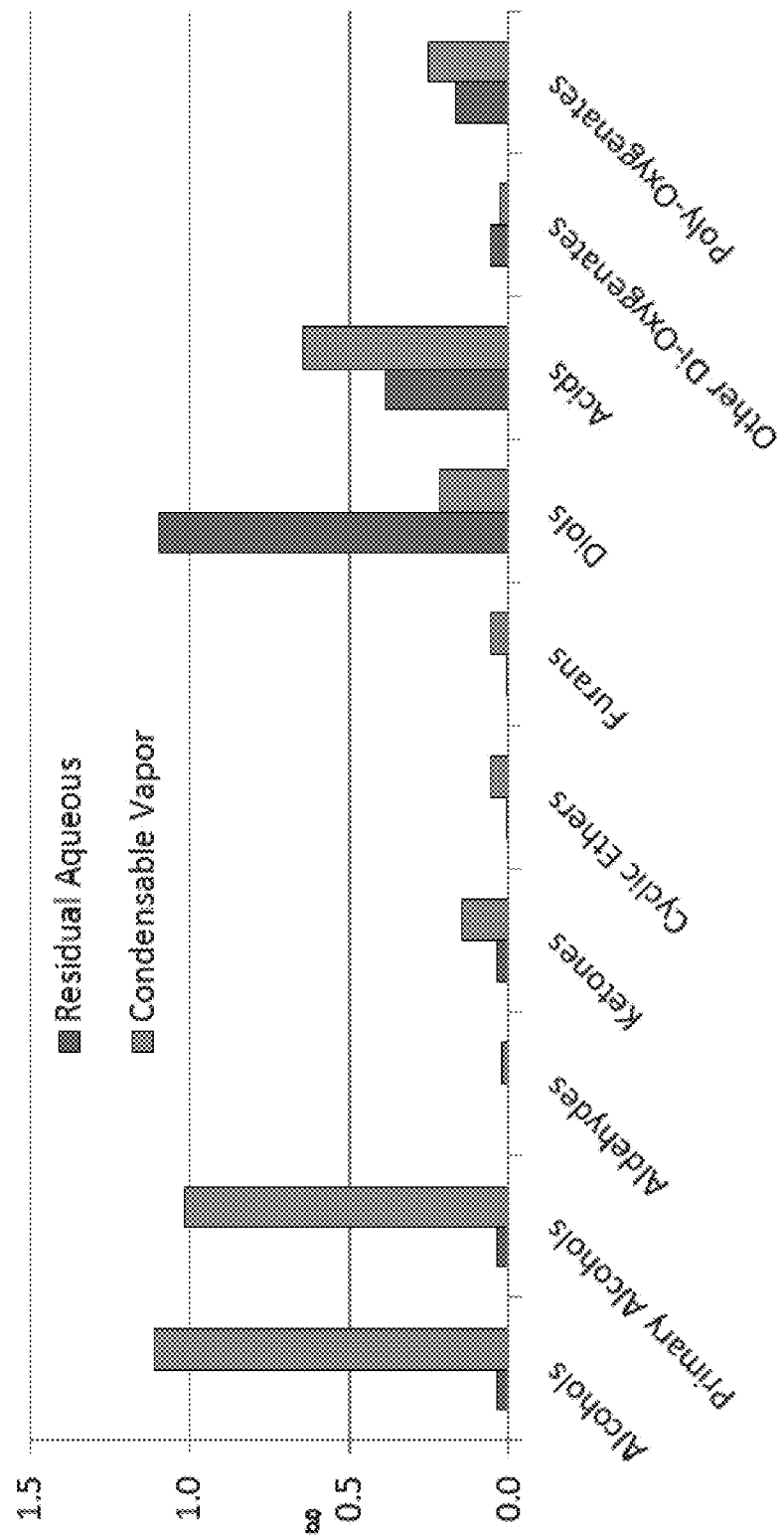
Figure 5:
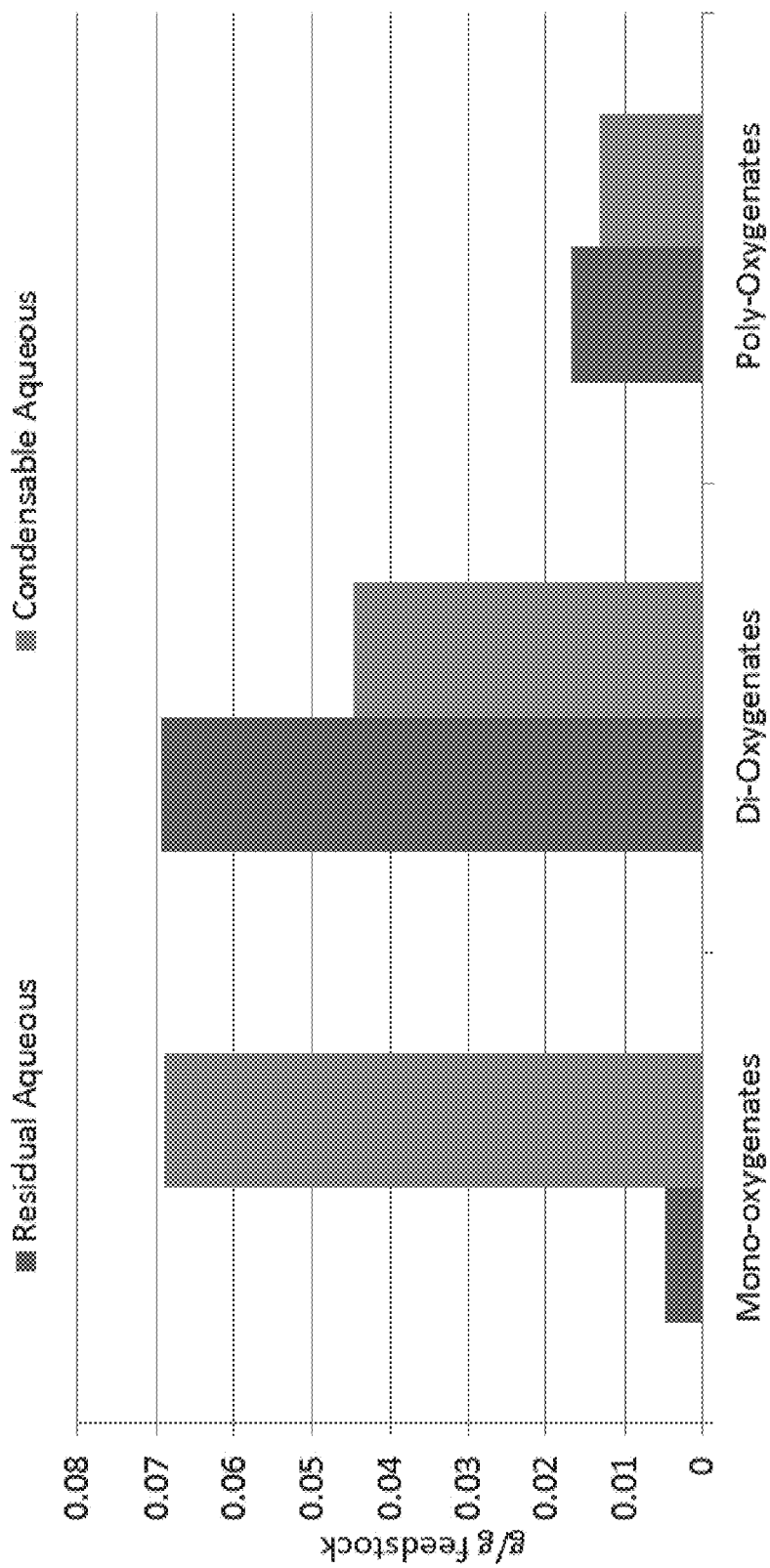
FIG. 5 is a graph providing the identified aqueous oxygenate distribution from the conversion of a biomass feed stream containing MCC according to the present invention.
Figure 6:
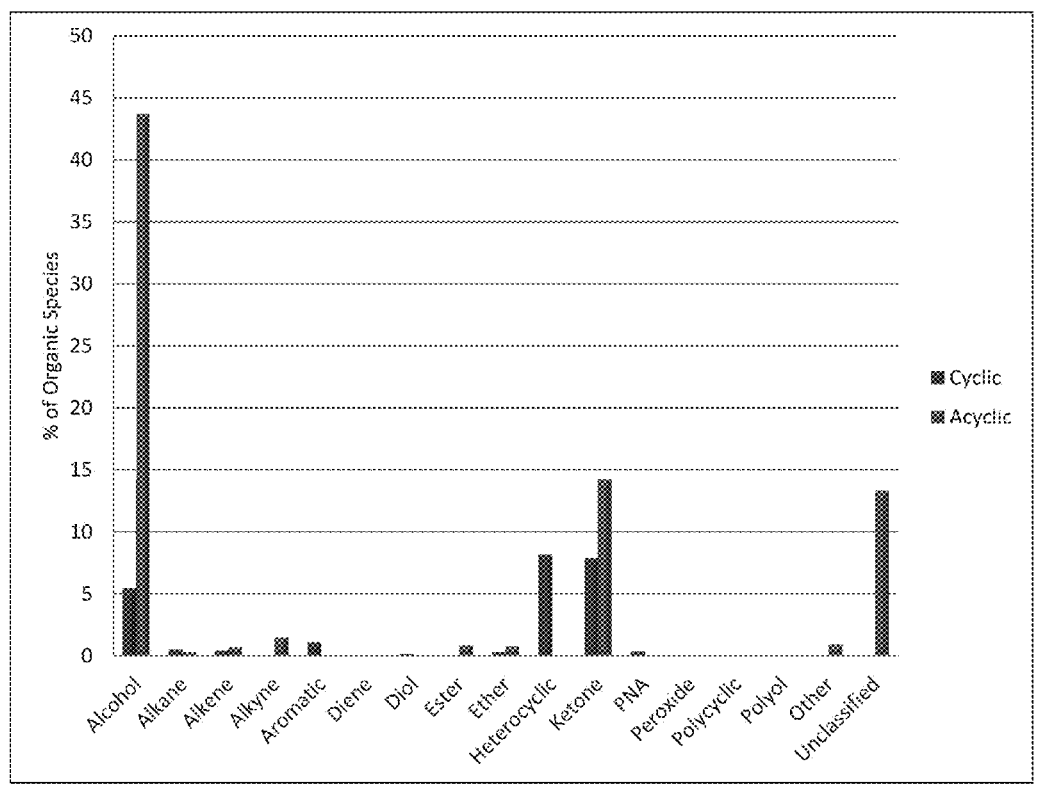
FIG. 6 is a graph providing the distribution of the condensable organic vapor phase derived from the conversion of a biomass feed stream containing MCC according to the present invention.
Figure 7:
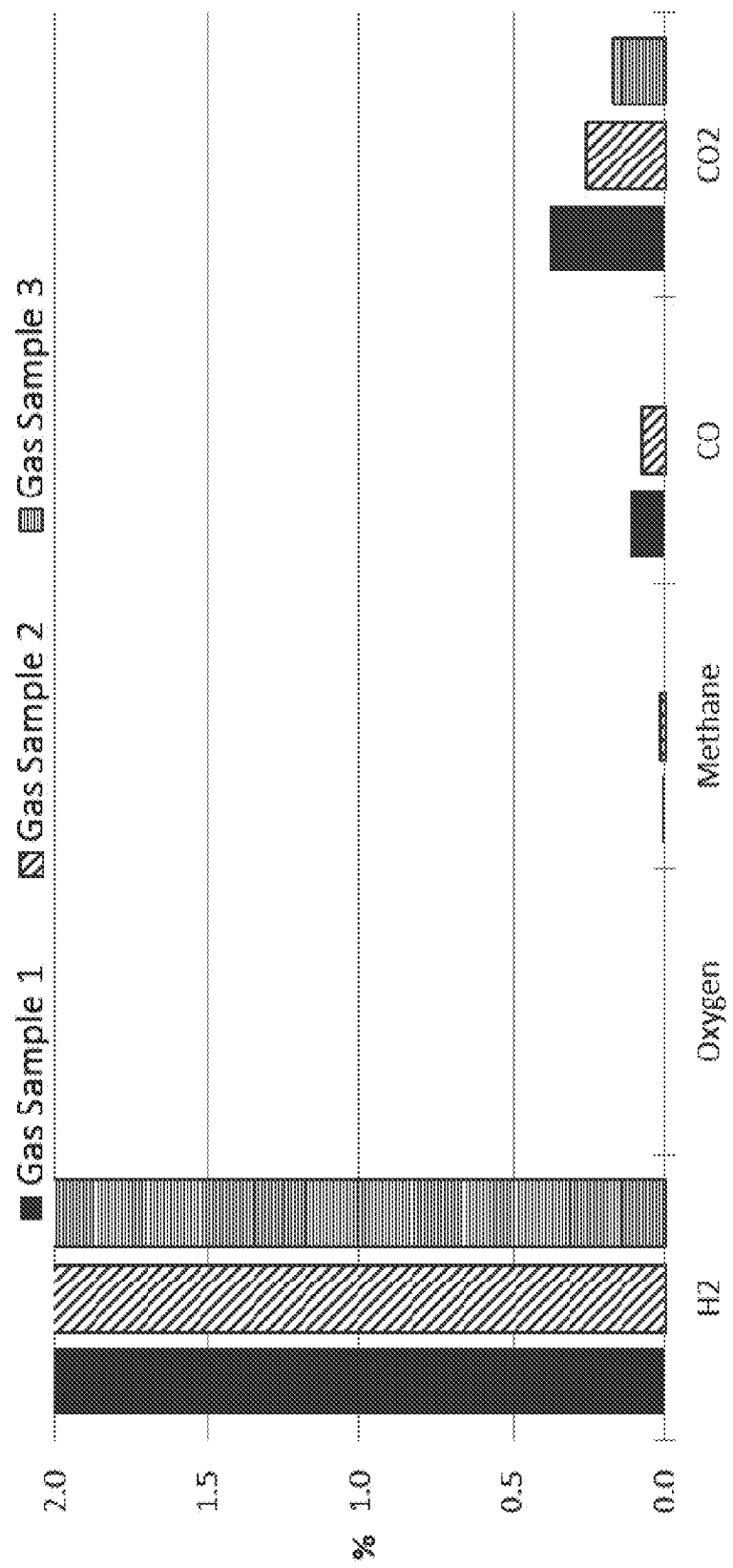
FIG. 7 is a graph illustrating the analysis of non-condensable gaseous products from the conversion of a biomass feed stream containing MCC according to the present invention.
Figure 8:
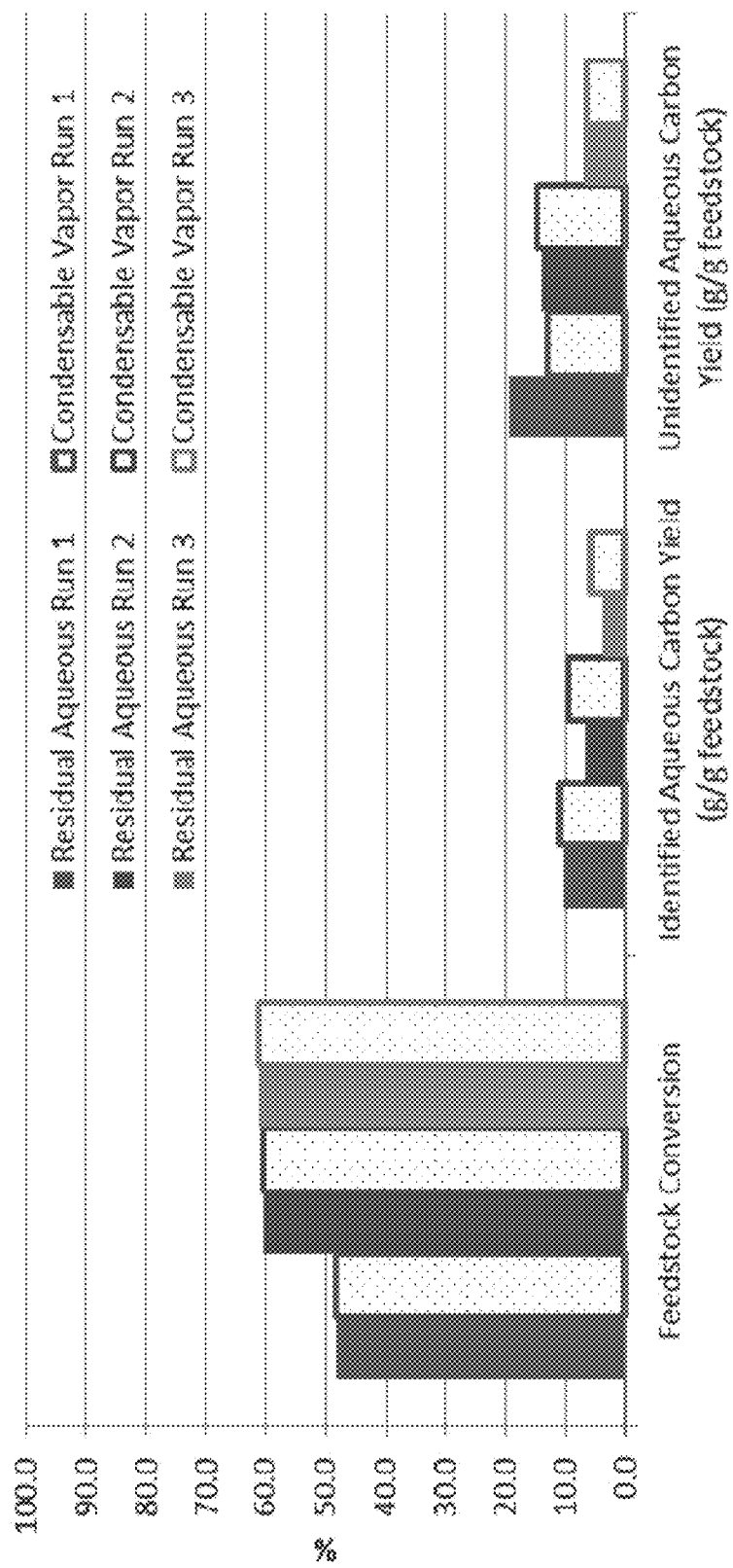
FIG. 8 is a graph providing data for the conversion of a biomass feed stream containing loblolly pine according to the present invention.
Figure 9:
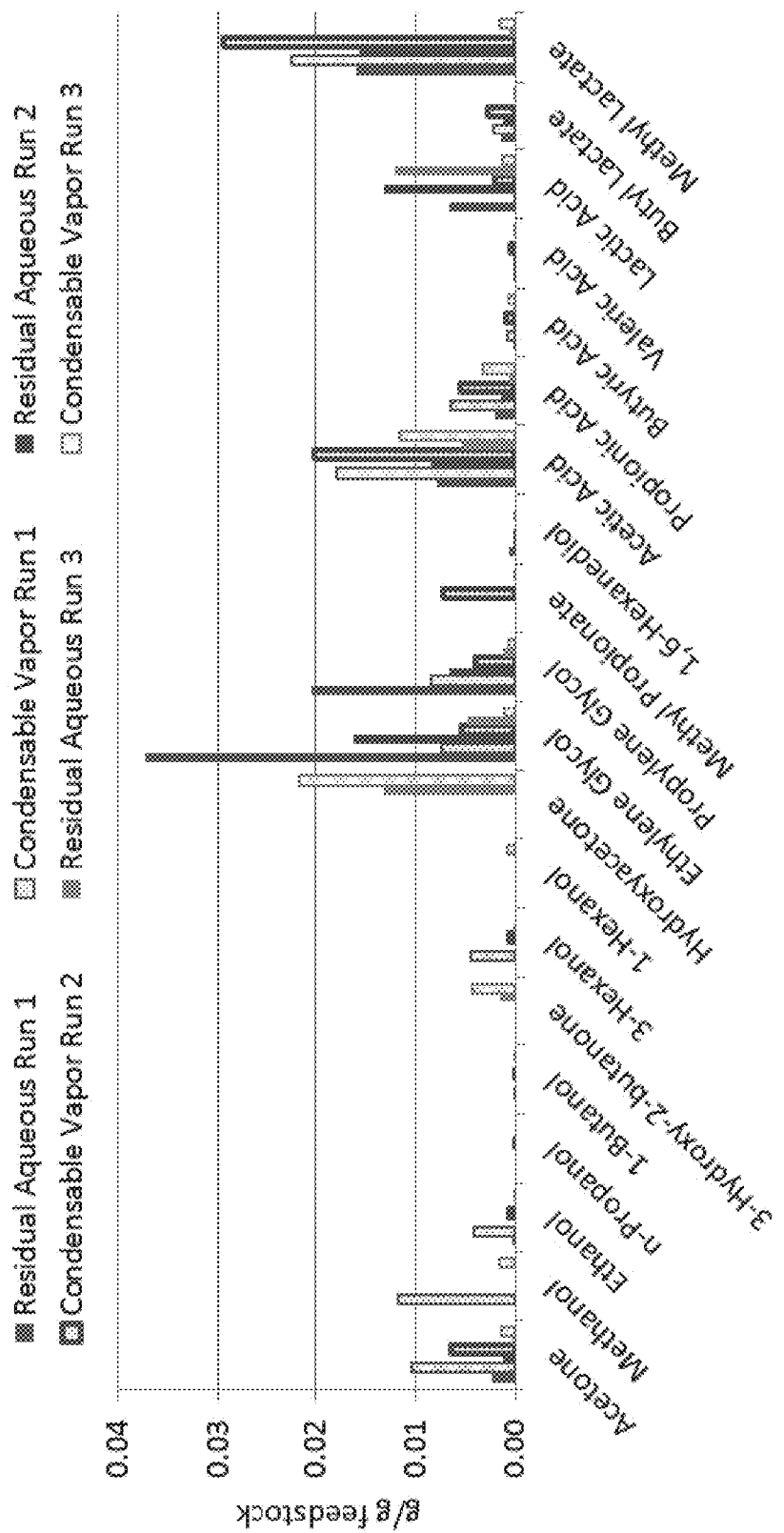
FIGS. 9a and 9b are graphs providing the most abundant aqueous product speciation and the identified aqueous product distribution, respectively, from the conversion of a biomass feed stream containing loblolly pine according to the present invention.
Figure 9:
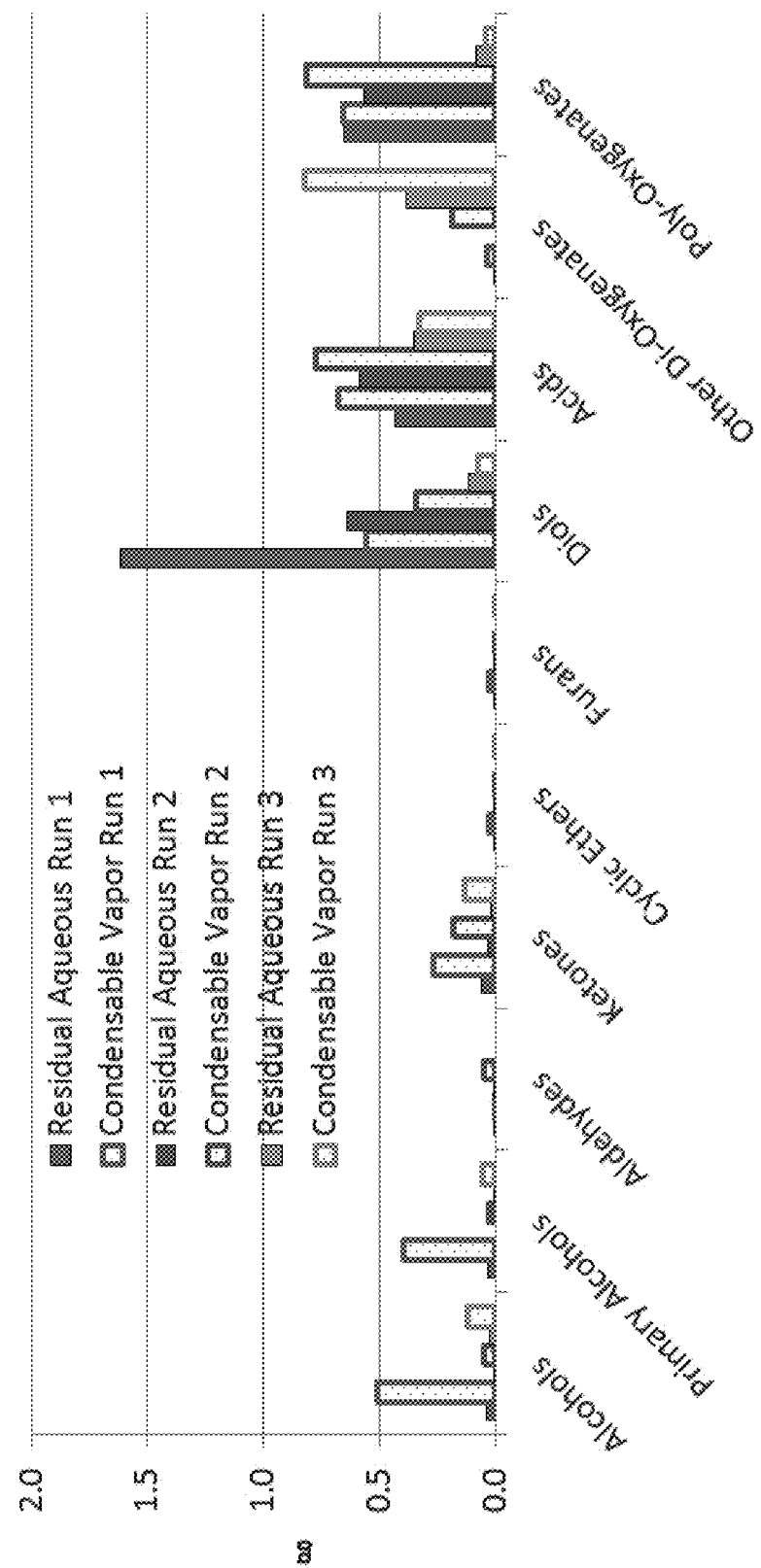
Figure 10:
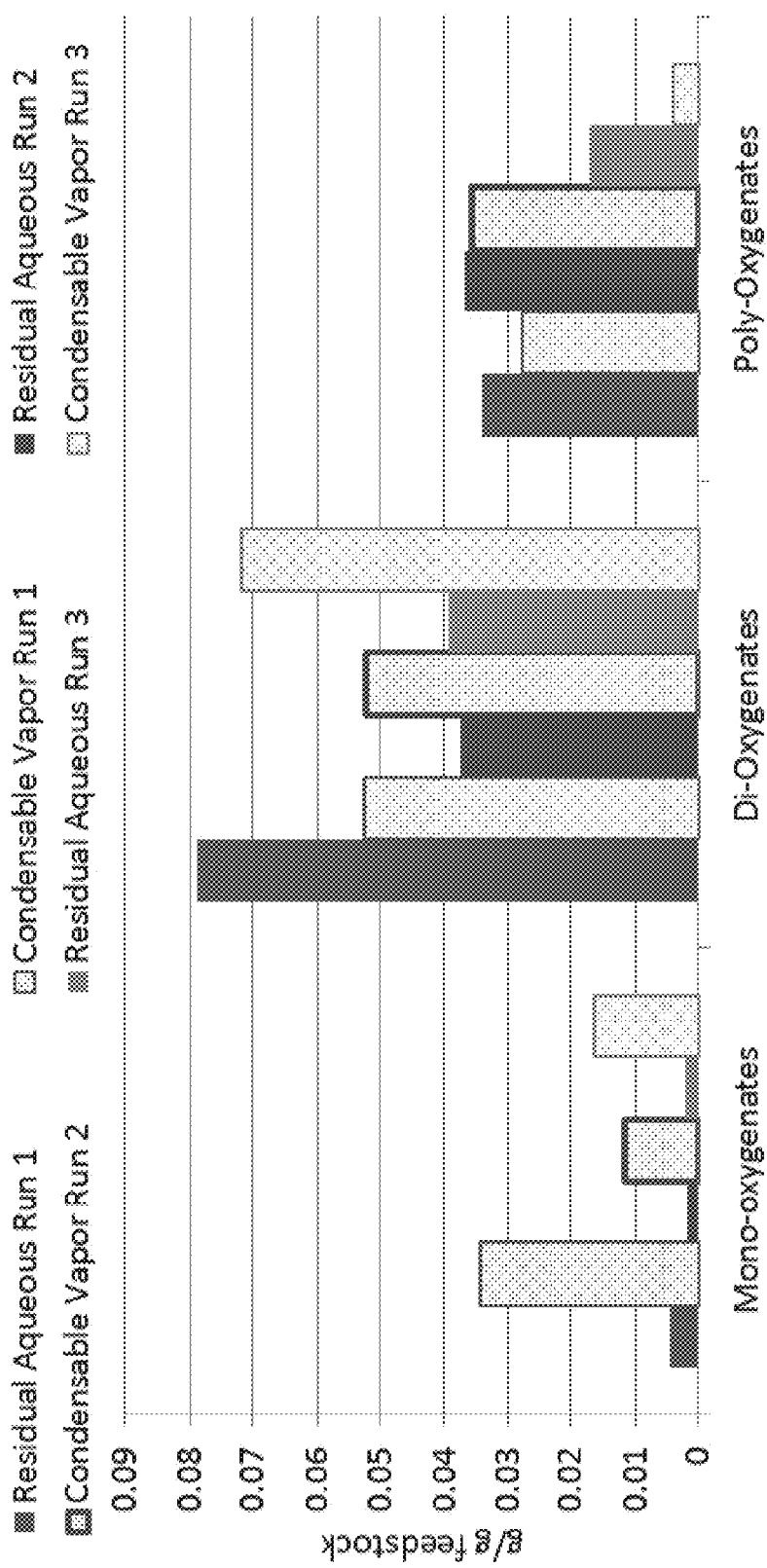
FIG. 10 is a graph providing the identified aqueous oxygenate distribution from the conversion of a biomass feed stream containing loblolly pine according to the present invention.

Hydrogen sparging and constant mixing at 800 rpm was used to increase mixing and catalyst contact. Mixing occurred from the start of heating to the end of cooling. The constant sparging allowed volatile $C_{2+}O_{1-2}$ oxygenates to be collected overhead and separated from the residual aqueous products left in the reactor. Both liquid phase and vapor phase products can be seen in FIGS. 3, 4a, 4b, and 5. FIG. 3, in particular, provides the overall conversion and selectivity. The condensed vapor stream contained $C_{2+}O_{1-2}$ oxygenates as shown in FIG. 6 and in Table 1 below. Non-condensable gas products from the vapor stream were analyzed and can be seen in FIG. 7.

TABLE 1

Organic Product Distribution of MCC

| Species | % |
| --- | --- |
| 1-HEXANOL | 10.6 |
| 1-Octanol | 2.6 |
| CYCLOPENTANONE, 2-METHYL- | 2.4 |
| 1-NONANOL | 2.3 |
| 1-DECANOL | 2.0 |
| 1-Pentanol | 1.6 |
| 2-Nonanone | 1.5 |
| (6Z)-Nonen-1-ol | 1.5 |
| 1-HEPTANOL | 1.4 |
| Cyclopentanemethanol | 1.2 |
| 3-Cyclopentyl-1-propanol | 1.2 |
| 1-Dodecanol | 1.2 |
| Phenol, 2,3-dimethyl- | 1.0 |
| 2-Hexanone | 1.0 |

Through the use of sparging and vapor phase sampling the condensed volatile oxygenates consisted primarily of alcohols and other mono-oxygenates, leaving sugars and polyols in the liquid phase. As seen by the organic product breakdown in Table 1 and FIG. 6, the organic stream collected with the vapor phase is primarily alcohols and ketones with some unidentified compounds. Carbon losses through the non-condensable gas stream are minimal as noted by the gas product analysis (FIG. 7) showing almost no carbon dioxide or monoxide.

Example 3

A biomass feed stream containing 12-17% (w/v) loblolly pine in water was converted to a gas phase containing volatile $C_{2+}O_{1-2}$ oxygenates and a liquid phase using modified palladium on a tungstated-zirconia oxide support. The conversion was carried out in a 300 ml Parr reactor at 280° C. and 1000 psi $H_2$, with a 15 minute reaction time. The reaction included a catalyst:biomass ratio of 1:3.

Hydrogen sparging and constant mixing at 800 rpm was used to increase mixing and catalyst contact. Mixing occurred from the start of heating to the end of cooling. The constant sparging allowed volatile $C_{2+}O_{1-2}$ oxygenates to be collected overhead and separated from the residual liquid phase products left in the reactor. The volatile oxygenates collected were then condensed and analyzed. Less volatile residual liquid phase products were collected after the reactor was cooled and similarly analyzed.

Figure 11:
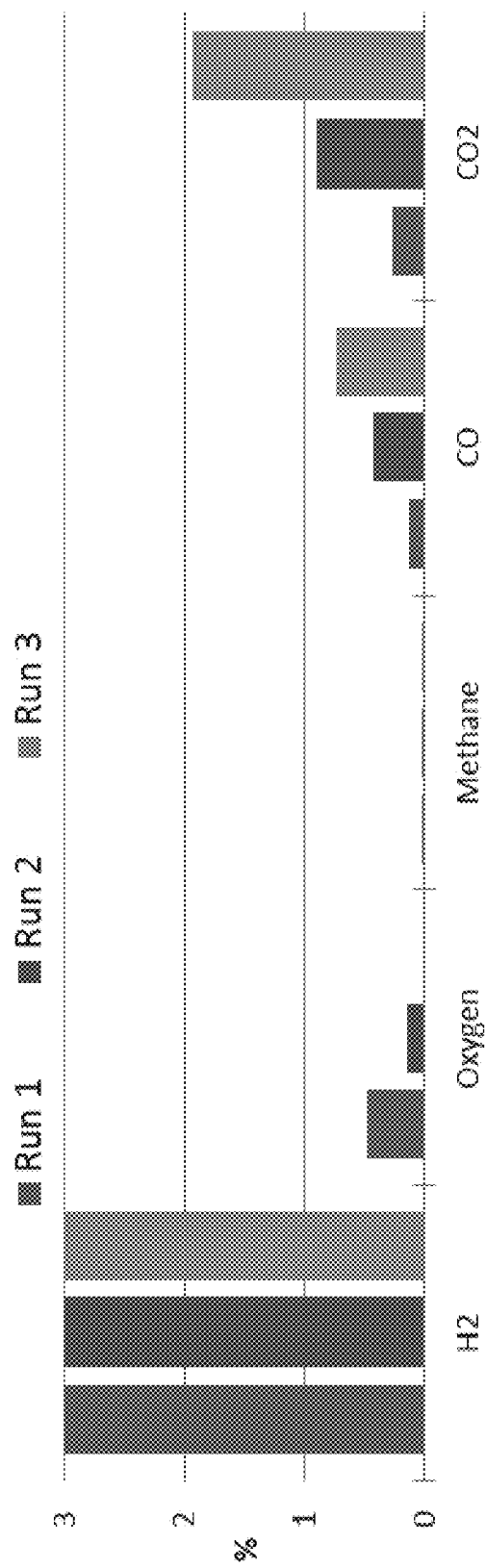
FIG. 11 is a graph illustrating the analysis of non-condensable gaseous products from the conversion of a biomass feed stream containing loblolly pine according to the present invention.

The results of the analysis of both the vapor phase and liquid phase products are provided in FIGS. 8, 9a, 9b, and 10. FIG. 11 is an analysis of the non-condesnable vapor phase products. The vapor phase contained volatile $C_{2+}O_{1-2}$ oxygenates (both mono- and di-oxygenated hydrocarbons), while the liquid phase portion consisted primarily of sugars. Minimal carbon losses through the non-condensable gas product were observed with minor carbon monoxide and carbon dioxide levels in the analysis.

Example 4

Figure 12:
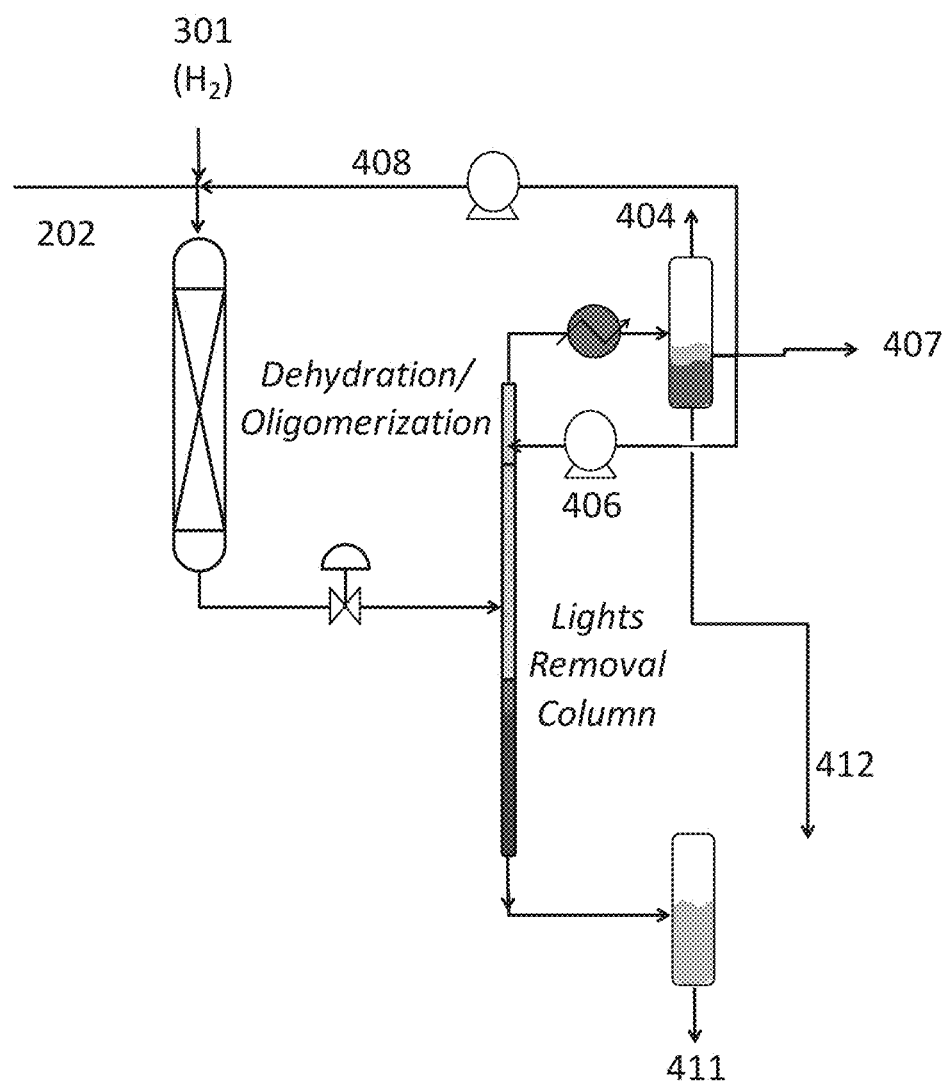
FIG. 12 is a process flow diagram illustrating one of several process configurations for conducting the condensation reactions according to the present invention.

FIG. 12 shows a process diagram illustrating an exemplary reactor system that is useful in practicing the condensation reaction of the present invention. Volatile oxygenates, such as $C_{2+}O_{1-2}$ alcohols, ketones, cyclic ethers, organic acids, or other poly-oxygenated compounds, enter the system in stream 202 and are directed through the condensation reactor (in this case a dehydration/oligomerization reactor). Hydrogen (whether external, recycled, in situ $H_2$, or a combination thereof) is co-fed to the reactor in stream 301.

The product stream from the condensation reactor is sent to the lights removal column, where moderate and heavy hydrocarbons (e.g, kerosene, diesel fuel, and lubricants) are separated in the bottoms to provide stream 411. The lighter components in the overhead are sent to a three phase separator. A gas phase stream of predominantly hydrogen and carbon dioxide, with lower amounts of light hydrocarbons, is removed in stream 404. The liquid phase, composed of water and low levels of organic compounds, is removed in stream 412. A three phase separator could also be used to remove the liquid phase upstream of the column. The overhead organic phase is split into three streams; (1) reflux back into the column, stream 406, (2) net product, stream 407, (3) recycle back to the reactor system, stream 408. In certain embodiments, the recycle stream can be sent back to the condensation reactor. Alkenes and residual oxygenates can be further oligomerized to $C_3$-$C_{30}$ hydrocarbons (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, and $C_{30}$.

Example 5

A condensation catalyst was prepared by dissolving nickel nitrate in water and then adding the mixture to an alumina bound ZSM-5 zeolite preparation ($SiO_2$:$Al_2O_3$ 30:1, ⅛ " extrudates) using an incipient wetness technique to target a nickel loading of 1.0 weight %. The preparation was dried overnight (e.g., more than 4 hours, or 5 hours, or 6 hours, or 7 hours, or 8 hours, and less than 16 hours, or 15 hours, or 14 hours, or 13 hours, or 12 hours, or 11 hours, or 10 hours) in a vacuum oven and subsequently calcined in a stream of flowing air at 400° C.

Example 6

A condensation catalyst was prepared by dissolving copper nitrate in water and then adding the mixture to a tungstated zirconia catalyst support (NorPro Saint-Gobain, Product code SZ31164, with particle sizes restricted to those that were maintained on a 60 mesh screen after passing through an 18 mesh screen) using an incipient wetness technique to target a copper loading of 10% on the catalyst after subsequent decomposition of the metal precursors. The preparation was dried overnight (e.g., more than 4 hours, or 5 hours, or 6 hours, or 7 hours, or 8 hours, and less than 16 hours, or 15 hours, or 14 hours, or 13 hours, or 12 hours, or 11 hours, or 10 hours) in a vacuum oven at 100° C. and subsequently calcined in a stream of flowing air at 400° C.

Example 7

A condensation catalyst was prepared by dissolving palladium nitrate and silver nitrate in water and then adding the mixture to a tungstated zirconia catalyst support (NorPro Saint-Gobain, Product code SZ31164, with particle sizes restricted to those that were maintained on a 60 mesh screen after passing through an 18 mesh screen) using an incipient wetness technique to target a palladium loading of 0.5% and a silver loading of 0.5% on the catalyst after subsequent decomposition of the metal precursors. The preparation was dried overnight (e.g., more than 4 hours, or 5 hours, or 6 hours, or 7 hours, or 8 hours, and less than 16 hours, or 15 hours, or 14 hours, or 13 hours, or 12 hours, or 11 hours, or 10 hours) in a vacuum oven at 100° C. and subsequently calcined in a stream of flowing air at 400° C.

Example 8

A stream of volatile $C_{2+}O_{1-2}$ oxygenates similar in composition to that produced in Example 2 and illustrated by FIG. 6 was converted to a product stream of $C_{4+}$ hydrocarbons using the condensation catalysts described in Examples 5 and 6. The composition of the intermediate stream being fed into the condensation reactor is described in Table 2, with 99% of all components having carbon chain lengths of six or less.

TABLE 2

Composition of Organic Phase Intermediate Stream
Breakdown of Organic Phase Composition

| | | |
|---|---|---|
| Alkanes | % of carbon in organic phase | 15.0 |
| Total Mono-oxygenates | % of carbon in organic phase | 75.7 |
| Alcohols | % of carbon in organic phase | 40.1 |
| Ketones | % of carbon in organic phase | 11.4 |
| Cyclic Ethers | % of carbon in organic phase | 19.3 |
| Cyclic Mono-oxygenates | % of carbon in organic phase | 5.0 |
| Organic Acids | % of carbon in organic phase | 6.9 |
| C6– Components | % of carbon in organic phase | 99.0 |

The stream of volatile oxygenates was fed over the condensation catalyst using the process configuration described in Example 4. The catalyst was loaded as a packed bed with 12" height in a 1" diameter shell and tube reactor. Reaction conditions are described in Table 3.

The heavy liquid stream (411 in FIG. 12) was collected and analyzed using the techniques listed in Example 1. Table 3 shows the organic product yields and composition as a function of catalyst formulation. Non-condensed components are those components that do not require the formation of new carbon-carbon bonds to be produced from the given feed. For simplicity, all compounds containing six or fewer carbon atoms are considered to be non-condensed components (e.g., $C_1$, $C_2$, $C_3$, $C_4$, $C_5$, $C_6$). Total condensation products are those compounds containing seven or more carbon atoms (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, and $C_{30}$), which require the formation of new carbon-carbon bonds to be formed from the given feedstock.

The exception to this is the "di-oxygenate" category, which are esters that lack a continuous carbon backbone. These compounds would not retain their chain lengths if hydrogenated to a finished liquid fuel.

The "Unclassified" category contains compounds that are too heavy for an accurate identification from the analysis technique. An estimation of carbon number is made based on boiling point, and in general these compounds have continuous carbon chains.

Both catalysts show significant condensation taking place. The stream of volatile oxygenates contained 99% non-condensed components, while the heavy liquid stream 411 product contains less than 4% in both cases. The resulting products can be hydrogenated using a hydrotreating catalyst to produce gasoline, kerosene, and diesel fuels.

TABLE 3

Conversion of Volatile Oxygenates to C7+ Carbon Chains

| Catalyst | | 1% Ni/ ZSM-5 | 10% Cu/ W—ZrO2 |
|---|---|---|---|
| WHSV | $wt_{feed}/(wt_{catalyst}\,hr)$ | 0.7 | 0.4 |
| Added Hydrogen | $mol_{H2}/mol_{feed}$ | 0.2 | 0.2 |
| Temperature | ° C. | 300 | 300 |
| Pressure | Psig | 800 | 600 |
| Heavy Organic Phase Yield (stream 411) | % of feed carbon | 69 | 42 |
| Breakdown of Heavy Organic Phase Composition | | | |
| C6– Hydrocarbons | % of carbon in organic phase | 0.1 | 2.1 |
| C6– Oxygenates | % of carbon in organic phase | 1.0 | 1.8 |
| Total Non-Condensed Components | % of carbon in organic phase | 1.1 | 3.9 |
| C7+ Hydrocarbons | % of carbon in organic phase | 30.3 | 3.7 |
| C7+ Mono-oxygenates | % of carbon in organic phase | 9.1 | 24.9 |
| C7+ Di-oxygenates | % of carbon in organic phase | 4.2 | 1.1 |
| C7+ Unclassified | % of carbon in organic phase | 55.3 | 66.3 |
| Total Condensation Products | % of carbon in organic phase | 98.9 | 96.1 |

Example 9

A stream of volatile $C_{2+}O_{1-2}$ oxygenates similar in composition to that produced in Examples 2 and 3 were converted to a product stream of $C_{4+}$ hydrocarbons using the condensation catalyst described in Example 7. Table 4 shows the composition of the intermediate stream being fed into the condensation reactor. All values are reported as weight percent.

TABLE 4

Composition of Oxygenated Intermediate Stream

| Carbon Number | Water | Alkanes | Ketones | Alcohols | Other Mono-Oxygenates | Furans | Di-oxygenates | Diols | Acids |
|---|---|---|---|---|---|---|---|---|---|
| 0 | 60.9 | | | | | | | | |
| 1 | | | | 0.1 | | | | | |
| 2 | | | | 0.1 | | | | 0.4 | 0.4 |
| 3 | | | 0.6 | 0.3 | | | 0.7 | 0.3 | 0.4 |
| 4 | | | 0.3 | 0.2 | | 0.1 | 0.7 | 0.3 | 0.4 |
| 5 | | | 0.8 | 0.5 | 0.1 | 1.3 | 0.4 | | 0.1 |
| 6 | | 0.1 | 0.8 | 1.2 | 4.7 | 5.7 | 4.3 | 0.2 | 0.2 |
| ≥7 | 0.1 | 1.4 | 2.0 | 1.3 | 0.2 | 1.8 | | | |

The stream of volatile $C_{2+}O_{1-2}$ oxygenates was fed over the condensation catalyst using the process configuration described in Example 4. The catalyst was loaded as a packed bed with 12" height in a 1" diameter shell and tube reactor.

The reaction was performed at 300° C. and 900 psig at a weight hour space velocity of 0.4 hr$^{-1}$. A hydrogen co-feed of 2.4 mol H$_2$/mol feed was used with a recycle:feed ratio of 1.7.

Figure 13:
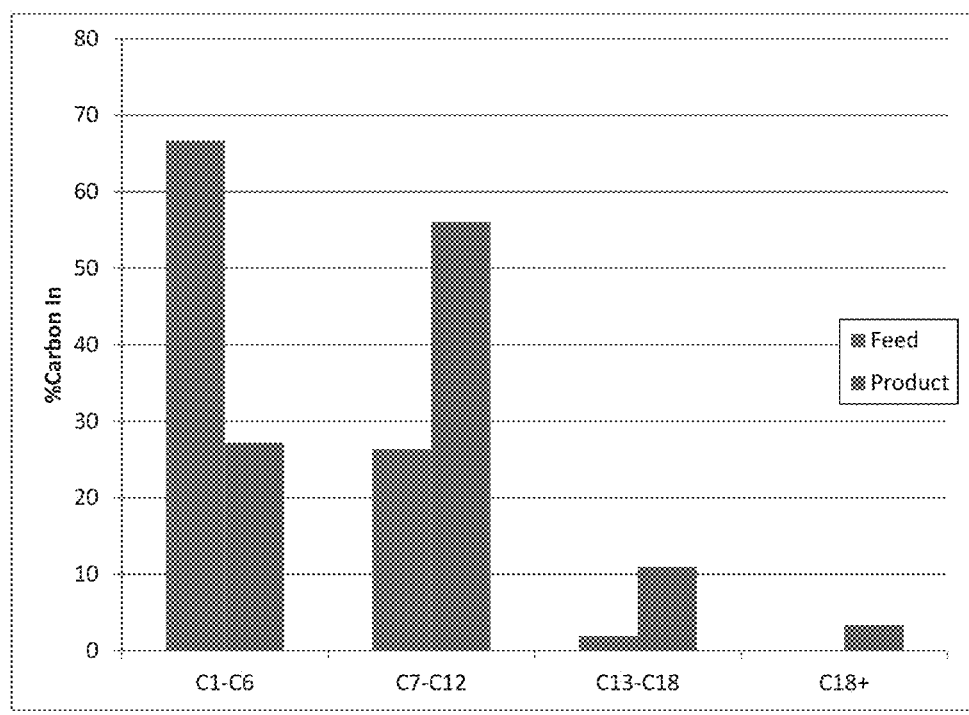
FIG. 13 is a graph providing the product yields from the conversion of volatile $C_{2+}O_{1-2}$ oxygenates over a Pd:Ag condensation catalyst.

Approximately 90% of the carbon that went into the process (e.g., deconstruction and condensation) was converted into the organic phase. Approximately 75% was contained in the heavier stream 411 fraction, and 15% was in the lighter stream 407 fraction. FIG. 13 shows that the carbon chain lengths of the products were increased relative to the feed. In general these components have continuous carbon backbones and can be hydrogenated to form gasoline, kerosene, and diesel fuels.

Example 10

The organic products from Example 9 were fed over a commercially available nickel hydrotreating catalyst to hydrogenate remaining oxygenates and alkenes. Both stream 407 and 411 were fed to the hydrotreater. The hydrotreating catalyst was loaded as a packed bed with 20" height in a 1" diameter shell and tube reactor with silicon carbide co-load in a 1:1 ratio. The reaction was run at 300° C., 800 psig, weight hour space velocity of 1.0 hr$^{-1}$, and a hydrogen co-feed of 4:1. The product produced was >98% fully saturated hydrocarbons.

Example 11

Figure 14:
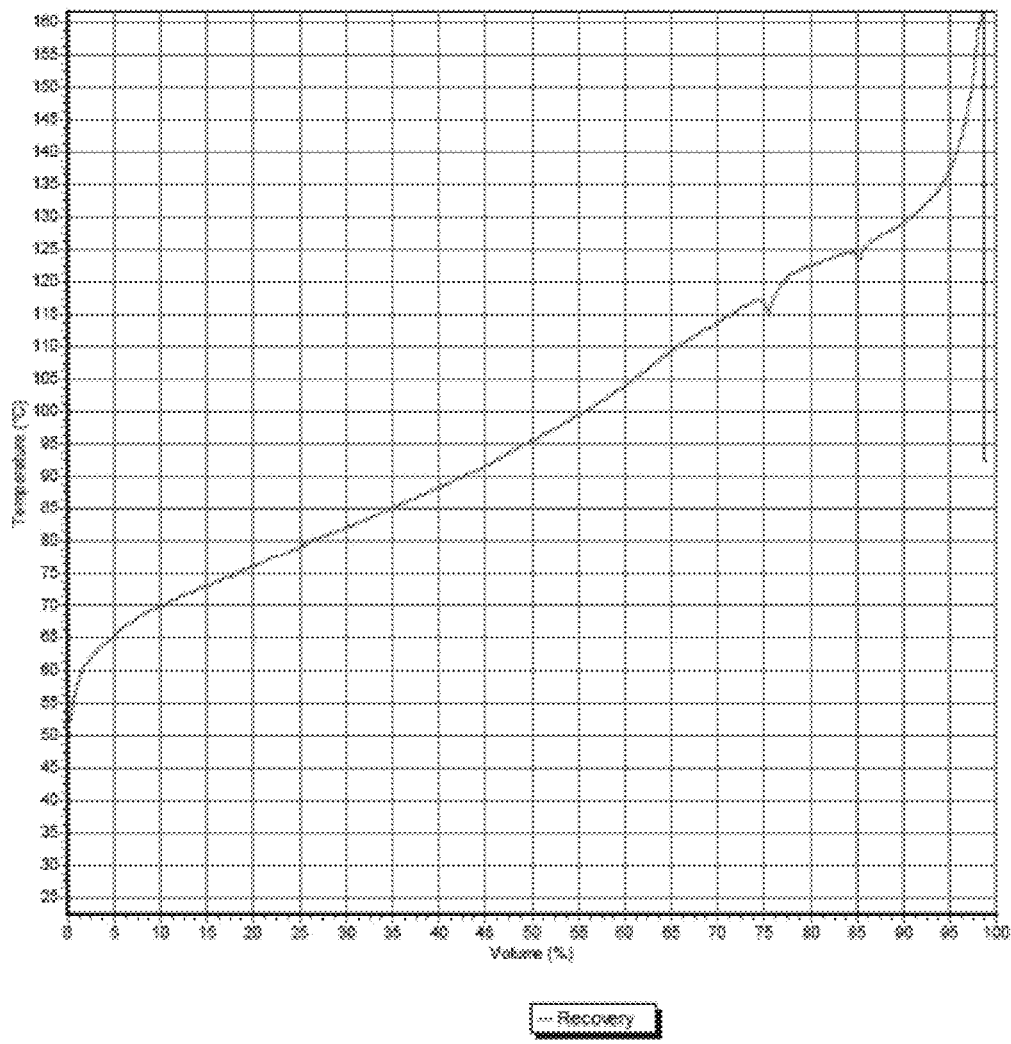
FIG. 14 is a graph providing the distillation curve for the gasoline fraction derived from the conversion of volatile $C_{2+}O_{1-2}$ oxygenates over a Pd:Ag condensation catalyst.

The hydrotreated product from Example 10 was fractionated using standard distillation techniques to produce a gasoline product. The sample had an initial boiling point of 48° C. and an endpoint of 163° C. as determined by ASTM method D86. The distillation curve from the test is shown in FIG. 14. Roughly 20% of the hydrotreated material was contained in this product fraction.

Example 12

Figure 15:
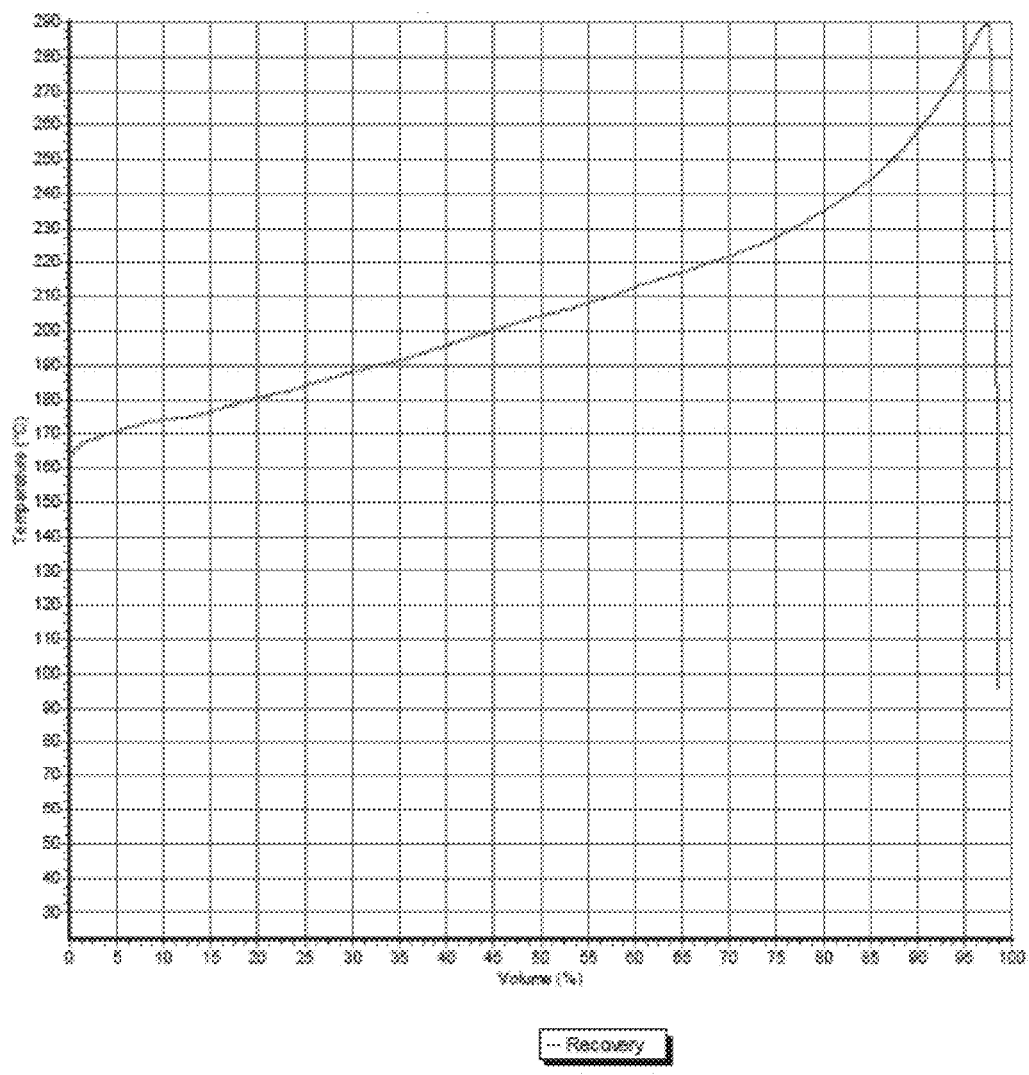
FIG. 15 is a graph providing the distillation curve for the kerosene fraction derived from the conversion of volatile $C_{2+}O_{1-2}$ oxygenates over a Pd:Ag condensation catalyst.

The hydrotreated product from Example 10 was fractionated using standard distillation techniques to produce a kersoene product. The sample had an initial boiling point of 163° C. and an endpoint of 292° C. as determined by ASTM method D86. The distillation curve from the test is shown in FIG. 15. The sample had a flashpoint of 50° C. as determined by ASTM method D56. Roughly 50% of the hydrotreated material was contained in this product fraction.

Example 13

Figure 16:
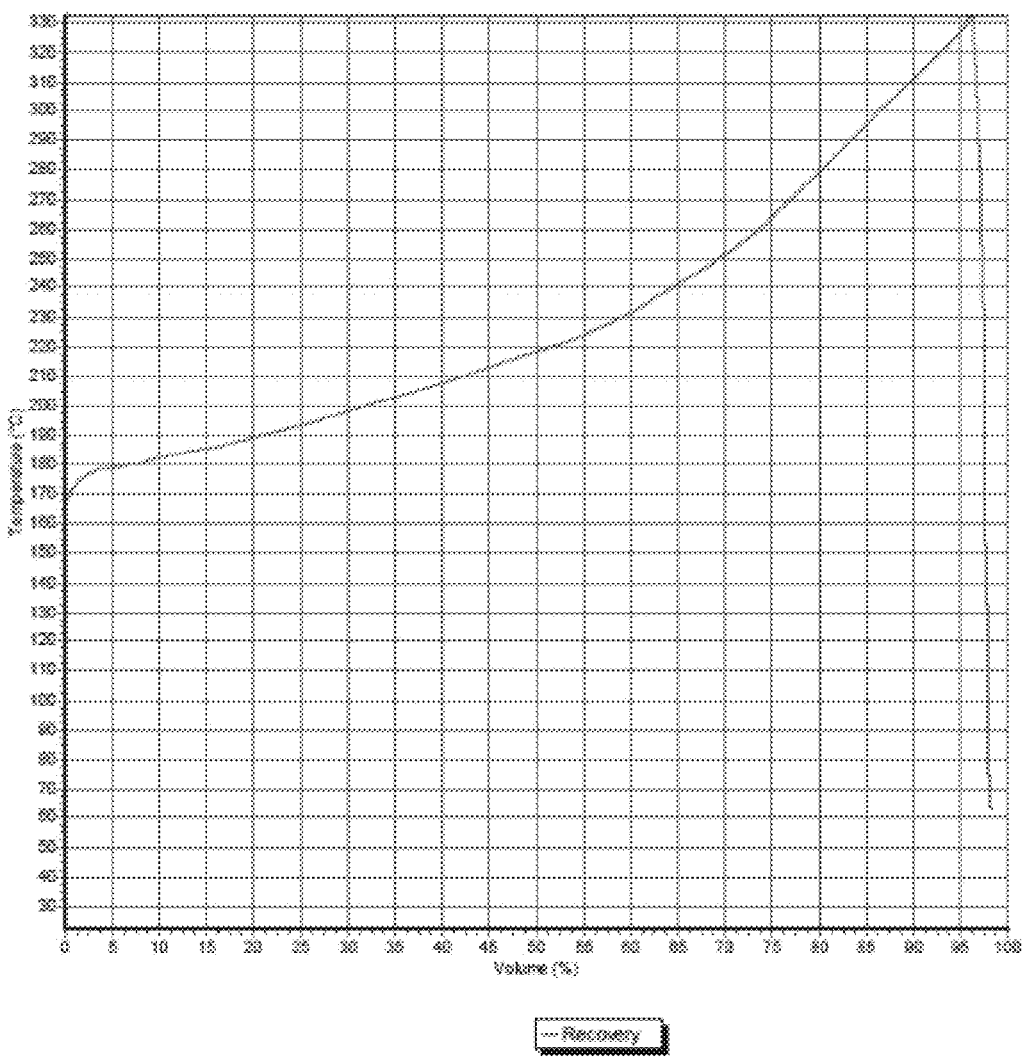
FIG. 16 is a graph providing the distillation curve for the diesel fraction derived from the conversion of volatile $C_{2+}O_{1-2}$ oxygenates over a Pd:Ag condensation catalyst.

The hydrotreated product from Example 10 was fractionated using standard distillation techniques to produce a diesel product. The sample had an initial boiling point of 167° C. and an endpoint of 334° C. as determined by ASTM method D86. The distillation curve from the test is shown in FIG. 16. The sample had a flashpoint of 56° C. as determined by ASTM method D56. Roughly 60% of the hydrotreated material was contained in this product fraction.

Example 14

A mixture of volatile C$_{2+}$O$_{1-2}$ oxygenates similar to those produced in Examples 2 and 3 were converted to fuel and chemical products using a condensation catalyst according to the process of the present invention. Table 5 shows the carbon number distribution and component classification of the components contained within the volatile oxygenate mixture fed into the condensation reactor.

TABLE 5

Composition of Oxygenate Mixture Fed into Condensation Reactors (wt %)

| Carbon Number | Water | Alkanes | Ketones | Alcohols | Other Mono-Oxygenates | Furans | Di-oxygenates | Diols | Acids |
|---|---|---|---|---|---|---|---|---|---|
| 0 | 65.8 | | | | | | | | |
| 1 | | | | 0.6 | | | | | |
| 2 | | | | 4.0 | | | | | 0.4 |
| 3 | | | 0.5 | 3.8 | | | 0.1 | 0.4 | 0.4 |
| 4 | | 0.1 | 0.2 | 3.0 | 0.7 | 0.3 | 0.2 | 1.9 | 0.5 |
| 5 | | 0.2 | 1.0 | 2.4 | 0.1 | 2.8 | 0.1 | | 0.4 |
| 6 | | 0.5 | 0.9 | 1.9 | 0.7 | 5.4 | 0.3 | | 0.3 |

The mixed volatile oxygenate feed was converted to hydrocarbons using the catalyst described in Example 5 and two 1" OD downflow reactors connected in series, with each containing fixed catalyst beds approximately 11" in length. The process conditions are shown in Table 6. The products from this experiment were analyzed by methods described in Example 1. The components produced from this experiment were primarily hydrocarbons having the overall composition shown in Table 7.

TABLE 6

Condensation Reactor Conditions

| Condition | Units | Value |
|---|---|---|
| Catalyst | | 1% Ni on ZSM-5 (SAR 30, 20% Al2O3 Binder, 1/16" Extrudates) |
| Total Catalyst Weight | g | 147 |
| Feed Rate | g/min | 2.35 |
| Lead Reactor Temperature | ° C. | 361 |
| Lag Reactor Temperature | ° C. | 340 |
| Pressure | psig | 75 |

TABLE 7

Breakdown of Condensation Reactor Outlet Composition

| Component | wt % of Intermediate Feed Carbon |
|---|---|
| Alkanes | 34.9 |
| Aromatics | 53.6 |
| Alkenes | 7.1 |
| Cycloalkanes | 3.8 |
| Dienes | 0.6 |

Example 15

The product from Example 14 was distilled using well know laboratory scale distillation equipment. As shown in Table 8, the majority of the product stream included compounds in the gasoline boiling range. The gasoline boiling range for this experiment was described as having an initial boiling point of 28° C. and a final boiling point of 176° C.

TABLE 8

Acid Condensation Product Distribution after Gasoline Fractionation

| Component | wt % of Intermediate Feed Carbon | wt % of Intermediate Product Weight |
|---|---|---|
| Light Gas | 18.1 | — |
| Heavy Organic | 5.6 | — |
| Gasoline | 76.3 | — |
| Alkanes | — | 28.5 |
| Aromatics | — | 61.2 |
| Alkenes | — | 4.5 |
| Cycloalkanes | — | 5.1 |
| Dienes | — | 0.7 |

The product from Example 14 was also distilled using well know laboratory scale distillation equipment in such a way to provide a product high in $C_8$ aromatics ($A_8$). The resulting product contained a total of 97.3% $C_8$ aromatics, including 14.4 wt % ethylbenzene, 23.1% para xylene, 48.4% meta xylene, and 10.5% ortho xylene. This material is similar in composition to a mixed $C_8$ aromatic stream that is used as feedstock for industrially practiced production of aromatic chemicals.

Example 16

A deconstruction catalyst containing 2% Pd, 2% Ru, and 13.5% W on a monoclinic zirconia support was used for the deconstruction of corn stover. Water was used as the initial solvent followed by the recycle of residual $C_{2+}O_{2+}$ oxygenated hydrocarbons from the liquid phase. A feed stream containing 10% (w/v) of water washed corn stover with a 1:3 catalyst to biomass ratio was fed to a reactor system operating at 250° C.-285° C. and 950 psig-1100 psig $H_2$. Fresh catalyst was used for the first two rounds of recycle, after which regenerated catalyst was used. Catalyst preparation and regeneration conditions are shown in Table 9.

TABLE 9

Catalyst Preparation and Regeneration

| Catalyst #FCC78 | Calcination | Reduction | Passivation | Regeneration |
|---|---|---|---|---|
| Flowing Gas | Air | H2 | <3% O2 in N2 Environment | <3% O2 in N2 Environment |
| Temperature | 400° C. | 350° C. | <35° C. | 450° C. |
| Ramp | 1.6° C./min | 2.7° C./min | N/A | 1.25° C./min |
| Soak | 6 hrs | 2 hrs | 2 hrs | 16 hrs |

Figure 17:
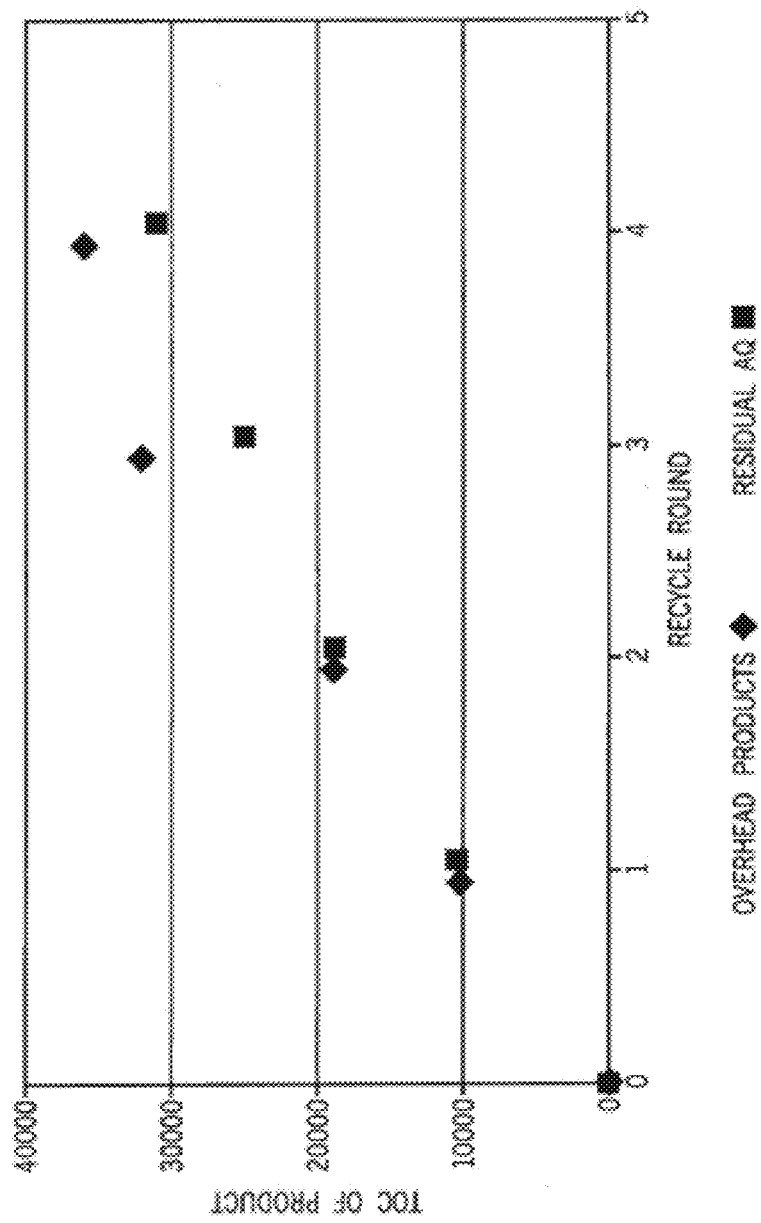
FIG. 17 is a graph providing the total organic carbon (TOC) in the liquid phase from the conversion of a biomass feed stream containing corn stover with recycle according to the present invention.
Figure 18:
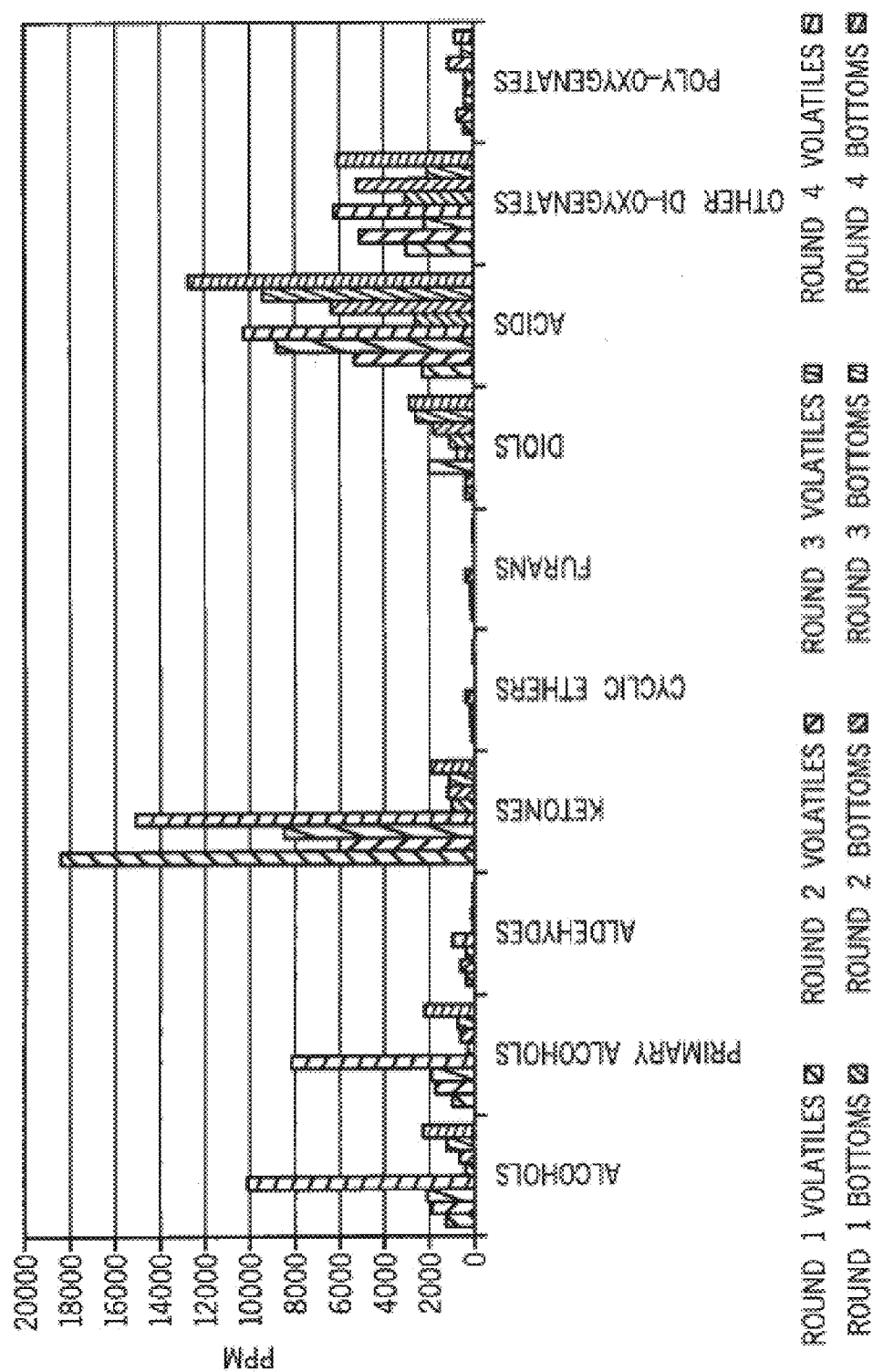
FIG. 18 is a graph providing the identified aqueous product distribution of the volatile and bottoms from the conversion of a biomass feed stream containing corn stover with recycle according to the present invention.

Recycling of the liquid phase fraction led to a steady increase of total organic carbon (TOC) in the liquid product stream by adding more biomass carbon to the solvent as shown in FIG. 17. FIG. 18 illustrates the changing product distribution during each round of recycle in both the volatile $C_{2+}O_{1-2}$ oxygenates and bottoms fractions. The volatile $C_{2+}O_{1-2}$ oxygenates fractions show a high amount of alcohols and ketones as well as short chained acids compared to the more oxygenated species left in the bottoms fraction. The increasing acids trend is an accumulation of acetic acid from the biomass, particularly the hemicellulose, rather than a selectivity trend from the catalyst.

Example 17

A deconstruction catalyst containing 2% Pd, 2% Ru, and 13.5% W on a monoclinic zirconia support was used for the deconstruction of corn stover in a hydrodeoxygenation (HDO) derived solvent (60% (w/v) corn syrup over a trimetallic catalyst), followed by recycle of the residual liquid stream, i.e., the $C_{2+}O_{2+}$ oxygenated hydrocarbons not collected through vapor phase sampling. A feed stream containing 10% (w/v) water washed corn stover in solvent with a 1:3 catalyst to biomass ratio was fed to a reactor system operating at 250° C.-285° C. and 950 psig-1100 psig $H_2$. Fresh catalyst was used for the first two rounds of recycle followed by catalyst regeneration for rounds three and four. The catalyst was regenerated according to the conditions outlined in Table 9.

Figure 19:
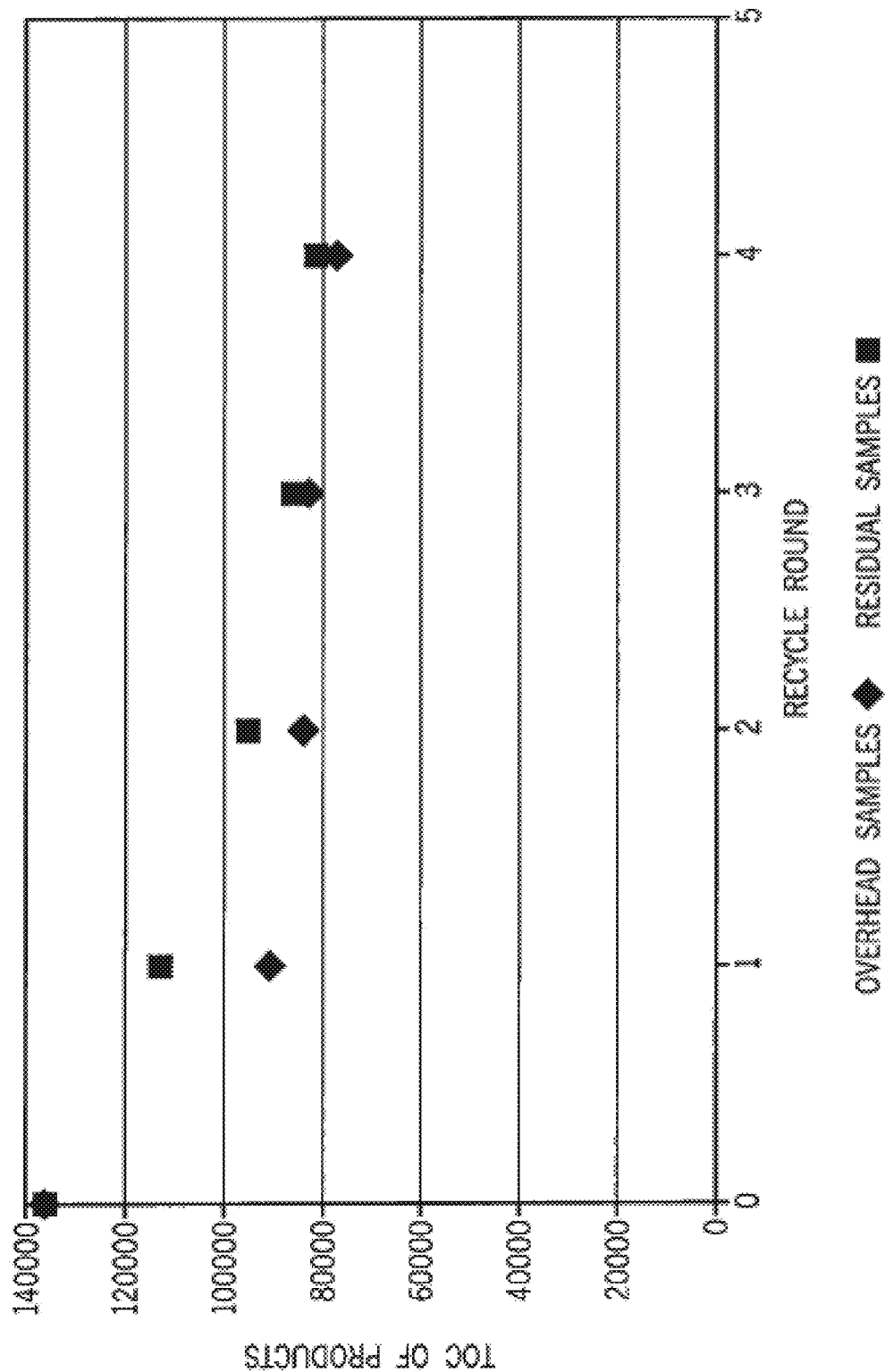
FIG. 19 is a graph providing the TOC from the conversion of a biomass feed stream containing corn stover with recycle according to the present invention.
Figure 20:
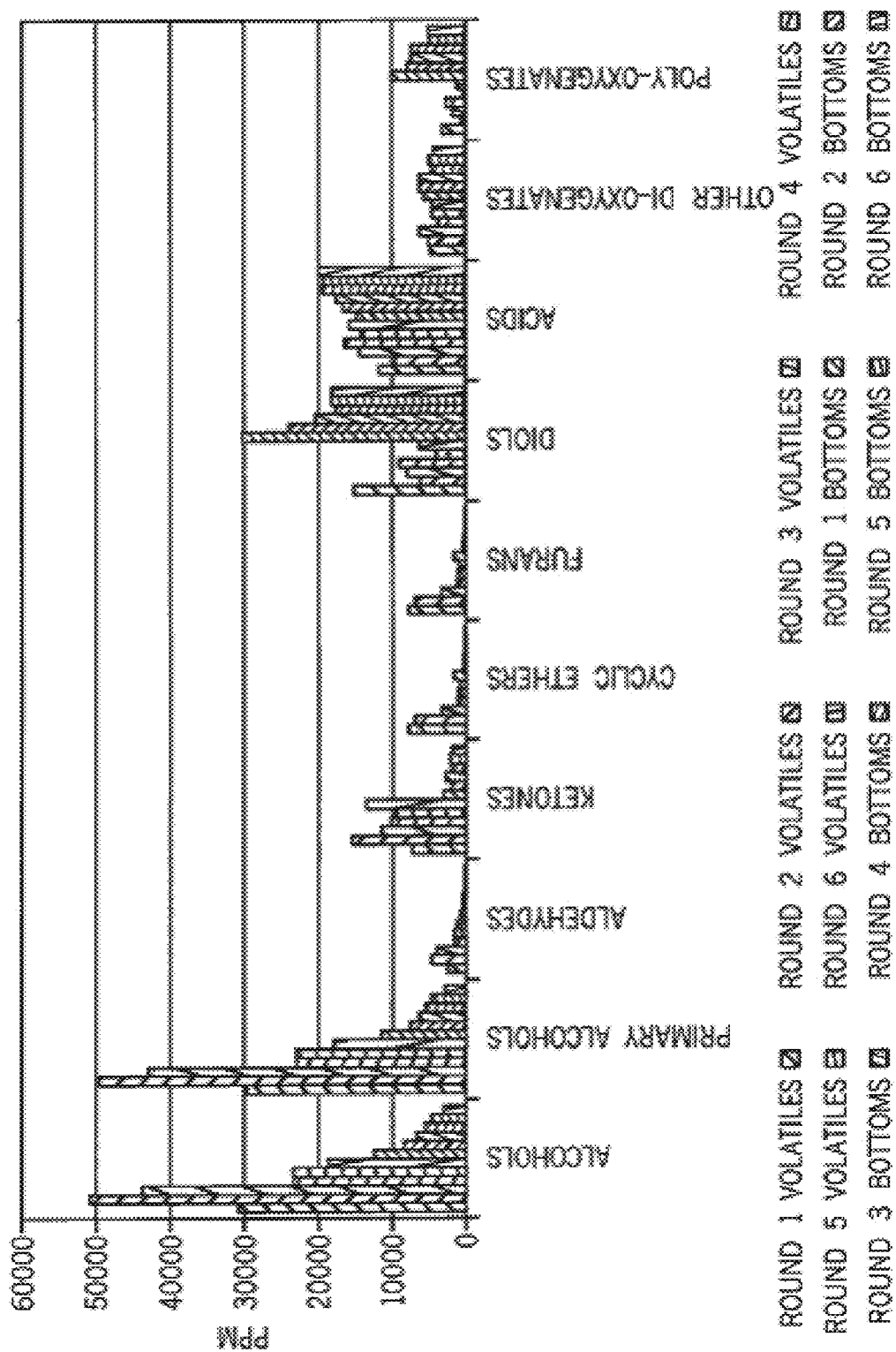
FIG. 20 is a graph providing the identified aqueous product distribution of the volatiles and bottoms from the conversion of a biomass feed stream containing corn stover with liquid phase recycle according to the present invention.
Figure 21:
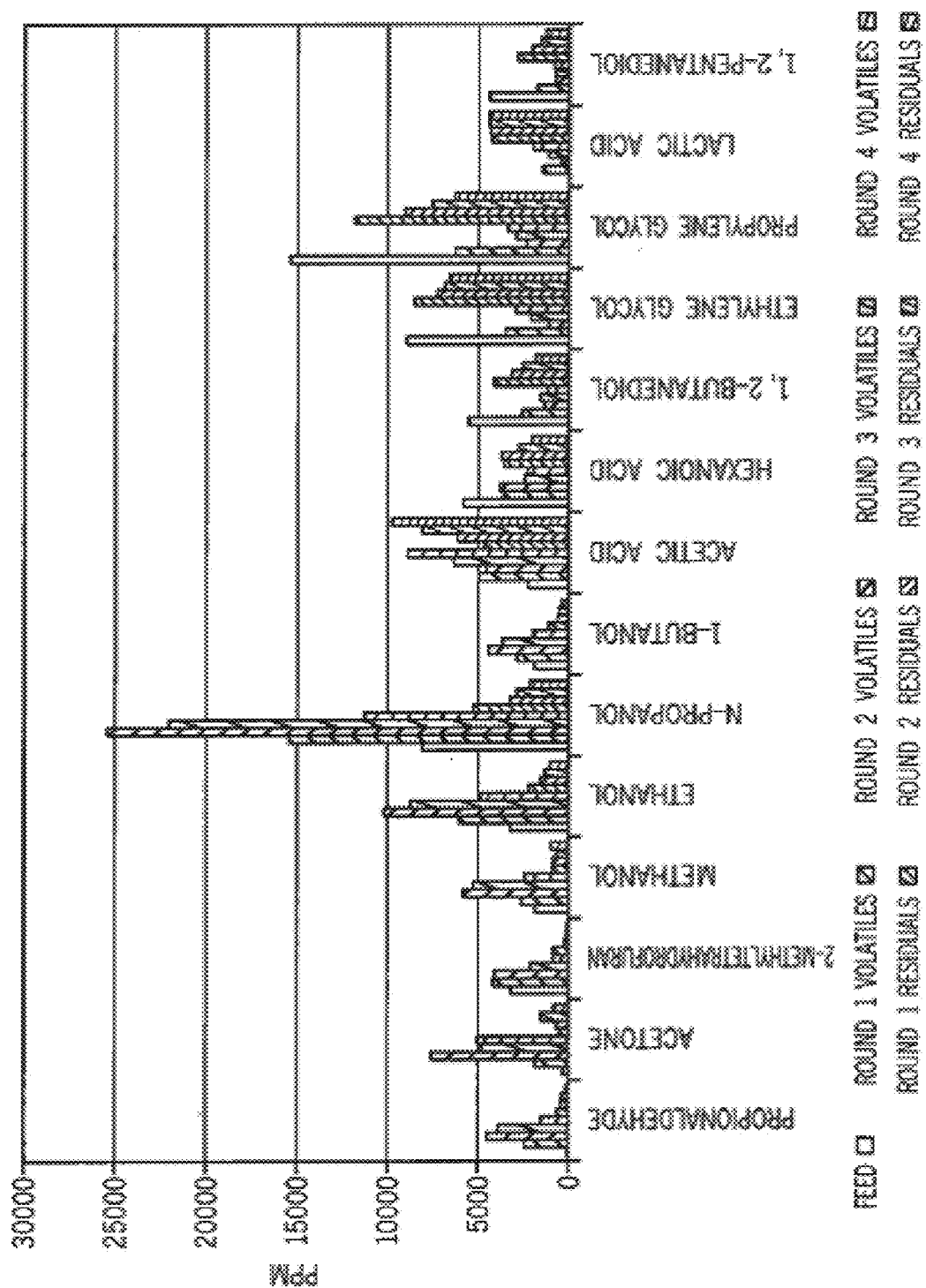
FIG. 21 is a graph providing the most abundant aqueous product speciation from the conversion of a biomass feed stream containing corn stover with liquid phase recycle according to the present invention.
Figure 22:
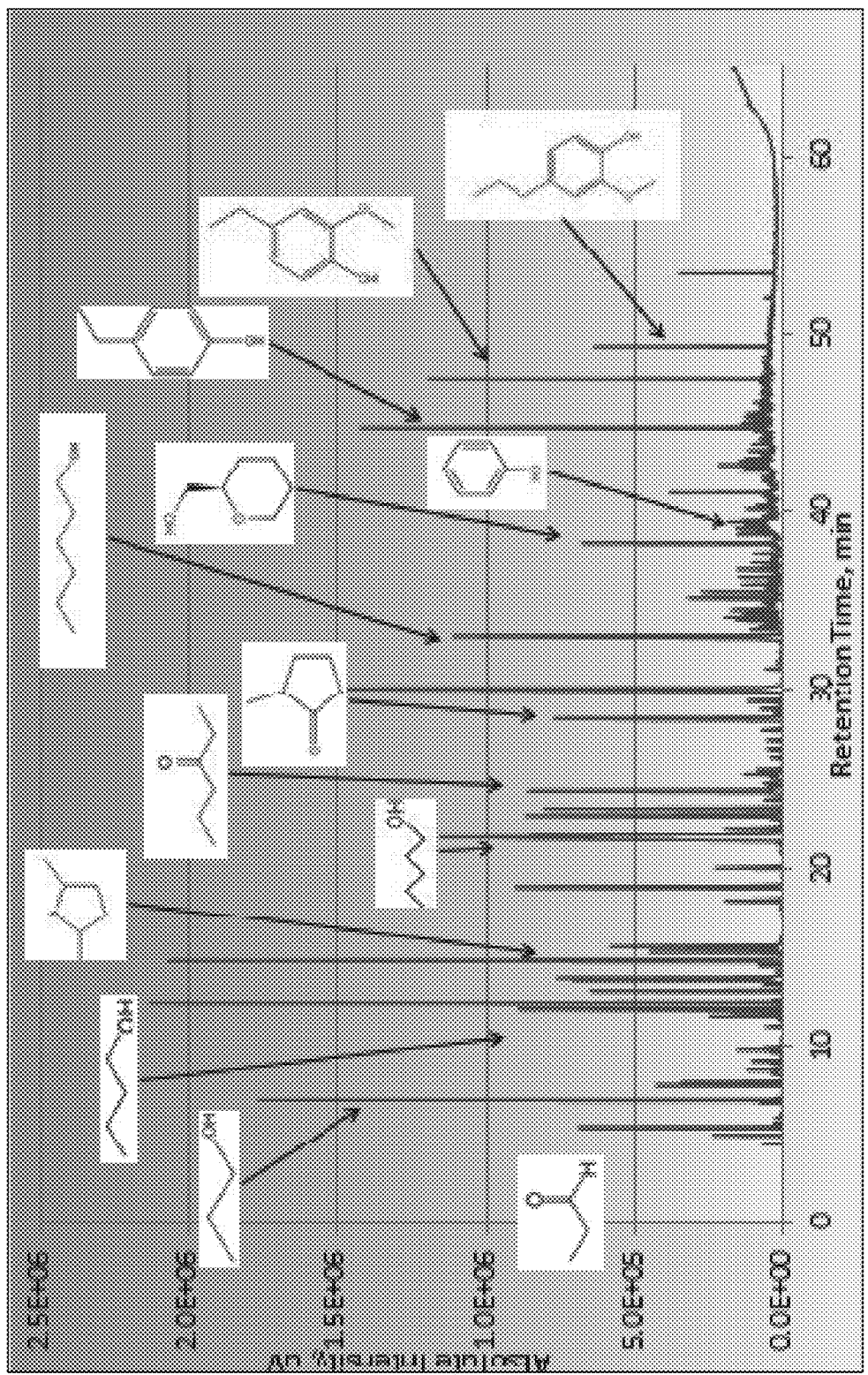
FIG. 22 is a graph providing identified condensable organic products present in the vapor phase from the deconstruction of a biomass feed stream containing corn stover according to the present invention.

FIG. 19 illustrates the effect of aqueous recycle on TOC in the aqueous product stream. FIG. 20 illustrates the effect of aqueous recycle on the product distribution in both the volatile oxygenates and bottoms fractions, specifically the $C_{2+}O_{1-2}$ oxygenates in the volatile fraction and the diols and poly-oxygenates in the bottoms (liquid phase used as the recycle solvent). FIG. 21 illustrates the product speciation of the aqueous phase including specific compounds and the increase in TOC over time. A representative condensable vapor phase is shown in FIG. 22.

Example 18

Figure 23:
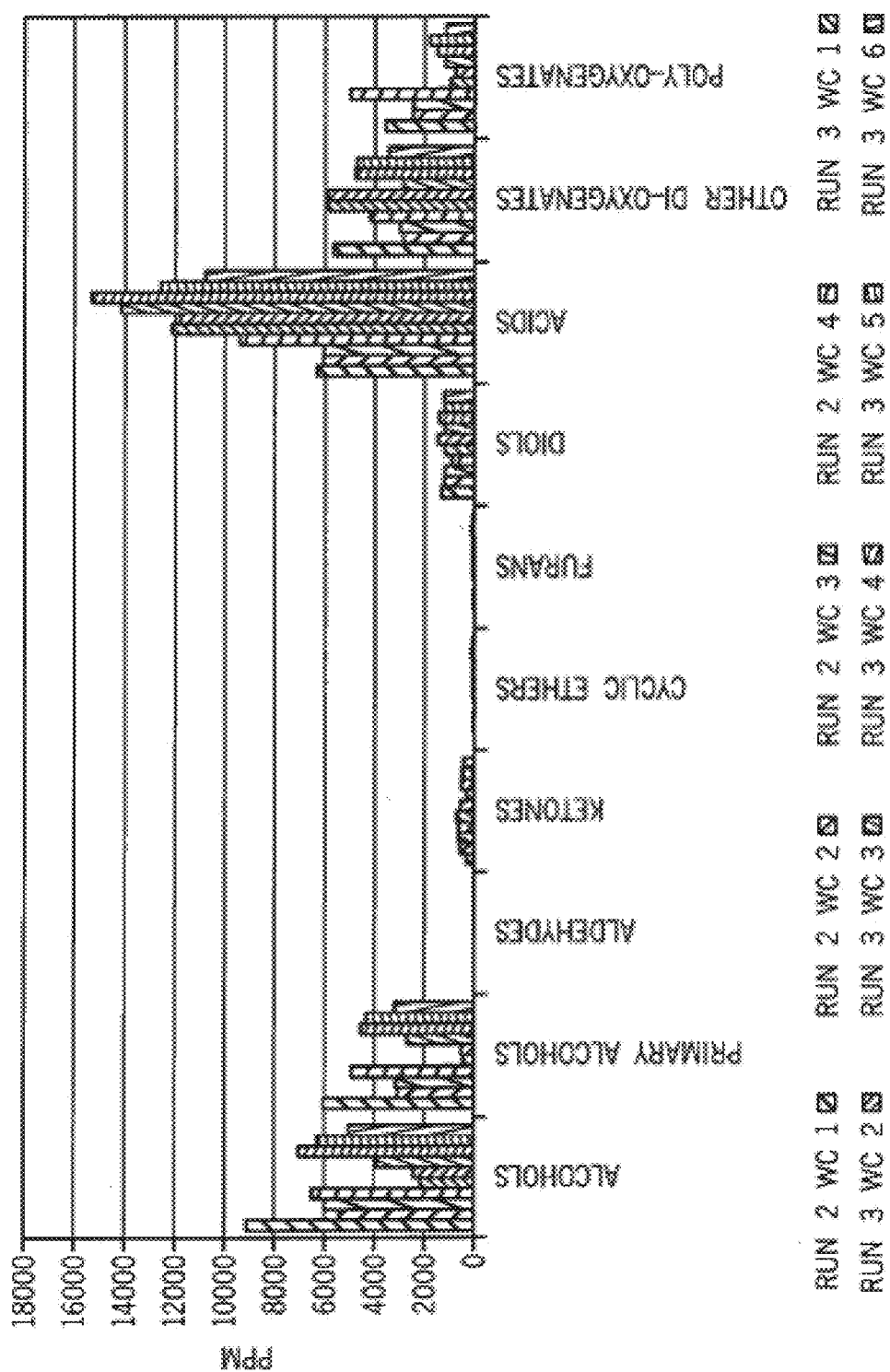
FIG. 23 is a graph providing the identified aqueous product distribution from the deconstruction of a biomass feed stream containing MCC under two different processing conditions according to the present invention.
Figure 24:
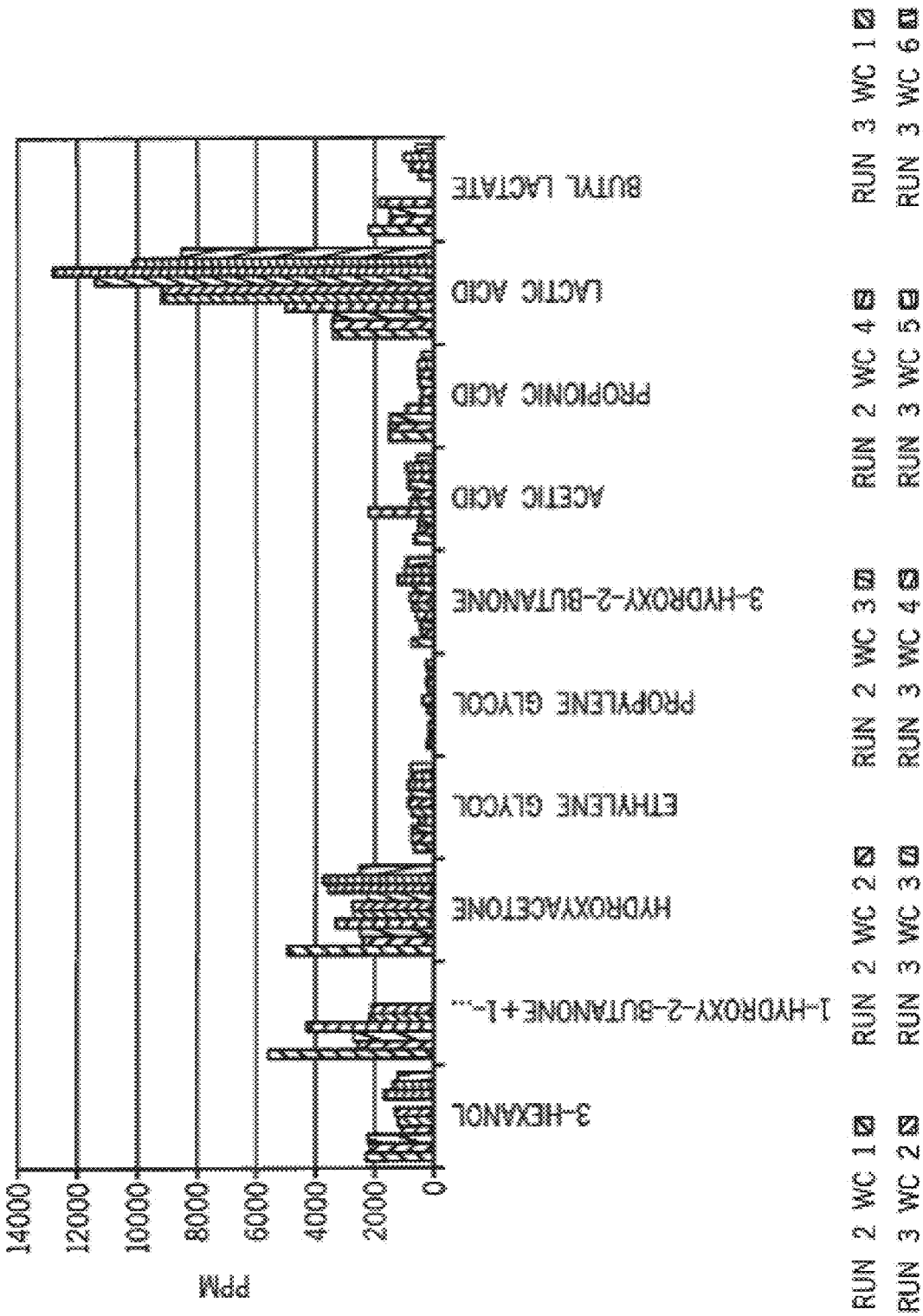
FIG. 24 is a graph providing the most abundant aqueous product speciation from the deconstruction of a biomass feed stream containing MCC under two different processing conditions according to the present invention.

A deconstruction catalyst containing 2% Pd and 2% Ag on a tungstated zirconia support was used for deconstruction of MCC. Reactor conditions were 10% (w/v) MCC in water, 1:3 catalyst:MCC, 240° C.-285° C. (Run 2 240° C.-275° C., Run 3 260° C.-285° C.), and 950 psig-1050 psig $H_2$. Fresh catalyst was used for Run 2 with a combination of fresh catalyst and regenerated catalyst used for Run 3 at a fresh catalyst to regenerated catalyst ratio of 1:1. Product distribution and speciation are summarized in FIGS. 23 and 24, respectively.

Example 19

Figure 25:
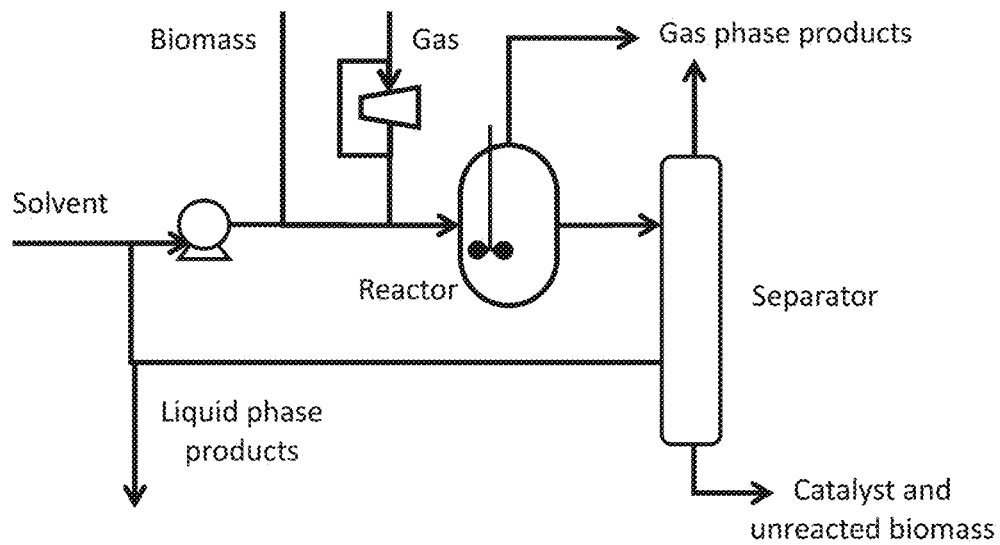
FIG. 25 is a flow diagram illustrating one embodiment of the present invention.

A biomass feed stream containing 10% (w/v) MCC in water was converted to gas phase containing volatile $C_{2+}O_{1-2}$ oxygenates and a liquid phase containing $C_{2+}O_{2+}$ oxygenated hydrocarbons using a deconstruction catalyst containing 2% Pd and 2% Ag on a tungstated monoclinic zirconia support. The reaction was carried out in a system similar to the configuration illustrated in FIG. 25. The reactor was operated at a temperature of 240° C. 280° C. and a pressure of 1000 psig with a residence time of 10 minutes. The products from the reaction were analyzed as outlined in Example 1. The carbon number distribution and component classification of the product liquid are summarized in Table 10.

TABLE 10

Composition of Oxygenate Mixture Fed into Condensation Reactor (wt %)

| Carbon Number | Water | Ketone | Alcohol | Furan | Dioxygenate | Polyoxygenate | Diol | Acid |
|---|---|---|---|---|---|---|---|---|
| 0 | 94.4 | | | | | | | |
| 1 | | 0.03 | | | | | | |
| 2 | | | | | | 0.01 | 0.07 | 0.06 |
| 3 | | 0.01 | 0.00 | | 0.49 | 0.38 | 0.02 | 0.15 |
| 4 | | | | | 0.08 | 0.00 | 0.03 | 0.01 |
| 5 | | 0.01 | 0.00 | 0.00 | | 0.06 | | 0.01 |
| 6 | | 0.01 | 0.81 | 0.03 | | 0.01 | 0.01 | 0.02 |
| 7 | | | | | | 0.22 | | 0.02 |
| 8 | | | | | | | | |
| 9 | | 0.07 | | | | | | |

Figure 26:
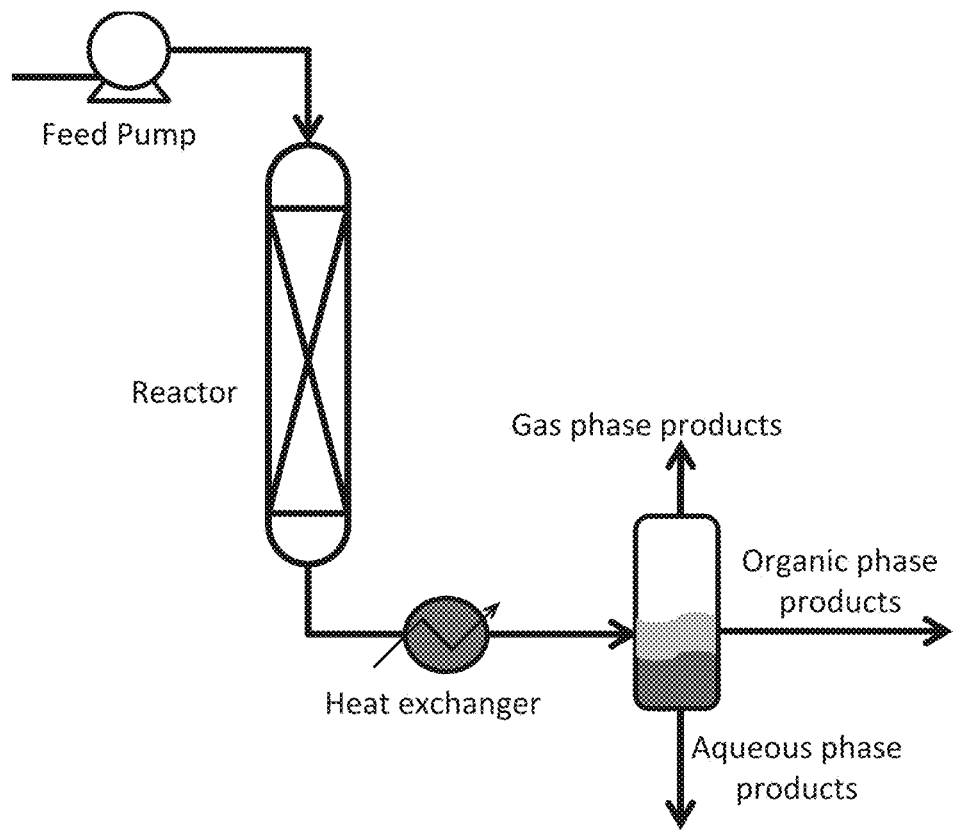
FIG. 26 is a process flow diagram illustrating one of several process configurations for conducting the condensation reactions to produce aromatics according to the present invention.
Figure 27:
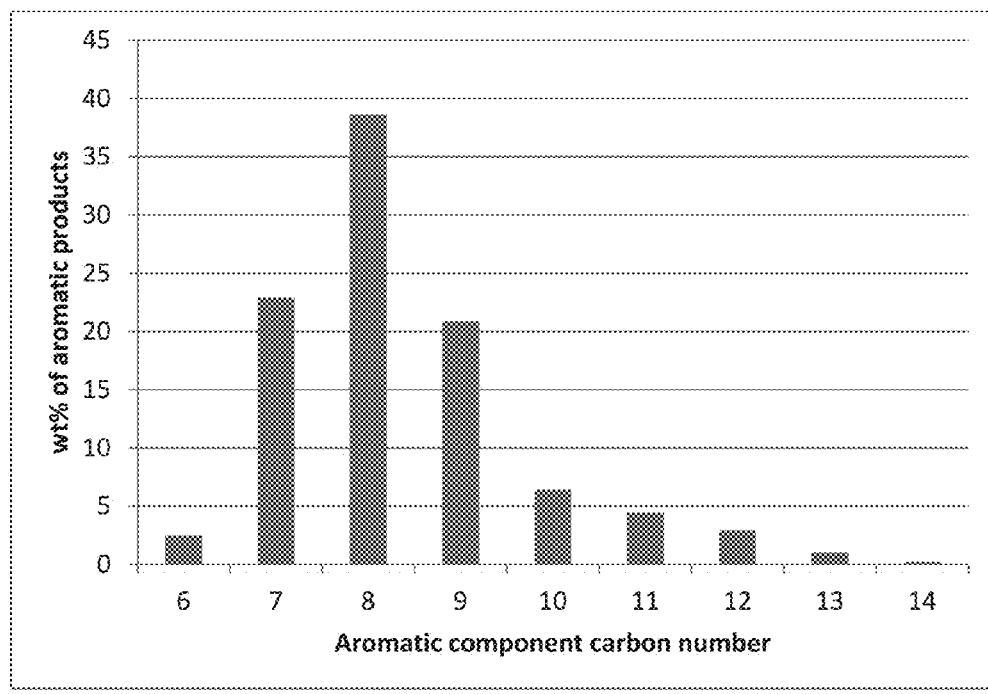
FIG. 27 is a graph providing the carbon number distribution for aromatics produced from the deconstruction of a biomass feed stream containing MCC according to the present invention.

The mixed oxygenate feed was converted to hydrocarbons in a ½" ID downflow reactor loaded with the catalyst described in Example 5. The reactor system is illustrated in FIG. 26. The reactor was operated at a temperature of 385° C., a pressure of 75 psig, and a WHSV of 0.2 hr$^{-1}$. The products from this experiment were analyzed using the methods described in Example 1. Aqueous, organic and gas phase products were recovered resulting in approximately 90% conversion of carbon in the aqueous phase. The organic phase product contained 92.4 wt % aromatic components, suitable for use as chemicals or a gasoline blendstock, with a carbon number distribution shown in FIG. 27.

Example 20

Three separate biomass feed streams (corn stover, loblolly pine and sugarcane bagasse) were converted to a gas phase containing volatile $C_{2+}O_{1-2}$ oxygenates and a liquid phase containing $C_{2+}O_{2+}$ oxygenated hydrocarbons using a deconstruction catalyst containing palladium, molybdenum, and tin supported on tungstated zirconia in a staged two reactor system. A deconstruction solvent of similar composition to the residual liquid phase from Example 2 was used as a contact carrier between the biomass and deconstruction catalyst.

Dependent upon particle size and density, 25-45 grams of biomass and 70 grams of deconstruction catalyst were loaded as packed beds to a height of 12" and a 1" diameter. The first deconstruction reactor was operated with a temperature ramp from 120-310° C. and a pressure of 1200 psi to allow for pressure driven transfer to the second reactor, which was operated at 1050 psi and a temperature ramp of 180-270° C. The deconstruction solvent was fed to the system at a rate of 2.9 g/min, resulting in a weight hourly space velocity (WHSV) of 3.9-6.9 g solvent/g biomass per hour (dependent on the mass loaded) or 2.5 g solvent/g catalyst per hour. Hydrogen was co-fed at a rate of 1.9 mol/hr.

Figure 28:
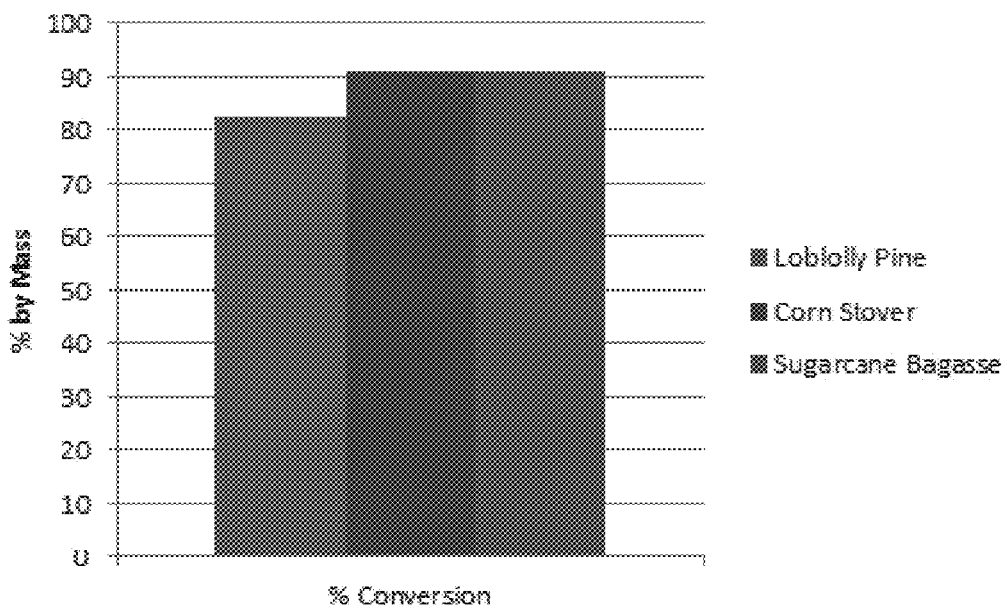
FIG. 28 is a graph providing the conversion data for three biomass feed streams according to the present invention.
Figure 29:
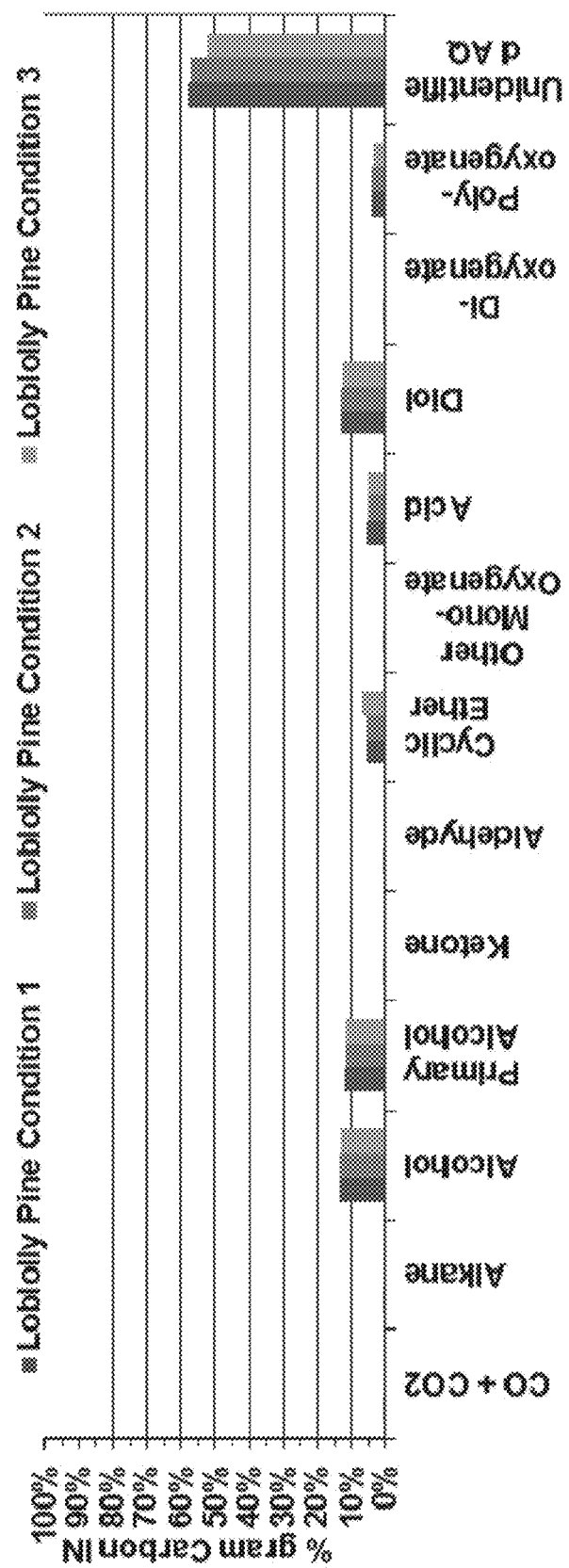
FIG. 29 is a graph providing the identified aqueous product distribution for the conversion of a biomass feed stream containing loblolly pine under different conditions according to the present invention.
Figure 30:
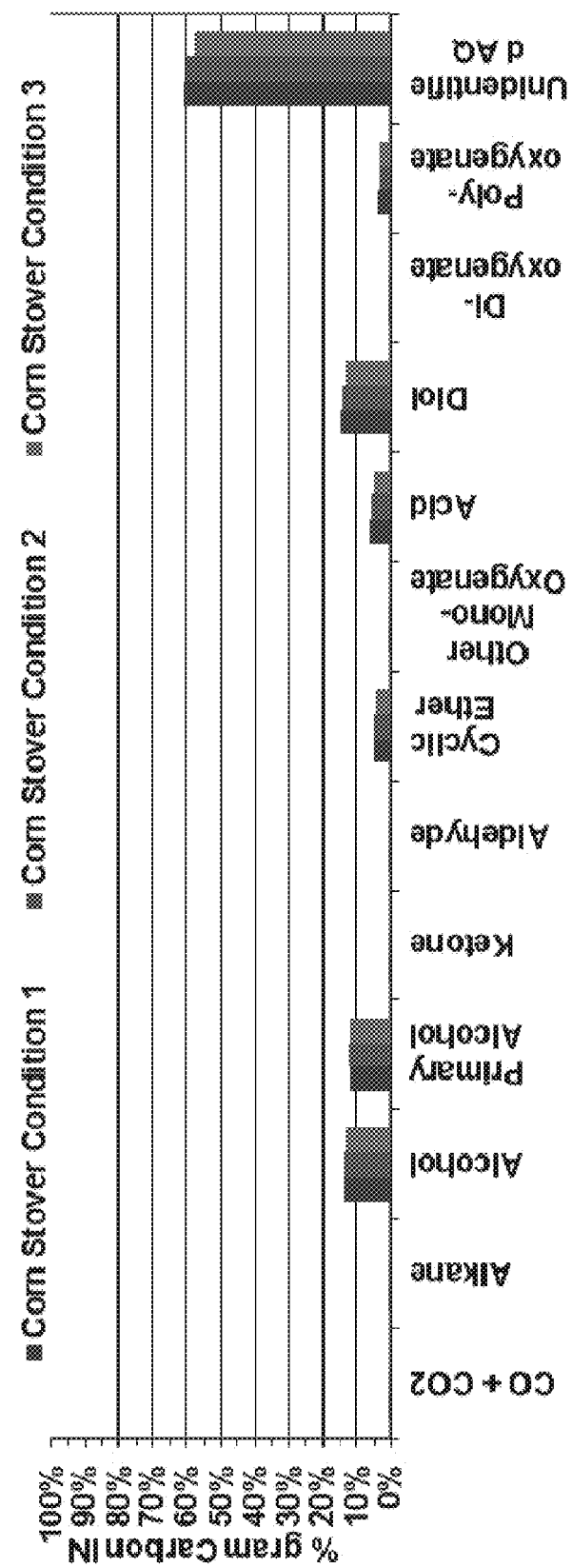
FIG. 30 is a graph providing the identified aqueous product distribution for the conversion of a biomass feed stream containing corn stover under different conditions according to the present invention.
Figure 31:
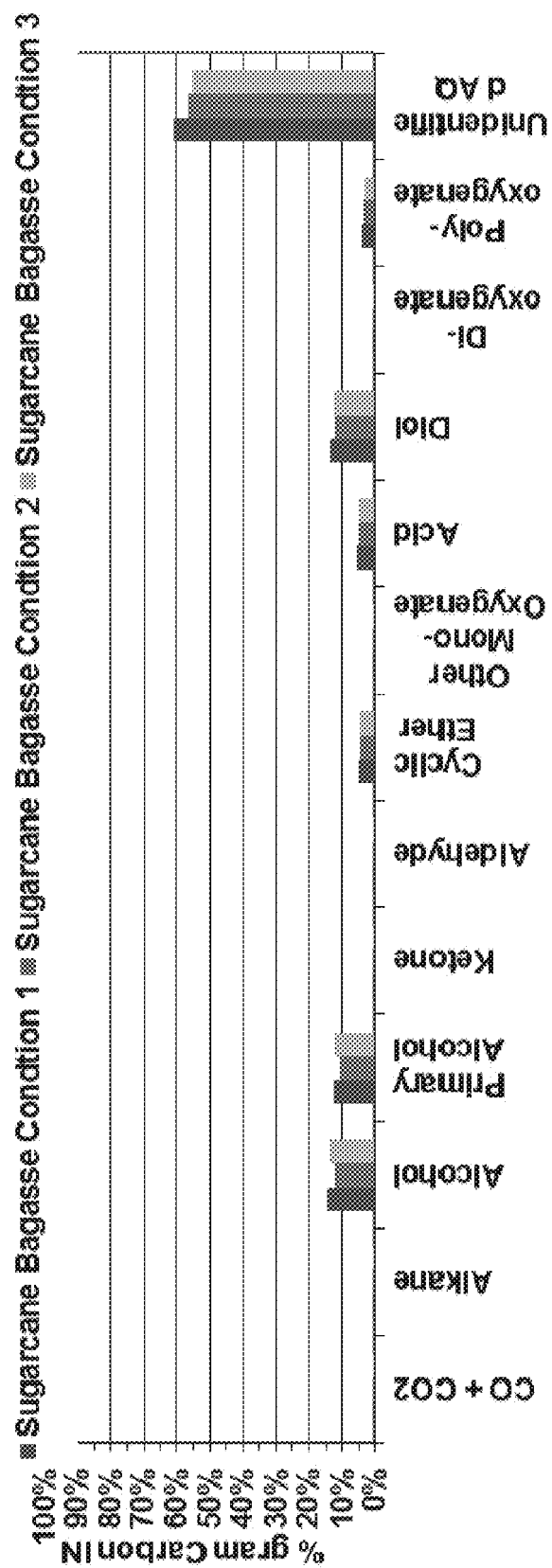
FIG. 31 is a graph providing the identified aqueous product distribution for the conversion of a biomass feed stream containing bagasse under different conditions according to the present invention.
Figure 32:
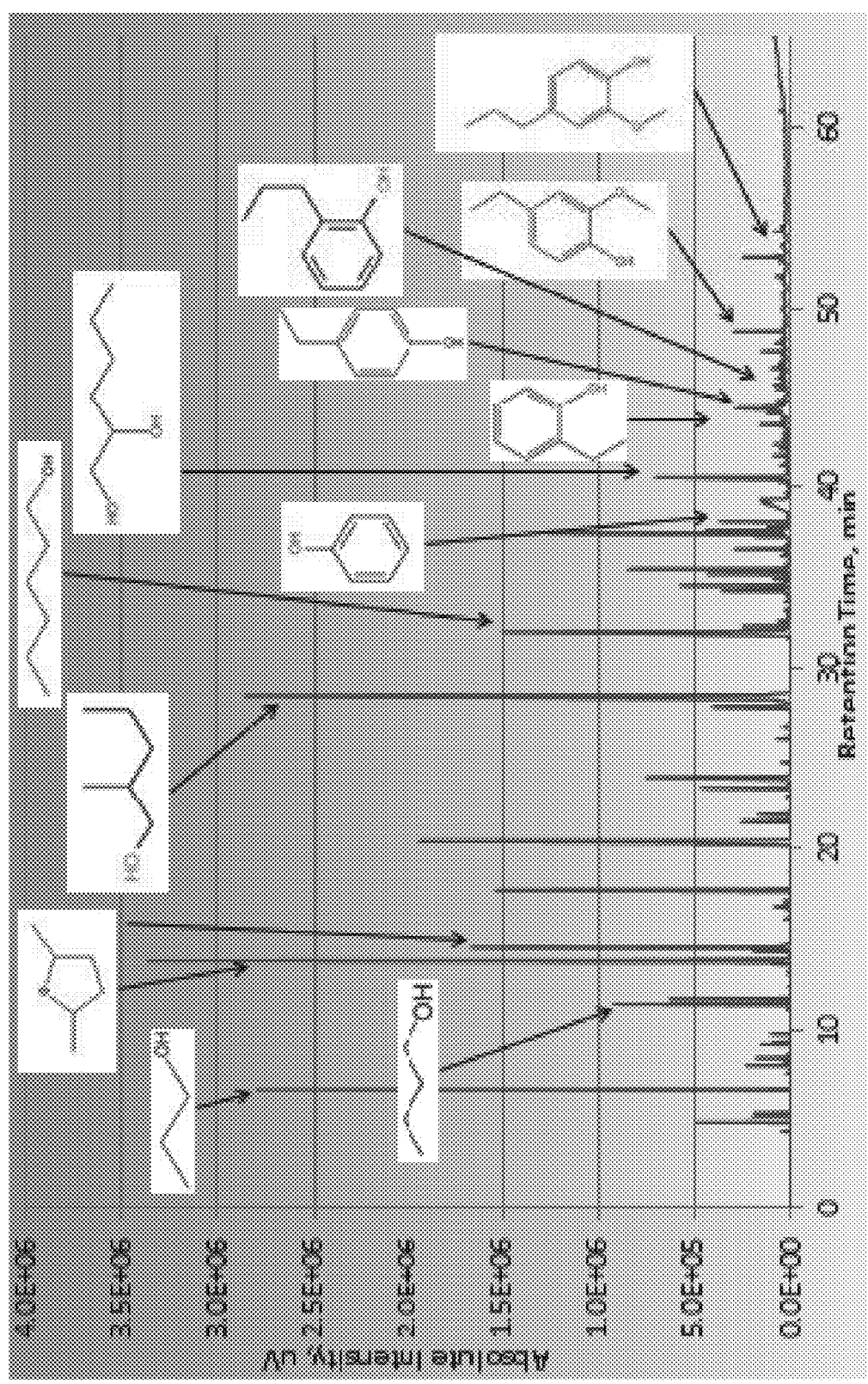
FIG. 32 is a graph providing representative condensable organic products present in the vapor phase from the deconstruction of a biomass feed stream according to the present invention.

The vapor, liquid, and organic products from the second reactor were analyzed as described in Example 1. Overall conversion for the three biomass feedstocks can be seen in FIG. 28. A combined analysis of the liquid phase product and the condensed vapor phase can be seen in FIGS. 29, 30, and 31. The unidentified liquid phase product is typically partially deoxygenated sugar species derived from the cellulose and hemicellulose components; however, some products of lignin deconstruction may also be present. A representative condensable vapor phase is shown in FIG. 32. Present in this product stream are standard cellulose and hemicellulose deoxygenation products, such as alcohols and cyclic ethers. Additionally, lignin deconstruction products are present in the form of substituted benzene components—products not seen in the deconstruction of MCC.

Example 21

A biomass feed stream containing 10 wt % bagasse in water was converted to a gas phase containing volatile $C_{2+}O_{1-2}$ oxygenates and a liquid phase containing $C_{2+}O_{2+}$ oxygenated hydrocarbons using modified nickel and palladium catalysts. The conversion was carried out in a 500 mL Parr reactor at 150-280° C. and 1010 psi for a total of 100 minutes. A catalyst chosen from Table 11 was loaded into the reactor in a 3:1 biomass to catalyst weight ratio. The catalysts used are shown in Table 11.

TABLE 11

Deconstruction Catalyst Screen

| Metal Loading | Support |
|---|---|
| 2% Pd, 2% Mo, 0.5% Sn | Tungstated Zirconia |
| 5% Ni, 0.5% B | Tungstated Zirconia |
| 5% Ni, 10% Mo, 0.5% B | Tungstated Zirconia |
| 5% Ni, 2% Ru, 1% Re | Tungstated Zirconia |

Figure 33:
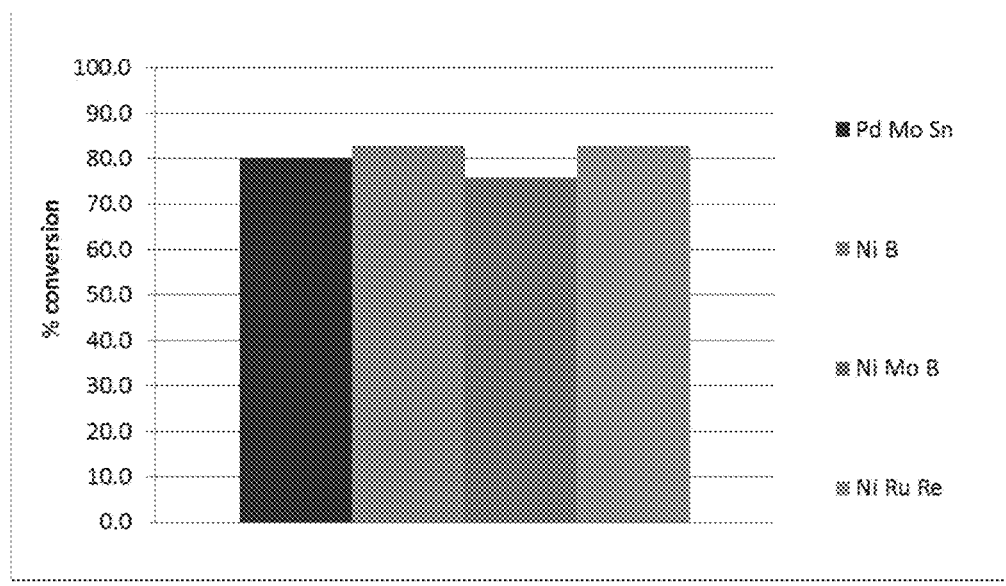
FIG. 33 is a graph providing conversion data of a biomass feed stream containing bagasse using various deconstruction catalysts according to the present invention.
Figure 34:
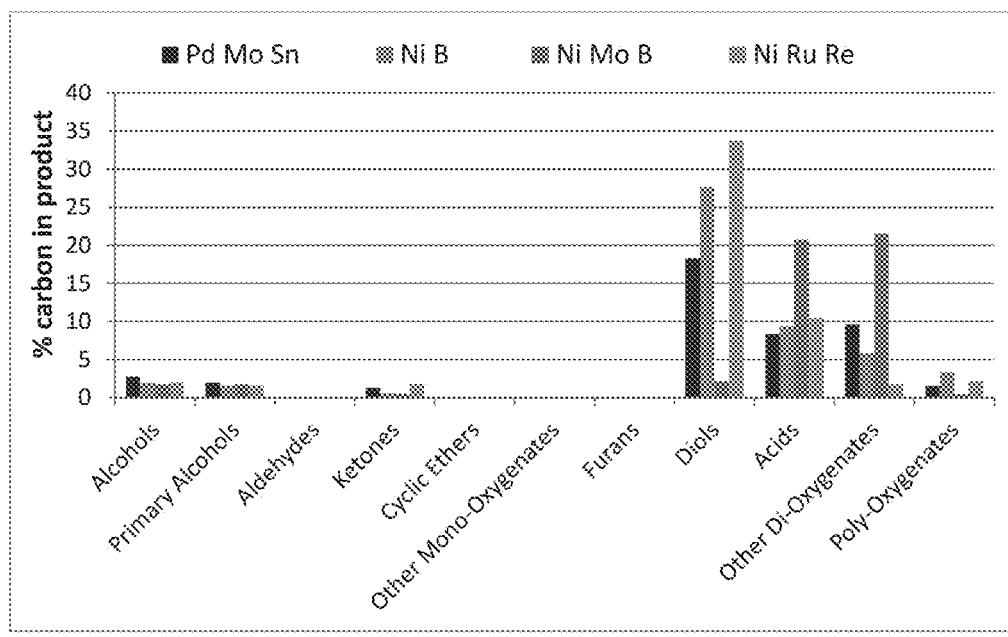
FIG. 34 is a graph providing the identified aqueous liquid phase product distribution for the deconstruction of a biomass feed stream containing bagasse using various deconstruction catalysts according to the present invention.
Figure 35:
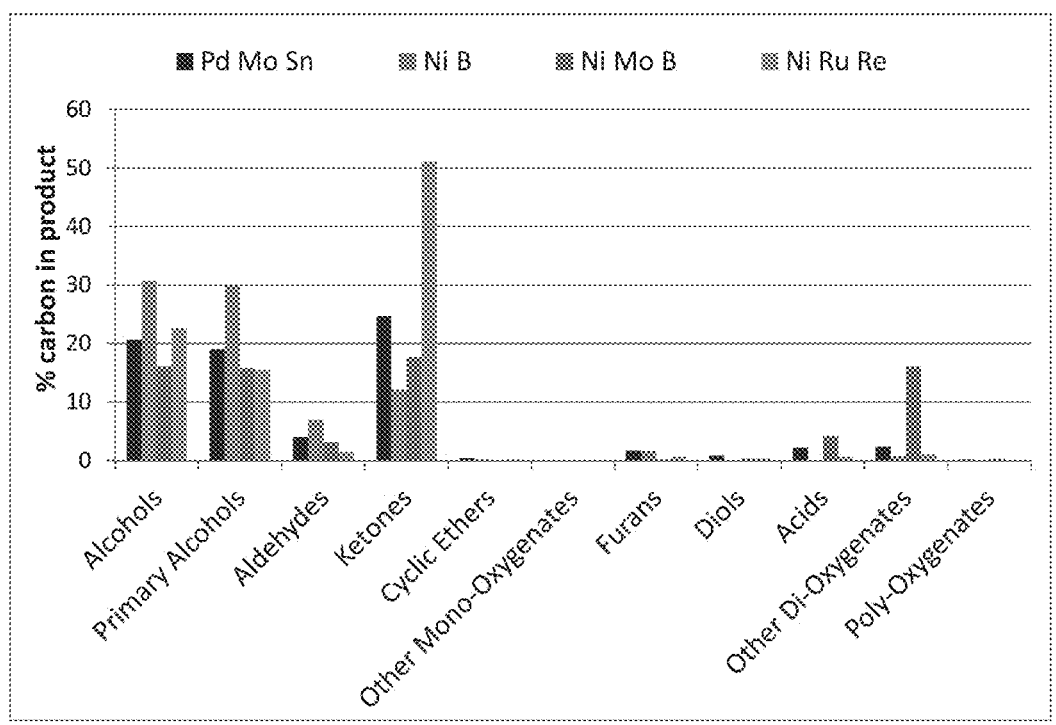
FIG. 35 is a graph providing the identified aqueous condensable product distribution present in the vapor phase for the deconstruction of a biomass feed stream containing bagasse using various deconstruction catalysts according to the present invention.

The biomass feed stream was mixed at 800 rpm for the duration of the reaction to increase mass and heat transfer throughout the entire mixture. A compressor was used to recycle approximately 2 L/min of the non-condensable gaseous product back to the reactor and draw off the condensable vapor, while fresh hydrogen was fed at 200 mL/min. The reaction was quenched after 100 min and products were analyzed by the methods outlined in Example 1. The feedstock conversion is displayed in FIG. 33. The compositions of the residual liquid phase and the condensed vapor phase stream are shown in FIGS. 34 and 35, respectively.

Figure 36:
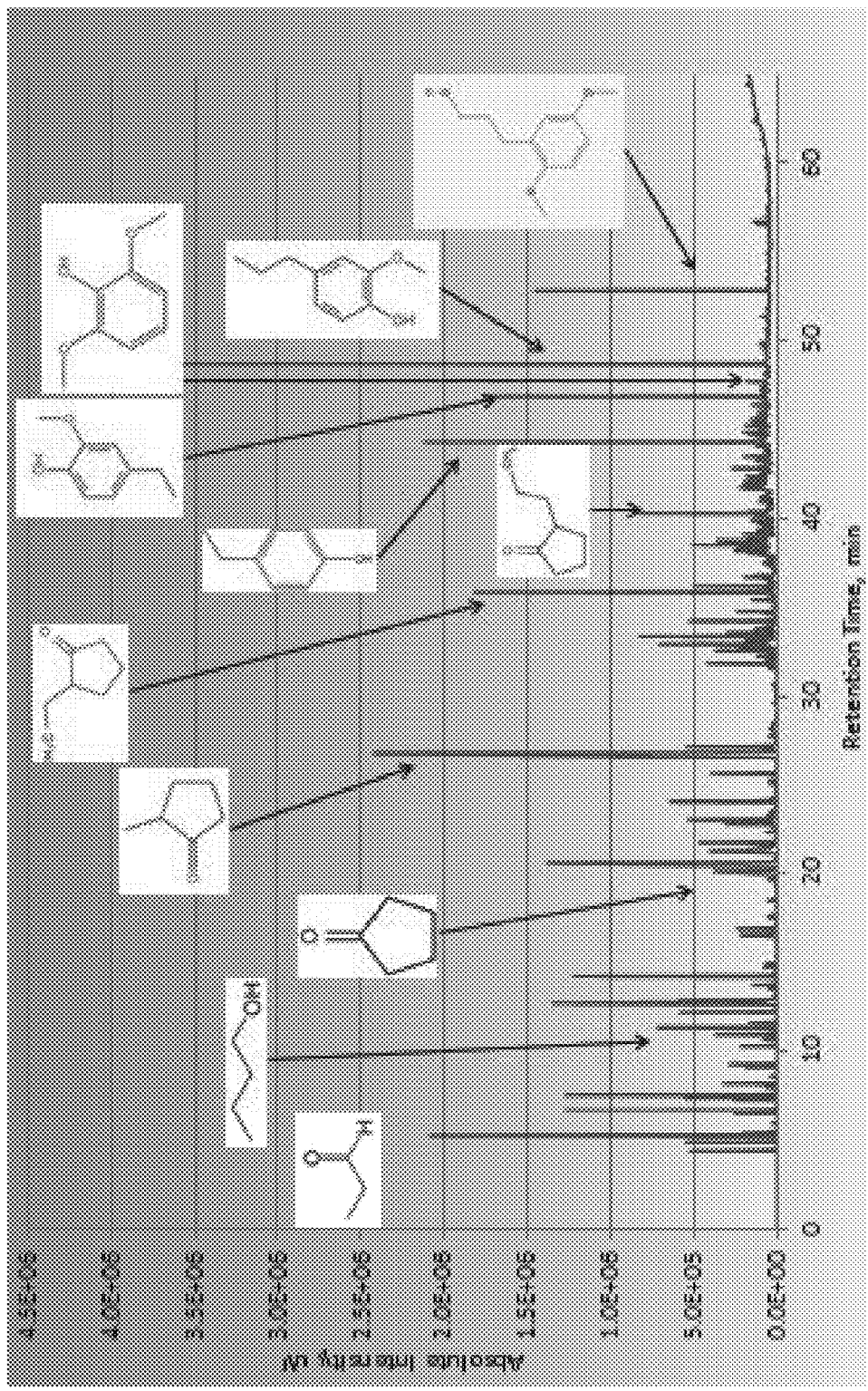
FIG. 36 is a graph providing representative condensable organic products present in the vapor phase from the deconstruction of a biomass feed stream containing bagasse using various deconstruction catalysts according to the present invention.

The residual liquid phase stream consisted mainly of sugars and polyols, whereas the condensed vapor phase stream consisted mainly of alcohols and ketones that were volatilized during the reaction. The condensed vapor phase also contained an organic product shown in FIG. 36. Speciation of this stream shows reaction of the cellulose and hemicellulose to alcohols and cyclic ethers. Additionally the product profile shows products of lignin deconstruction in the substituted benzene compounds, components not seen when using pure cellulose or carbohydrate based feedstocks.

The invention claimed is:
1. A method of converting biomass to biomass-derived fuels and chemicals, the method comprising:
   providing a biomass feed stream comprising a solvent and a biomass component comprising cellulose, hemicellulose or lignin, wherein the solvent comprises one or more members selected from the group consisting of water, in situ generated $C_{2+}O_{2+}$ oxygenated hydrocarbons, recycled $C_{2+}O_{2+}$ oxygenated hydrocarbons, bioreforming solvents, organic solvents, organic acids, and a mixture thereof;
   catalytically reacting the biomass feed stream with hydrogen and a deconstruction catalyst at a deconstruction temperature and a deconstruction pressure to produce a product stream comprising a vapor phase, a liquid phase and a solid phase, the vapor phase comprising one or more volatile $C_{2+}O_{1-2}$ oxygenates, the liquid phase comprising water and one or more $C_{2+}O_{2+}$ oxygenated hydrocarbons, and the solid phase comprising extractives;
   separating the volatile $C_{2+}O_{1-2}$ oxygenates from the liquid phase and solid phase; and
   catalytically reacting the volatile $C_{2+}O_{1-2}$ oxygenates in the presence of a condensation catalyst at a condensation temperature and condensation pressure to produce a $C_{4+}$ compound comprising a member selected from the group consisting of $C_{4+}$ alcohol, $C_{4+}$ ketone, $C_{4+}$ alkane, $C_{4+}$ alkene, $C_{5+}$ cycloalkane, $C_{5+}$ cycloalkene, aryl, fused aryl, and a mixture thereof.

2. The method of claim 1 wherein the solid phase further comprises the deconstruction catalyst.

3. The method of claim 2 further comprising the steps of:
   separating the deconstruction catalyst from the liquid phase;

washing the deconstruction catalyst in one or more washing medium;

regenerating the deconstruction catalyst in the presence of oxygen or hydrogen, at a regenerating pressure and regenerating temperature wherein carbonaceous deposits are removed from the deconstruction catalyst; and reintroducing the deconstruction catalyst to react with the biomass feed stream.

4. The method of claim 1 wherein the biomass component comprises at least one member selected from the group including recycled fibers, corn stover, bagasse, switch grass, miscanthus, sorghum, wood, wood waste, agricultural waste, algae, and municipal waste.

5. The method of claim 1 wherein the deconstruction catalyst comprises an acidic support or a basic support.

6. The method of claim 1 wherein the deconstruction catalyst comprises a support and a member selected from the group consisting of Ru, Co, Rh, Pd, Ni, Mo, and alloys thereof.

7. The method of claim 6 wherein the deconstruction catalyst further comprises a member selected from the group consisting of Pt, Re, Fe, Ir, Cu, Mn, Cr, Mo, B, W, V, Nb, Ta, Ti, Zr, Y, La, Sc, Zn, Cd, Ag, Au, Sn, Ge, P, Al, Ga, In, Tl, and alloys thereof.

8. The method of claim 6 wherein the support comprises a member selected from group consisting of a nitride, carbon, silica, alumina, zirconia, titania, vanadia, ceria, boron nitride, heteropolyacid, kieselguhr, hydroxyapatite, zinc oxide, chromia, zeolites, tungstated zirconia, titania zirconia, sulfated zirconia, phosphated zirconia, acidic alumina, silica-alumina, sulfated alumina, phosphated alumina, theta alumina, and mixtures thereof.

9. The method of claim 7 wherein the support is modified by treating the support with a modifier selected from the group consisting of tungsten, titania, sulfate, phosphate, or silica.

10. The method of claim 1 wherein the deconstruction temperature is in the range of about 120° C. to 350° C.

11. The method of claim 1 wherein the deconstruction pressure is in the range of about 300 psi to 2500 psi.

12. The method of claim 4 wherein the washing medium comprises a liquid selected from the group consisting of water, an acid, a base, a chelating agent, alcohols, ketones, cyclic ethers, hydroxyketones, aromatics, alkanes, and combinations thereof.

13. The method of claim 3 wherein the step of washing the deconstruction catalyst comprises a first step of washing the deconstruction catalysts with a first washing solvent and a second step of washing the deconstruction catalyst with a second washing solvent.

14. The method of claim 13 wherein the first washing solvent comprises a liquid selected from the group consisting of water, an acid, a base, a chelating agent, and combinations thereof, and the second washing solvent comprises a liquid selected from the group consisting of alcohols, ketones, cyclic ethers, hydroxyketones, aromatics, alkanes, and combinations thereof.

15. The method of claim 13 wherein the first washing solvent comprises a liquid selected from the group consisting of alcohols, ketones, cyclic ethers, hydroxyketones, aromatics, alkanes, and combinations thereof, and the second washing solvent comprises a liquid selected from the group consisting of water, an acid, a base, a chelating agent, and combinations thereof.

16. The method of claim 3 wherein the regeneration temperature is in the range of about 120° C. to about 450° C., and is adjusted at a rate of about 20° C. per hour to about 60° C. per hour.

17. The method of claim 3 wherein the regeneration of the deconstruction catalyst further comprises providing a gas stream comprising an inert gas and oxygen, the inert gas provided at a gas flow of between 600-1200 ml gas/ml catalyst per hour and the oxygen provided at a concentration of 0.5-10% of the gas stream.

18. The method of claim 3 wherein more than 90% of the carbonaceous deposits are removed from the deconstruction catalyst.

19. The method of claim 1, wherein the condensation catalyst comprises a metal selected from the group consisting of Cu, Ag, Au, Pt, Ni, Fe, Co, Ru, Zn, Cd, Ga, In, Rh, Pd, Ir, Re, Mn, Cr, Mo, W, Sn, Os, an alloy thereof, and a combination thereof.

20. The method of claim 19, wherein the condensation catalyst further comprises a modifier selected from the group consisting of Ce, La, Y, Li, Na, K, Rb, Cs, Mg, Ca, Sr, Ba, P, B, Bi, and a combination thereof.

21. The method of claim 1, wherein the condensation catalyst comprises a member selected from the group consisting of an acidic alumina, aluminum phosphate, silica-alumina phosphate, amorphous silica-alumina, sulfated alumina, theta alumina, aluminosilicate, zeolites, zirconia, sulfated zirconia, tungstated zirconia, titania zirconia, phosphated zirconia, tungsten carbide, molybdenum carbide, titania, sulfated carbon, phosphated carbon, phosphated silica, phosphated alumina, acidic resin, heteropolyacid, inorganic acid, and a combination thereof.

22. The method of claim 1, wherein the $C_{4+}$ compound is benzene, toluene or xylene.

23. The method of claim 1, wherein the hydrogen is selected from the group consisting of external hydrogen, recycled hydrogen or in situ generated hydrogen.

24. The method of claim 23, wherein the in situ generated hydrogen is derived from the $C_{2+}O_{2+}$ oxygenated hydrocarbons.

* * * * *

UNITED STATES PATENT AND TRADEMARK OFFICE
CERTIFICATE OF CORRECTION

| | |
|---|---|
| PATENT NO. | : 9,873,837 B2 |
| APPLICATION NO. | : 14/968344 |
| DATED | : January 23, 2018 |
| INVENTOR(S) | : Ming Qiao et al. |

It is certified that error appears in the above-identified patent and that said Letters Patent is hereby corrected as shown below:

In the Specification

Column 35, Line 1, "$H_z$" should be -- $H_2$ --

Signed and Sealed this
Twenty-third Day of July, 2019

Andrei Iancu
*Director of the United States Patent and Trademark Office*